(12) United States Patent
Sugiyama

(10) Patent No.: US 8,557,779 B2
(45) Date of Patent: Oct. 15, 2013

(54) CANCER VACCINE COMPOSITION

(75) Inventor: Haruo Sugiyama, Minoh (JP)

(73) Assignee: International Institute of Cancer Immunology, Inc., Suita-shi (JP)

( * ) Notice: Subject to any disclaimer, the term of this patent is extended or adjusted under 35 U.S.C. 154(b) by 29 days.

(21) Appl. No.: 12/746,257

(22) PCT Filed: Dec. 5, 2008

(86) PCT No.: PCT/JP2008/072160
§ 371 (c)(1),
(2), (4) Date: Jun. 4, 2010

(87) PCT Pub. No.: WO2009/072610
PCT Pub. Date: Jun. 11, 2009

(65) Prior Publication Data
US 2011/0070251 A1 Mar. 24, 2011

(30) Foreign Application Priority Data
Dec. 5, 2007 (JP) ................................. 2007-314552

(51) Int. Cl.
*A61K 38/00* (2006.01)
(52) U.S. Cl.
USPC ........................................................ 514/19.3
(58) Field of Classification Search
None
See application file for complete search history.

(56) References Cited

U.S. PATENT DOCUMENTS

| | | |
|---|---|---|
| 7,030,212 B1 | 4/2006 | Sugiyama et al. |
| 2005/0266014 A1 | 12/2005 | Sugiyama et al. |
| 2006/0093615 A1 | 5/2006 | Sugiyama et al. |
| 2007/0082860 A1 | 4/2007 | Sugiyama et al. |
| 2009/0281043 A1 | 11/2009 | Sugiyama et al. |

FOREIGN PATENT DOCUMENTS

| | | | |
|---|---|---|---|
| EP | 1 640 458 A1 | | 3/2006 |
| WO | 00 06602 | | 2/2000 |
| WO | 00/26249 | * | 5/2000 |
| WO | 03 106682 | | 12/2003 |

OTHER PUBLICATIONS

Haigh et al, Oncology vol. 13 p. 1561 (1999).*
Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Zheyu Li, et al., "Identification of a WT1 Protein-Derived Peptide, $WT1_{187}$, as a HLA-A*0206-Restricted, WT1-Specific CTL Epitope", Microbiol. Immunol., 2008, 52, pp. 551-558.
Tanigaki, Nobuyuki et al., "HLA-A2-Binding Peptides Cross-React Not Only Within the A2 Subgroup But Also with Other HLA-A-Locus Allelic Products", Human Immunology, vol. 39, No, 3, pp. 155-162, (1994).
Ganymed Pharmaceuticals AG, RE: European Patent Application No. 99952682.5-2405, Reply to examination report, [online], Jan. 10, 2005.
Extended European Search Report issued Feb. 15, 2012, in European Patent Application No. 08857437.1.
Brett Trost, et al., "Strength in numbers: achieving greater accuracy in MHC-1 binding prediction by combining the results from mutiple Prediction tools", Immunome Research, Biomed Central, vol. 3, No. 1, XP-021025750, Mar. 24, 2007, 10 pages.

* cited by examiner

*Primary Examiner* — Sheela J Huff
(74) *Attorney, Agent, or Firm* — Oblon, Spivak, McClelland, Maier & Neustadt, L.L.P.

(57) ABSTRACT

A cancer vaccine composition for human leukocyte antigen (HLA)-A*0206-positive persons, comprising a protein product of the tumor suppressor gene WT1 or a partial peptide thereof.

4 Claims, 23 Drawing Sheets

SEQUENCE LISTING

```
<160> NUMBER OF SEQ ID NOS: 79

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220
```

```
Asn Leu Tyr Gln Met Thr Ser Gln Leu Glu Cys Met Thr Trp Asn Gln
225                 230                 235                 240
Met Asn Leu Gly Ala Thr Leu Lys Gly Val Ala Ala Gly Ser Ser Ser
            245                 250                 255
Ser Val Lys Trp Thr Glu Gly Gln Ser Asn His Ser Thr Gly Tyr Glu
        260                 265                 270
Ser Asp Asn His Thr Thr Pro Ile Leu Cys Gly Ala Gln Tyr Arg Ile
    275                 280                 285
His Thr His Gly Val Phe Arg Gly Ile Gln Asp Val Arg Arg Val Pro
290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
            340                 345                 350
Tyr Gln Cys Asp Phe Lys Asp Cys Glu Arg Arg Phe Ser Arg Ser Asp
        355                 360                 365
Gln Leu Lys Arg His Gln Arg Arg His Thr Gly Val Lys Pro Phe Gln
    370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                405                 410                 415
Arg Trp Pro Ser Cys Gln Lys Lys Phe Ala Arg Ser Asp Glu Leu Val
            420                 425                 430
Arg His His Asn Met His Gln Arg Asn Met Thr Lys Leu Gln Leu Ala
        435                 440                 445
Leu

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Leu Gly Glu Gln Gln Tyr Ser Val
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Met Phe Pro Asn Ala Pro Tyr Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 4

Gly Leu Gly Glu Gln Gln Tyr Ser Val
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Gly Glu Gln Gln Tyr Ser Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Leu Gly Glu Gln Gln Tyr Ser Val
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Leu Gly Glu Gln Gln Tyr Ser Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Leu Gly Glu Gln Gln Tyr Ser Val
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Leu Gly Glu Gln Gln Tyr Ser Val
1               5

<210> SEQ ID NO 10
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Leu Gly Glu Gln Gln Tyr Ser Val
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Leu Gly Glu Gln Gln Tyr Ser Val
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Leu Gly Glu Gln Gln Tyr Ser Val
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Val Gly Glu Gln Gln Tyr Ser Val
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gln Gly Glu Gln Gln Tyr Ser Val
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ile Gly Glu Gln Gln Tyr Ser Val
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Met Gly Glu Gln Gln Tyr Ser Val
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Leu Leu Glu Gln Gln Tyr Ser Val
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Leu Ala Glu Gln Gln Tyr Ser Val
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Leu Val Glu Gln Gln Tyr Ser Val
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Leu Met Glu Gln Gln Tyr Ser Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Ser Leu Pro Glu Gln Gln Tyr Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Leu Trp Glu Gln Gln Tyr Ser Val
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Leu Phe Glu Gln Gln Tyr Ser Val
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Leu Tyr Glu Gln Gln Tyr Ser Val
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Leu Ser Glu Gln Gln Tyr Ser Val
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Leu Ile Glu Gln Gln Tyr Ser Val
1               5

<210> SEQ ID NO 27
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 27

Gly Met Phe Pro Asn Ala Pro Tyr Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Met Phe Pro Asn Ala Pro Tyr Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Met Phe Pro Asn Ala Pro Tyr Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Met Phe Pro Asn Ala Pro Tyr Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Met Phe Pro Asn Ala Pro Tyr Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Met Phe Pro Asn Ala Pro Tyr Leu
1               5
```

```
<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Met Phe Pro Asn Ala Pro Tyr Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Met Phe Pro Asn Ala Pro Tyr Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Met Phe Pro Asn Ala Pro Tyr Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Val Phe Pro Asn Ala Pro Tyr Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Gln Phe Pro Asn Ala Pro Tyr Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38
```

```
Arg Ala Phe Pro Asn Ala Pro Tyr Leu
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Leu Phe Pro Asn Ala Pro Tyr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ile Phe Pro Asn Ala Pro Tyr Leu
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Met Ile Pro Asn Ala Pro Tyr Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Met Leu Pro Asn Ala Pro Tyr Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Met Gly Pro Asn Ala Pro Tyr Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 44

Arg Met Ala Pro Asn Ala Pro Tyr Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Met Val Pro Asn Ala Pro Tyr Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Met Met Pro Asn Ala Pro Tyr Leu
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Met Pro Pro Asn Ala Pro Tyr Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Met Trp Pro Asn Ala Pro Tyr Leu
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Met Phe Pro Asn Ala Pro Tyr Val
1               5

<210> SEQ ID NO 50
<211> LENGTH: 9
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Met Phe Pro Asn Ala Pro Tyr Ala
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Met Phe Pro Asn Ala Pro Tyr Ile
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Met Phe Pro Asn Ala Pro Tyr Met
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Leu Gly Glu Gln Gln Tyr Ser Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Leu Gly Glu Gln Gln Tyr Ser Val
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Leu Gly Glu Gln Gln Tyr Ser Val
1               5

```
<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Leu Gly Glu Gln Gln Tyr Ser Val
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Leu Gly Glu Gln Gln Tyr Ser Val
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Leu Gly Glu Gln Gln Tyr Ser Val
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Leu Gly Glu Gln Gln Tyr Ser Val
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Leu Gly Glu Gln Gln Tyr Ser Val
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 61

Arg Leu Gly Glu Gln Gln Tyr Ser Val
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Leu Gly Glu Gln Gln Tyr Ser Val
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Met Phe Pro Asn Ala Pro Tyr Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Met Phe Pro Asn Ala Pro Tyr Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Met Phe Pro Asn Ala Pro Tyr Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Met Phe Pro Asn Ala Pro Tyr Leu
1               5

<210> SEQ ID NO 67
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 67

Asn Met Phe Pro Asn Ala Pro Tyr Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Met Phe Pro Asn Ala Pro Tyr Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Met Phe Pro Asn Ala Pro Tyr Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Met Phe Pro Asn Ala Pro Tyr Leu
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Met Phe Pro Asn Ala Pro Tyr Leu
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ile Phe Pro Asn Ala Pro Tyr Ile
1               5
```

```
<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ile Phe Pro Asn Ala Pro Tyr Val
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Leu Phe Pro Asn Ala Pro Tyr Ile
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Leu Phe Pro Asn Ala Pro Tyr Val
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Gln Gln Tyr Ser
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Gln Gln Tyr Ser Val
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Pro Asn Ala Pro Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser(tBu)
<220> FEATURE:
<221> NAME/KEY: MOD_RES
<222> LOCATION: (4)..(4)
<223> OTHER INFORMATION: Glu(OtBu)
<220> FEATURE:
<221> NAME/KEY: MOD_RES
<222> LOCATION: (5)..(6)
<223> OTHER INFORMATION: Gln(Trt)
<220> FEATURE:
<221> NAME/KEY: MOD_RES
<222> LOCATION: (7)..(7)
<223> OTHER INFORMATION: Tyr(tBu)
<220> FEATURE:
<221> NAME/KEY: MOD_RES
<222> LOCATION: (8)..(8)
<223> OTHER INFORMATION: Ser(tBu)
<220> FEATURE:
<221> NAME/KEY: MOD_RES
<222> LOCATION: (9)..(9)
<223> OTHER INFORMATION: Val-Alko-resin

<400> SEQUENCE: 79

Ser Val Gly Glu Gln Gln Tyr Ser Val
1               5
```

CANCER VACCINE COMPOSITION

CROSS-REFERENCE TO RELATED APPLICATIONS

The present application is a 35 U.S.C. §371 National Stage patent application of International patent application PCT/JP2008/072160, filed on Dec. 5, 2008, which claims priority to Japanese patent application JP 2007-314552, filed on Dec. 5, 2007.

TECHNICAL FIELD

The present invention relates to a cancer vaccine composition for human leukocyte antigen (HLA)-A*0206-positive persons, comprising a protein product of the tumor suppressor gene Wilms' tumor 1 (WT1) (hereinafter sometimes abbreviated as WT1 protein) or a partial peptide thereof (hereinafter sometimes abbreviated as WT1 peptide). The present invention also relates to a cancer vaccine composition for HLA-A*0206-positive persons, comprising DNA or RNA encoding the above-mentioned WT1 protein or WT1 peptide, a method for inducing WT1-specific CTLs, a method for inducing dendritic cells that present a cancer antigen, and a method of cancer diagnosis for HLA-A*0206-positive persons, and a method of cancer treatment or prevention in HLA-A*0206-positive persons.

The present invention further relates to a cancer vaccine composition for HLA-A*0201-positive persons, comprising a modified peptide of the WT1 peptide.

BACKGROUND ART

The Wilms' tumor gene WT1 was isolated as a gene associated with tumorigenesis in Wilms' tumor, which is a pediatric renal tumor (see nonpatent literature 1). This gene encodes a zinc finger transcription factor associated with the regulatory mechanism of cell growth and differentiation, and apoptosis and tissue development.

The WT1 gene was originally classified as a tumor suppressor gene. However, based on the recent evidences shown in the following (i) to (iii):
(i) high expression of the wild-type WT1 gene in various human malignant tumors and solid cancers including hematopoietic malignant tumors such as leukemia and myelodysplastic syndromes (MDS),
(ii) growth inhibition of human leukemia cells and solid cancer cells treated by WT1 antisense oligonucleotides, and
(iii) growth promotion and differentiation inhibition of mouse myeloid precursor cells by constitutive expression of the wild-type WT1 gene,
it is suggested that the wild-type WT1 gene exhibits an oncogenic effect rather than a tumor suppressive effect on various malignant diseases (see patent literature 1).

There is also known high expression of the WT1 gene in solid cancers, such as gastric cancer, colon cancer, lung cancer, breast cancer, germ cell cancer, hepatic cancer, skin cancer, bladder cancer, prostate cancer, uterine cancer, cervical cancer and ovarian cancer (see patent literature 2).

In general, the immune system for eliminating foreign substances comprises humoral immunity, in which macrophages, which recognize an antigen and serve as antigen presenting cells, helper T cells, which recognize the antigen presented by the macrophages and produce various lymphokines to activate other T cells, and B lymphocytes, which differentiate into antibody producing cells via the actions of the lymphokines, are involved; and cell-mediated immunity, in which cytotoxic T lymphocytes (CTLs), which are produced through differentiation in response to antigen presentation, attack and destroy target cells.

Currently, it has been considered that cancer immunity is mainly based on cell-mediated immunity in which CTLs are involved. In the CTL-based cancer immunity, precursor T cells recognize a cancer antigen presented in the form of a complex of a major histocompatibility complex (MHC) class I and the cancer antigen, and thereby differentiate and grow into CTLs, which attack and destroy cancer cells. In this case, the cancer cell presents, on the cell surface, a complex of the MHC class I antigen and the cancer antigen, which is the target of the CTLs (see nonpatent literatures 2 to 5). MHC is called as a human leukocyte antigen (HLA) in humans.

It is considered that the above-mentioned cancer antigen, which is presented by an MHC class I antigen on the surfaces of cancer cells, i.e., target cells, is a peptide of about 8 to 12 amino acids produced through intracellular protease-mediated processing of an antigen protein synthesized in cancer cells (see nonpatent literatures 2 to 5). Currently, search for antigen proteins of various cancers is underway, but only a few proteins have been identified as a cancer specific antigen.

The present inventor synthesized polypeptides that each consist of 7 to 30 contiguous amino acids based on the amino acid sequence of the WT1 gene expression product and each contain at least one amino acid presumably serving as an anchor amino acid for binding with HLA-A*2402 or HLA-A*0201, confirmed that these peptides bind with HLA-A*2402 or HLA-A*0201 (these peptides are HLA-A*2402- or HLA-A*0201-restricted), and found that the binding of the peptides with HLA-A*2402 or HLA-A*0201 induces CTLs, resulting in cytotoxic response to target cells (hereinafter abbreviated as CTL response). From this fact, these peptides were identified as a CTL epitope derived from the WT1 gene expression product (WT protein).

At this point, WT1-specific CTL epitopes only for HLA-A*2402 and HLA-A*0201 (see patent literature 3), HLA-A*3303 (see patent literature 4) or HLA-A*1101 are identified (see patent literature 5). It is confirmed that CTL responses induced by the polypeptides disclosed by the above literatures are restricted by HLA-A*2402, HLA-A*0201, HLA-A*3303 and HLA-A*1101.

This indicates a possibility that the protein product of the tumor suppressor gene WT1 is a promising tumor rejection antigen, also called as a tumor associated antigen (TAA). In fact, high levels of WT1-specific CTLs or high-titer anti-WT1 antibodies were observed not in peripheral blood of healthy blood donors, but in that of cancer patients.

However, HLA types are diverse enough to serve as markers for identifying individuals. In the HLAs, MHC class I antigens are classified into HLA-A, HLA-B and HLA-C, and MHC class II antigens are classified into HLA-DP, HLA-DQ and HLA-DR. Each class has several types of antigens. The antigen binding site of each HLA has genetic polymorphism. For example, it is known that HLA-A, HLA-B and HLA-C have 27 or more, 59 or more, and 10 or more kinds of polymorphisms (alleles), respectively.

Therefore, there has been a desire to identify a cancer antigen that binds to other types of HLAs than HLA-A*2402, HLA-A*0201, HLA-A*3303 and HLA-A*1101 and induces a CTL response, and to thereby apply immunotherapy to a wider range of subjects.

Meanwhile, the following three of modified WT1 peptides were reported in two documents:
the $WT1_{187}P1Y$ peptide (YLGEQQYSV; SEQ ID NO: 12),
the $WT1_{126}P1Y$ peptide (YMFPNAPYL; SEQ ID NO: 35)

(see patent literature 6 for the above two peptides), and the WT1$_{126}$P9M peptide (RMFPNAPYM; SEQ ID NO: 52) (see patent literature 7).

Further, the following two peptides were reported in the written argument for the examination of European patent No. 1127068:
the WT1$_{126}$P2L peptide (RLFPNAPYL; SEQ ID NO: 39) and the WT1$_{126}$P2L&P9V peptide (RLFPNAPYV; SEQ ID NO: 75) (see nonpatent literature 7).

However, it has never been reported whether these WT1 modified peptides serve as a cancer antigen that binds to other types of HLAs than HLA-A*2402, HLA-A*0201, HLA-A*3303 and HLA-A*1101 and induces a CTL response.

Patent Literature 1: JP-A 9-104629
Patent Literature 2: JP-A 11-035484
Patent Literature 3: WO 00/06602 pamphlet
Patent Literature 4: Japanese Patent Application No. 2006-045287
Patent Literature 5: Japanese Patent Application No. 2006-355356
Patent Literature 6: WO 2005/053618 pamphlet
Patent Literature 7: WO 2007/016466 pamphlet
Non Patent Literature 1: Gessler, M. et al., Nature, vol. 343, pp. 774-778, 1990
Non Patent Literature 2: Cur. Opin. Immunol., vol. 5, p. 709, 1993
Non Patent Literature 3: Cur. Opin. Immunol., vol. 5, p. 719, 1993
Non Patent Literature 4: Cell, vol. 82, p. 13, 1995
Non Patent Literature 5: Immunol. Rev., vol. 146, p. 167, 1995
Non Patent Literature 6: Mol. Cell. Biol., vol. 11, p. 1707, 1991
Non Patent Literature 7: The written argument for the examination of European patent No. 1127068

SUMMARY OF INVENTION

Problem to be Solved by the Invention

An object of the present invention is to apply, further to HLA-A*0206-positive persons, a method of cancer treatment and/or prevention for patients with malignant tumors including leukemia, the method being based on a protein product of the tumor suppressor gene WT1 (WT1 protein) or a partial peptide thereof (WT1 peptide).

Means for Solving the Problem

The present inventor conducted intensive studies to achieve the above-mentioned object. As a result, he found that the WT1$_{187}$ peptide (SLGEQQYSV (SEQ ID NO: 2)) and the WT1$_{126}$ peptide (RMFPNAPYL (SEQ ID NO: 3)) each derived from the human WT1 protein, which were known to induce HLA-A*0201-restricted CTLs only, surprisingly induce HLA-A*0206-restricted CTLs as well. Under the circumstances where only the peptides described in WO 00/06602 pamphlet were known as a WT1 peptide that induces HLA-A*0201-restricted CTLs, the present inventor found that a modified peptide of the WT1$_{187}$ peptide (also referred to as a modified WT1$_{187}$ peptide) and a modified peptide of the WT1$_{126}$ peptide (also referred to as a WT1$_{126}$ modified peptide) also bind to an HLA-A*0201 molecule. Based on these findings, the present inventor conducted further intensive studies and completed the present invention.

Namely, the present invention relates to the following (1) to (17).

(1) A cancer vaccine composition for human leukocyte antigen (HLA)-A*0206-positive persons, comprising a protein product of the tumor suppressor gene WT1 or a partial peptide thereof.
(2) The composition according to the above (1), wherein the protein product of the tumor suppressor gene WT1 is the protein of the following (a) or (b):
(a) a protein consisting of the amino acid sequence of SEQ ID NO: 1, or
(b) a protein consisting of an amino acid sequence comprising deletion, substitution or addition of one to several amino acids in the amino acid sequence (a), either of which is immunogenic in HLA-A*0206-positive persons.
(3) The composition according to the above (1), wherein the partial peptide is

```
                                          (SEQ ID NO: 2)
the WT1₁₈₇ peptide: Ser Leu Gly Glu Gln Gln Tyr Ser Val,
                                          (SEQ ID NO: 3)
the WT1₁₂₆ peptide: Arg Met Phe Pro Asn Ala Pro Tyr Leu,
                                         (SEQ ID NO: 11)
the WT1₁₈₇P1F peptide: Phe Leu Gly Glu Gln Gln Tyr Ser Val,
                                         (SEQ ID NO: 16)
the WT1₁₈₇P2M peptide: Ser Met Gly Glu Gln Gln Tyr Ser Val,
                                         (SEQ ID NO: 20)
the WT1₁₈₇P3M peptide: Ser Leu Met Glu Gln Gln Tyr Ser Val,
                                         (SEQ ID NO: 34)
the WT1₁₂₆P1F peptide: Phe Met Phe Pro Asn Ala Pro Tyr Leu,
                                         (SEQ ID NO: 39)
the WT1₁₂₆P2L peptide: Arg Leu Phe Pro Asn Ala Pro Tyr Leu,
                                         (SEQ ID NO: 46)
the WT1₁₂₆P3M peptide: Arg Met Met Pro Asn Ala Pro Tyr Leu
or
                                         (SEQ ID NO: 49)
the WT1₁₂₆P9V peptide: Arg Met Phe Pro Asn Ala Pro Tyr Val.
```

(4) The composition according to the above (1) to (3), further comprising an adjuvant.
(5) A cancer vaccine composition for HLA-A*0206-positive persons, comprising DNA encoding a protein product of the tumor suppressor gene WT1 or a partial peptide thereof.
(6) A cancer vaccine composition for HLA-A*0206-positive persons, comprising RNA encoding a protein product of the tumor suppressor gene WT1 or a partial peptide thereof.
(7) A method for inducing WT1-specific CTLs, comprising culturing, in the presence of a protein product of the tumor suppressor gene WT1 or a partial peptide thereof, peripheral blood mononuclear cells (PBMCs) derived from an HLA-A*0206-positive person, to obtain WT1-specific CTLs induced therefrom.

(8) A method for inducing dendritic cells that present a protein product of the tumor suppressor gene WT1 or a partial peptide thereof, comprising culturing, in the presence of the protein product or a partial peptide thereof, immature dendritic cells derived from an HLA-A*0206-positive person, to obtain dendritic cells induced therefrom which present the protein product or a partial peptide thereof.

(9) A method of cancer diagnosis for HLA-A*0206-positive persons, comprising
i) a step of detecting or quantifying a protein product of the tumor suppressor gene WT1 or a partial peptide thereof, an antibody thereagainst or WT1-specific CTLs in a sample from an HLA-A*0206-positive person, and a step of comparing the amount of the protein or a partial peptide thereof, an antibody thereagainst or the WT1-specific CTLs, with that in the case where cancer is not developed, or
ii) a step of administering an HLA-A*0206-positive subject WT1-specific CTLs induced by the method mentioned in the above (7) or dendritic cells induced by the method mentioned in the above (8), and a step of determining the position or region of the CTLs or dendritic cells in the HLA-A*0206-positive subject.

(10) A cancer vaccine composition for HLA-A*0201-positive persons, comprising the following peptide:
a modified peptide of the $WT1_{187}$ peptide: Ser Leu Gly Glu Gln Gln Tyr Ser Val (SEQ ID NO: 2) or the $WT1_{126}$ peptide: Arg Met Phe Pro Asn Ala Pro Tyr Leu (SEQ ID NO: 3), either of which is a partial peptide of a protein product of the tumor suppressor gene WT1, the modified peptide being immunogenic in HLA-A*0201-positive persons.

(11) The composition according to the above (10), wherein the modified peptide is

```
                                         (SEQ ID NO: 11)
the WT1₁₈₇P1F peptide: Phe Leu Gly Glu Gln Gln Tyr Ser Val, (SEQ ID NO: 16)
the WT1₁₈₇P2M peptide: Ser Met Gly Glu Gln Gln Tyr Ser Val, (SEQ ID NO: 20)
the WT1₁₈₇P3M peptide: Ser Leu Met Glu Gln Gln Tyr Ser Val, (SEQ ID NO: 34)
the WT1₁₂₆P1F peptide: Phe Met Phe Pro Asn Ala Pro Tyr Leu, (SEQ ID NO: 39)
the WT1₁₂₆P2L peptide: Arg Leu Phe Pro Asn Ala Pro Tyr Leu, (SEQ ID NO: 46)
the WT1₁₂₆P3M peptide: Arg Met Met Pro Asn Ala Pro Tyr Leu
or (SEQ ID NO: 49)
the WT1₁₂₆P9V peptide: Arg Met Phe Pro Asn Ala Pro Tyr Val.
```

(12) A method of cancer treatment or prevention, comprising administering an HLA-A*0206-positive person a composition containing a protein product of the tumor suppressor gene WT1 or a partial peptide thereof.

(13) A protein product of the tumor suppressor gene WT1 or a partial peptide thereof for cancer treatment or prevention in HLA-A*0206-positive persons.

(14) A method of cancer treatment or prevention, comprising administering an HLA-A*0201-positive person a composition containing the following peptide:
a modified peptide of the $WT1_{187}$ peptide: Ser Leu Gly Glu Gln Gln Tyr Ser Val (SEQ ID NO: 2) or the $WT1_{126}$ peptide: Arg Met Phe Pro Asn Ala Pro Tyr Leu (SEQ ID NO: 3), either of which is a partial peptide of a protein product of the tumor suppressor gene WT1, the modified peptide being immunogenic in HLA-A*0201-positive persons.

(15) The following peptide:
a modified peptide of the $WT1_{187}$ peptide: Ser Leu Gly Glu Gln Gln Tyr Ser Val (SEQ ID NO: 2) or the $WT1_{126}$ peptide: Arg Met Phe Pro Asn Ala Pro Tyr Leu (SEQ ID NO: 3), either of which is a partial peptide of a protein product of the tumor suppressor gene WT1, the modified peptide being immunogenic in HLA-A*0201-positive persons,
for cancer treatment or prevention in HLA-A*0201-positive persons.

(16) A method of cancer treatment or prevention, comprising introducing RNA encoding a protein product of the tumor suppressor gene WT1 or a partial peptide thereof into dendritic cells of an HLA-A*0206-positive person.

(17) RNA encoding a protein product of the tumor suppressor gene WT1 or a partial peptide thereof for cancer treatment or prevention in HLA-A*0206-positive persons.

The present invention also relates to use of a protein product of the tumor suppressor gene WT1 or a partial peptide thereof for production of a cancer vaccine composition used for cancer treatment or prevention in HLA-A*0206-positive persons.

The present invention also relates to use of the following peptide:
a modified peptide of the $WT1_{187}$ peptide: Ser Leu Gly Glu Gln Gin Tyr Ser Val (SEQ ID NO: 2) or the $WT1_{126}$ peptide: Arg Met Phe Pro Asn Ala Pro Tyr Leu (SEQ ID NO: 3), either of which is a partial peptide of a protein product of the tumor suppressor gene WT1, the modified peptide being immunogenic in HLA-A*0201-positive persons,
for production of a cancer vaccine composition used for cancer treatment or prevention in HLA-A*0201-positive persons.

The "cancer vaccine composition" as used herein refers to a medicament used for cancer prevention or treatment via inoculation or administration to an animal including a human. The "treatment" refers to, besides completely curing disease state, stopping progression of disease state by inhibiting progression and/or aggravation of symptoms to some degree even falling short of a complete cure; or improving all or a part of disease state in a direction towards a cure. The "prevention" refers to preventing, inhibiting or delaying disease development.

The following terms: peripheral blood mononuclear cells, immature dendritic cells, WT1-specific CTLs, samples etc. derived from HLA-A*0206-positive or HLA-A*0201-positive persons refer to peripheral blood mononuclear cells, immature dendritic cells, WT1-specific CTLs, biological specimens etc., such as blood, which are isolated or collected from HLA-A*0206-positive or HLA-A*0201-positive persons, respectively. The WT1-specific CTLs derived from HLA-A*0206-positive or HLA-A*0201-positive persons also include CTLs induced from peripheral blood mononuclear cells, immature dendritic cells or biological specimens such as blood, which are isolated or collected from HLA-A*0206-positive or HLA-A*0201-positive persons.

Effect of the Invention

The present invention enables in vivo and in vitro induction of WT1-specific CTLs in HLA-A*0206-positive subjects. Although the subjects of immunotherapy using a vaccine comprising the WT1 protein or WT1 peptide have conventionally been limited to HLA-A*0201-positive patients and HLA-A*2402-positive patients, the present invention can widen the range of the subjects to HLA-A*0206-positive patients. HLA-A2, which is a serotype of HLA class I antigens, is the most frequent in Caucasians (about 50%), and the large majority have HLA-A*0201, while about 4% of Caucasians have HLA-A*0206. On the other hand, HLA-A24 is the most frequent serotype in Japanese people (about 58%), and the large majority have HLA-A*2402. About 42% of Japanese people have HLA-A2. Among them, only about 43% have HLA-A*0201, and the others have HLA-A*0206 or HLA-A*0207. In other words, about 18% of Japanese people have HLA-A*0201, and about 17% of Japanese people have HLA-A*0206. Therefore, the fact that at least an HLA-A*0206-restricted CTL epitope was identified from Japanese people as well as an HLA-A*0201-restricted CTL epitope is significantly useful to widen the subjects of cancer immunotherapy to HLA-A*0206-positive persons. Since 14% of Chinese people and 9% of South Korean people have this allele, it is possible to apply the cancer vaccine composition of the present invention to a further wider range of subjects.

The cancer vaccine composition of the present invention is useful for treatment of WT1-expressing cancers such as hematopoietic tumors and solid cancers in HLA-A*0206-positive persons. The cancer vaccine composition of the present invention is also useful for prevention of cancer development in HLA-A*0206-positive persons.

BRIEF DESCRIPTION OF DRAWINGS

FIG. 1a shows the cytotoxic activity against $^{51}$Cr-labeled B-LCLs. FIG. 1b shows that the cytotoxic activity against $^{51}$Cr-labeled autologous B-LCLs increases in parallel with the concentration of the $WT1_{187}$ peptide used to pulse the PBMCs with.

FIGS. 2a and 2b show the respective cytotoxic activities, against $^{51}$Cr-labeled B-LCLs, of CTLs separately obtained from two healthy blood donors other than the blood donor of FIG. 1a.

BEST MODE FOR CARRYING OUT THE INVENTION

Figure 1:
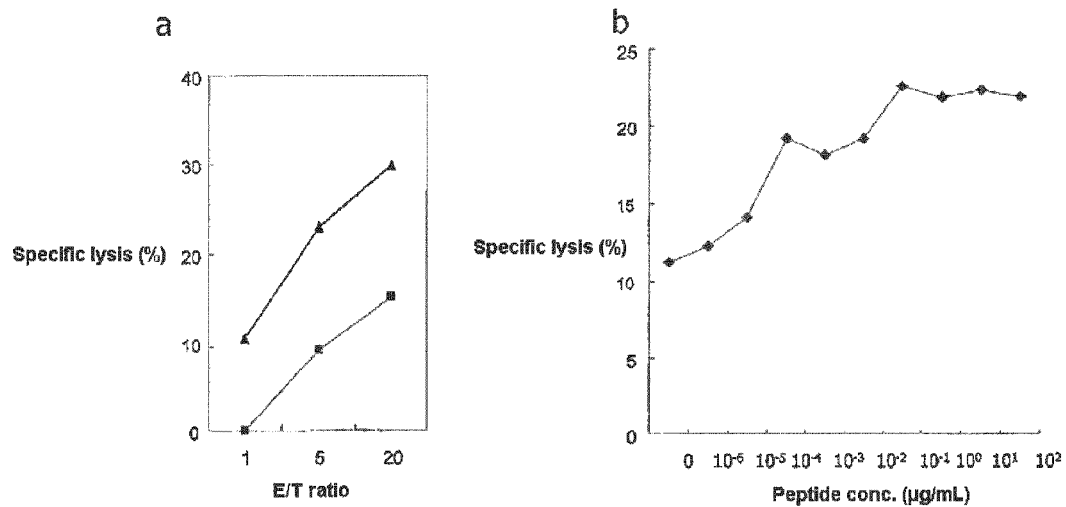
FIG. 1 shows the cytotoxic activity of $WT1_{187}$ peptide-specific CTLs induced from PBMCs of an HLA-A*0206-positive healthy blood donor.

Hereinafter, the present invention will be illustrated.

The following codes are used when amino acid residues are abbreviated in this description and drawings.
Ala or A: Alanine residue
Arg or R: Arginine residue
Asn or N: Asparagine residue
Asp or D: Aspartic acid residue
Cys or C: Cysteine residue
Gln or Q: Glutamine residue
Glu or E: Glutamic acid residue
Gly or G: Glycine residue
His or H: Histidine residue
Ile or I: Isoleucine residue
Leu or L: Leucine residue
Lys or K: Lysine residue
Met or M: Methionine residue
Phe or F: Phenylalanine residue
Pro or P: Proline residue
Ser or S: Serine residue
Thr or T: Threonine residue
Trp or W: Tryptophan residue
Tyr or Y: Tyrosine residue
Val or V: Valine residue The WT1 protein of the present invention may be a gene product of a zinc finger-type transcription factor isolated as a causative gene of Wilms' tumor, the gene product being capable of binding to an HLA-A*0206 molecule and thereby serving as a target antigen of malignant tumors. More specifically, the WT1 protein of the present invention is preferably the human WT1 protein consisting of 449 amino acids (Sequence list: SEQ ID NO: 1) or a protein which consists of an amino acid sequence comprising deletion, substitution or addition of one to several amino acids (preferably about 2 to 6 amino acids) in the amino acid sequence of the human WT1 protein, and which is immunogenic in HLA-A*0206-positive persons. The amino acid used for addition or substitution may be a non-natural amino acid besides 20 gene-encoded amino acids.

The partial peptide of the WT1 protein (WT1 peptide) refers to a peptide consisting of a part of the amino acid sequence that constitutes the WT1 protein. The WT1 peptide may be a peptide which consists of 8 to 12 amino acids, preferably 8 to 9 amino acids derived from the WT1 protein and which binds to an HLA-A*0206 molecule and thereby induces cytotoxic T cells. Particularly preferred is the WT1$_{187}$ peptide (Ser Leu Gly Glu Gln Gln Tyr Ser Val; SEQ ID NO: 2) or the WT1$_{126}$ peptide (Arg Met Phe Pro Asn Ala Pro Tyr Leu; SEQ ID NO: 3), both described in the WO 00/06602 pamphlet.

A modified peptide comprising deletion, substitution or addition of one or several amino acids of the WT1 peptide can also be used as the WT1 peptide of the present invention as long as it is immunogenic in HLA-A*0206-positive persons. Examples of such a modified peptide include a modified WT1$_{187}$ peptide and a modified WT1$_{126}$ peptide.

The modified WT1$_{187}$ peptide is preferably a peptide comprising the same amino acid residues (EQQYS SEQ ID NO: 76)) at positions 4 to 8 from the N terminus as the WT1$_{187}$ peptide has at the corresponding positions, and more preferably a peptide comprising the same amino acid residues (EQQYSV(SEQ ID NO 77)) at positions 4 to 9 from the N terminus as the WT1$_{187}$ peptide has at the corresponding positions. Such a modified WT1$_{187}$ peptide is preferably a peptide consisting of any of the following amino acid sequences of SEQ ID NO: 4 to 26 and 54 to 62.

WT1$_{187}$P1G peptide (GLGEQQYSV; SEQ ID NO: 4)

WT1$_{187}$P1A peptide (ALGEQQYSV; SEQ ID NO: 5)

WT1$_{187}$P1V peptide (VLGEQQYSV; SEQ ID NO: 6)

WT1$_{187}$P1L peptide (LLGEQQYSV; SEQ ID NO: 7)

WT1$_{187}$P1I peptide (ILGEQQYSV; SEQ ID NO: 8)

WT1$_{187}$P1M peptide (MLGEQQYSV; SEQ ID NO: 9)

WT1$_{187}$P1W peptide (WLGEQQYSV; SEQ ID NO: 10)

WT1$_{187}$P1F peptide (FLGEQQYSV; SEQ ID NO: 11)

WT1$_{187}$P1Y peptide (YLGEQQYSV; SEQ ID NO: 12)

WT1$_{187}$P2V peptide (SVGEQQYSV; SEQ ID NO: 13)

WT1$_{187}$P2Q peptide (SQGEQQYSV; SEQ ID NO: 14)

WT1$_{187}$P2I peptide (SIGEQQYSV; SEQ ID NO: 15)

WT1$_{187}$P2M peptide (SMGEQQYSV; SEQ ID NO: 16)

WT1$_{187}$P3L peptide (SLLEQQYSV; SEQ ID NO: 17)

WT1$_{187}$P3A peptide (SLAEQQYSV; SEQ ID NO: 18)

WT1$_{187}$P3V peptide (SLVEQQYSV; SEQ ID NO: 19)

WT1$_{187}$P3M peptide (SLMEQQYSV; SEQ ID NO: 20)

WT1$_{187}$P3P peptide (SLPEQQYSV; SEQ ID NO: 21)

WT1$_{187}$P3W peptide (SLWEQQYSV; SEQ ID NO: 22)

WT1$_{187}$P3F peptide (SLFEQQYSV; SEQ ID NO: 23)

WT1$_{187}$P3Y peptide (SLYEQQYSV; SEQ ID NO: 24)

WT1$_{187}$P3S peptide (SLSEQQYSV; SEQ ID NO: 25)

WT1$_{187}$P3I peptide (SLIEQQYSV; SEQ ID NO: 26)

-continued

WT1₁₈₇P9L peptide (SLGEQQYSL; SEQ ID NO: 53)

WT1₁₈₇P1D peptide (DLGEQQYSV; SEQ ID NO: 54)

WT1₁₈₇P1E peptide (ELGEQQYSV; SEQ ID NO: 55)

WT1₁₈₇P1H peptide (HLGEQQYSV; SEQ ID NO: 56)

WT1₁₈₇P1K peptide (KLGEQQYSV; SEQ ID NO: 57)

WT1₁₈₇P1N peptide (NLGEQQYSV; SEQ ID NO: 58)

WT1₁₈₇P1P peptide (PLGEQQYSV; SEQ ID NO: 59)

WT1₁₈₇P1Q peptide (QLGEQQYSV; SEQ ID NO: 60)

WT1₁₈₇P1R peptide (RLGEQQYSV; SEQ ID NO: 61)

WT1₁₈₇P1T peptide (TLGEQQYSV; SEQ ID NO: 62)

The modified WT1₁₂₆ peptide is preferably a peptide comprising the same amino acid residues (PNAPY (SEQ ID NO: 78)) at positions 4 to 8 from the N terminus as the WT1₁₂₆ peptide has at the corresponding positions. Such a modified WT1₁₂₆ peptide is preferably a peptide consisting of any of the following amino acid sequences of SEQ ID NO: 27 to 52 and 63 to 75.

WT1₁₂₆P1G peptide (GMFPNAPYL; SEQ ID NO: 27)

WT1₁₂₆P1A peptide (AMFPNAPYL; SEQ ID NO: 28)

WT1₁₂₆P1V peptide (VMFPNAPYL; SEQ ID NO: 29)

WT1₁₂₆P1L peptide (LMFPNAPYL; SEQ ID NO: 30)

WT1₁₂₆P1I peptide (IMFPNAPYL; SEQ ID NO: 31)

WT1₁₂₆P1M peptide (MMFPNAPYL; SEQ ID NO: 32)

WT1₁₂₆P1W peptide (WMFPNAPYL; SEQ ID NO: 33)

WT1₁₂₆P1F peptide (FMFPNAPYL; SEQ ID NO: 34)

WT1₁₂₆P1Y peptide (YMFPNAPYL; SEQ ID NO: 35)

WT1₁₂₆P2V peptide (RVFPNAPYL; SEQ ID NO: 36)

WT1₁₂₆P2Q peptide (RQFPNAPYL; SEQ ID NO: 37)

WT1₁₂₆P2A peptide (RAFPNAPYL; SEQ ID NO: 38)

WT1₁₂₆P2L peptide (RLFPNAPYL; SEQ ID NO: 39)

WT1₁₂₆P2I peptide (RIFPNAPYL; SEQ ID NO: 40)

WT1₁₂₆P3I peptide (RMIPNAPYL; SEQ ID NO: 41)

WT1₁₂₆P3L peptide (RMLPNAPYL; SEQ ID NO: 42)

WT1₁₂₆P3G peptide (RMGPNAPYL; SEQ ID NO: 43)

WT1₁₂₆P3A peptide (RMAPNAPYL; SEQ ID NO: 44)

WT1₁₂₆P3V peptide (RMVPNAPYL; SEQ ID NO: 45)

WT1₁₂₆P3M peptide (RMMPNAPYL; SEQ ID NO: 46)

WT1₁₂₆P3P peptide (RMPPNAPYL; SEQ ID NO: 47)

WT1₁₂₆P3W peptide (RMWPNAPYL; SEQ ID NO: 48)

WT1₁₂₆P9V peptide (RMFPNAPYV; SEQ ID NO: 49)

WT1₁₂₆P9A peptide (RMFPNAPYA; SEQ ID NO: 50)

WT1₁₂₆P9I peptide (RMFPNAPYI; SEQ ID NO: 51)

-continued

WT1₁₂₆P9M peptide (RMFPNAPYM; SEQ ID NO: 52)

WT1₁₂₆P1D peptide (DMFPNAPYL; SEQ ID NO: 63)

WT1₁₂₆P1E peptide (EMFPNAPYL; SEQ ID NO: 64)

WT1₁₂₆P1H peptide (HMFPNAPYL; SEQ ID NO: 65)

WT1₁₂₆P1K peptide (KMFPNAPYL; SEQ ID NO: 66)

WT1₁₂₆P1N peptide (NMFPNAPYL; SEQ ID NO: 67)

WT1₁₂₆P1P peptide (PMFPNAPYL; SEQ ID NO: 68)

WT1₁₂₆P1Q peptide (QMFPNAPYL; SEQ ID NO: 69)

WT1₁₂₆P1S peptide (SMFPNAPYL; SEQ ID NO: 70)

WT1₁₂₆P1T peptide (TMFPNAPYL; SEQ ID NO: 71)

WT1₁₂₆P2I&P9I peptide (RIFPNAPYI; SEQ ID NO: 72)

WT1₁₂₆P2I&P9V peptide (RIFPNAPYV; SEQ ID NO: 73)

WT1₁₂₆P2L&P9I peptide (RLFPNAPYI; SEQ ID NO: 74)

WT1₁₂₆P2L&P9V peptide (RLFPNAPYV; SEQ ID NO: 75)

Inter alia, the modified WT1₁₈₇ peptide is preferably the WT1₁₈₇P1F peptide (SEQ ID NO: 11), the WT1₁₈₇P2M peptide (SEQ ID NO: 16) or the WT1₁₈₇P3M peptide (SEQ ID NO: 20), more preferably the WT1₁₈₇P1F peptide or the WT1₁₈₇P2M peptide, and still more preferably the WT1₁₈₇P2M peptide. The modified WT1₁₂₆ peptide is preferably the WT1₁₂₆P1F peptide (SEQ ID NO: 34), the WT1₁₂₆P2L peptide (SEQ ID NO: 39), the WT1₁₂₆P3M peptide (SEQ ID NO: 46) or the WT1₁₂₆P9V peptide (SEQ ID NO: 49), more preferably the WT1₁₂₆P2L peptide, the WT1₁₂₆P3M peptide or the WT1₁₂₆P9V peptide, and still more preferably the WT1₁₂₆P9V peptide.

The WT1 peptide in the cancer vaccine composition of the present invention is preferably the WT1₁₈₇ peptide, the WT1₁₂₆ peptide, the WT1₁₈₇P1F peptide, the WT1₁₈₇P2M peptide, the WT1₁₈₇P3M peptide, the WT1₁₂₆P1F peptide, the WT1₁₂₆P2L peptide, the WT1₁₂₆P3M peptide or the WT1₁₂₆P9V peptide. More preferred is the WT1₁₈₇ peptide, the WT1₁₂₆ peptide, the WT1₁₈₇P1F peptide, the WT1₁₈₇P2M peptide, the WT1₁₂₆P2L peptide, the WT1₁₂₆P3M peptide or the WT1₁₂₆P9V peptide. Even preferred is the WT1₁₈₇ peptide, the WT1₁₂₆ peptide, the WT1₁₈₇P2M peptide or the WT1₁₂₆P9V peptide. Particularly preferred is the WT1₁₈₇ peptide or the WT1₁₂₆ peptide.

A derivative of the WT1 peptide can also be used as the WT1 peptide. For example, the derivative of the WT1₁₈₇ or WT1₁₂₆ peptide may be formed of an amino acid sequence of the above-mentioned 9 contiguous amino acids and various substances bound to the N and/or C terminus thereof. The various substances may be, for example, amino acids, peptides, analogs thereof, etc. Such a substance bound to the WT1₁₈₇ peptide, the WT1₁₂₆ peptide or a modified peptide thereof undergoes, for example, in vivo enzyme treatment through intracellular processing etc., and finally the peptide consisting of the above-mentioned 9 amino acids is produced and presented as a complex with an HLA-A*0206 molecule on the cell surface. Thus, a WT1-specific CTL response can be induced in patients with HLA-A*0206.

The WT1 peptide can be prepared by a method usually used in the technical field, such as a peptide synthesis method described in Peptide Synthesis, Interscience, New York, 1966; The Proteins, Vol. 2, Academic Press Inc., New York, 1976; Peptide synthesis, Maruzen Co., Ltd., 1975; Basis and Experiments of Peptide Synthesis, Maruzen Co., Ltd. 1985; the Sequel to Development of Pharmaceuticals, Vol. 14 (peptide synthesis), Hirokawa Publishing Company, 1991; etc.

As a method of screening for the WT1 peptide and a modified peptide thereof, for example, a method involving conducting the IFNγ assay under single stimulation of, with a peptide, PBMCs (peripheral blood mononuclear cells) of some patients having HLA-A*0206, and then selecting a peptide showing a good response, is preferred because of simplicity.

In the present invention, polynucleotides, such as DNA encoding the above-mentioned WT1 protein or WT1 peptide immunogenic in HLA-A*0206-positive persons, can also be used as an active ingredient of the cancer vaccine composition. Namely, by inserting a polynucleotide encoding the WT1 protein or WT1 peptide into a suitable vector, preferably an expression vector, and then administering the vector into animals including humans, cancer immunity can be produced in the living body. Examples of the polynucleotide include DNA, RNA and the like, and preferred is DNA or RNA. The base sequence of the polynucleotide can be determined based on the amino acid sequence of the WT1 protein or WT1 peptide immunogenic in HLA-A*0206-positive persons. The polynucleotide can be prepared by a known DNA or RNA synthesis method, the PCR method, etc. Such a cancer vaccine composition for HLA-A*0206-positive persons, comprising DNA encoding the WT1 protein or WT1 peptide is also one aspect of the present invention. The WT1 protein or WT1 peptide is preferably a WT1 peptide, more preferably the $WT1_{187}$ peptide, the $WT1_{126}$ peptide or a modified peptide thereof, and most preferably the $WT1_{187}$ peptide or the $WT1_{126}$ peptide. The expression vector used to insert the above-mentioned DNA into is not particularly limited. RNA does not have to be inserted into a vector and can be used as it is as an active ingredient of the composition.

The cancer vaccine composition of the present invention can comprise an adjuvant. The adjuvant is not limited as long as, after administered together with or separately from the WT1 protein or WT1 peptide used as an antigen, it can nonspecifically enhance immunological responses to the antigen. Examples of the adjuvant include precipitating-type adjuvants and oily adjuvants. Examples of the precipitating-type adjuvant include sodium hydroxide, aluminum hydroxide, calcium phosphate, aluminum phosphate, alum, PEPES and carboxyvinyl polymers. A preferable oily adjuvant is one that can form micelles so that oil encloses an aqueous solution of an antigen. Specific examples thereof include liquid paraffin, lanolin, Freund, Montanide ISA-763AVG, Montanide ISA-51, incomplete Freund's adjuvant and complete Freund's adjuvant. These adjuvants can also be used as a mixture of two or more kinds thereof. Preferred is an oily adjuvant.

The amount of the adjuvant in the cancer vaccine composition of the present invention is not particularly limited as long as immunological responses to antigens can be nonspecifically enhanced. The amount thereof may be suitably selected depending on the kind of the adjuvant, etc.

The cancer vaccine composition of the present invention can be administered orally or parenterally (for example, intraperitoneally, subcutaneously, intracutaneously, intramuscularly, intravenously, intranasally, etc.). In the case of parenteral administration, an active ingredient, i.e., the WT1 protein or WT1 peptide, may also be percutaneously absorbed by applying the vaccine composition to the skin, or by attaching to the skin a patch containing the vaccine composition. The vaccine composition of the present invention can also be administered via inhaling etc. The vaccine composition is administered preferably parenterally, and more preferably intracutaneously or subcutaneously. The body part for intracutaneous or subcutaneous administration is preferably the upper arm etc., for example.

The cancer vaccine composition of the present invention can be in various dosage forms depending on its administration route, and exemplary dosage forms thereof include a solid preparation and a liquid preparation. The cancer vaccine composition may be, for example, in the form of a solid or liquid preparation to be used internally for oral administration, an injection for parenteral administration, or the like.

Examples of the solid preparation to be used internally for oral administration include tablets, pills, capsules, powders and granules.

For preparation of the solid preparation to be used internally, the WT1 protein or WT1 peptide is untreated, mixed with an additive, or granulated (according to, for example, stirring granulation, fluidized bed granulation, dry granulation, rolling stirring fluidized bed granulation, etc.), and then is subjected to a usual method. For example, the capsules can be prepared by encapsulation etc. and the tablets can be prepared by tableting etc. One or two kinds or more of the additives may be appropriately incorporated into the solid preparation. Examples of the additive include excipients such as lactose, mannitol, glucose, microcrystalline cellulose and corn starch; binders such as hydroxypropylcellulose, polyvinylpyrrolidone and magnesium aluminometasilicate; dispersing agents such as corn starch; disintegrators such as calcium carboxymethyl cellulose; lubricants such as magnesium stearate; solubilizing agents such as glutamic acid and aspartic acid; stabilizers; water soluble polymers including celluloses such as hydroxypropylcellulose, hydroxypropylmethylcellulose and methylcellulose, and synthetic polymers such as polyethylene glycol, polyvinylpyrrolidone and polyvinyl alcohol; and sweeteners such as white sugar, powder sugar, sucrose, fructose, glucose, lactose, reduced malt sugar syrup (maltitol syrup), reduced malt sugar syrup powder (maltitol syrup powder), high-glucose corn syrup, high-fructose corn syrup, honey, sorbitol, maltitol, mannitol, xylitol, erythritol, aspartame, saccharin and saccharin sodium.

The granules or tablets may be covered with a coating agent etc. if needed, and may be covered with two or more layers thereof. Examples of the coating agent include white sugar, gelatin, hydroxypropyl cellulose and hydroxypropylmethylcellulose phthalate. The capsules can be prepared by mixing the active ingredient with pranlukast hydrate and an excipient appropriately selected from the above excipients, optionally granulating the mixture, and optionally covering the resulting granules with a coating agent, followed by capsule filling. Alternatively, the capsules can be prepared by adding glycerol, sorbitol, etc. to an appropriate capsule base (gelatin etc.) to increase its plasticity, and encapsulating the active ingredient with the resulting base. To the capsule base may be added a colorant or a preservative (sulfur dioxide; and parabens such as methyl parahydroxybenzoate, ethyl parahydroxybenzoate and propyl parahydroxybenzoate) if needed. The capsules include hard capsules and soft capsules.

Examples of the liquid preparation to be used internally for oral administration include waters, suspensions/emulsions, syrups, preparations to be dissolved before use such as dry syrups, and elixirs. For preparation of the liquid preparation to be used internally, the WT1 protein or WT1 peptide is dissolved, suspended or emulsified in a diluent generally used for liquid preparations to be used internally. Examples of the diluent include purified water, ethanol and a mixture thereof. The liquid preparation may further contain a wetting agent, a suspending agent, an emulsifier, a sweetener, a flavoring, a fragrance, a preservative or a buffering agent. The dry syrups can be prepared, for example, by mixing the active ingredient with pranlukast hydrate and an additional ingredient such as white sugar, powder sugar, sucrose, fructose, glucose and lactose. The dry syrups may also be made into granules in a usual manner.

Examples of the dosage form for parenteral administration include injections, ointments, gels, creams, patches, aerosols and sprays. Preferred are injections. For example, the injection preferably contains a conventional carrier with the WT1 protein or WT1 peptide.

The injection for parenteral administration may be an aqueous injection or an oily injection. The aqueous injection can be prepared according to a known method, for example, by appropriately adding a pharmaceutically acceptable additive to an aqueous solvent (water for injection, purified water, etc.) to make a solution, mixing the WT1 protein or WT1 peptide with the solution, filter sterilizing the resulting mixture with a filter etc., and then filling an aseptic container with the resulting filtrate. Examples of the pharmaceutically acceptable additive include the above-mentioned adjuvants; isotonizing agents such as sodium chloride, potassium chloride, glycerol, mannitol, sorbitol, boric acid, borax, glucose and propylene glycol; buffering agents such as a phosphate buffer solution, an acetate buffer solution, a borate buffer solution, a carbonate buffer solution, a citrate buffer solution, a Tris buffer solution, a glutamate buffer solution and an epsilon-aminocaproate solution; preservatives such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edetate, boric acid and borax; thickeners such as hydroxyethylcellulose, hydroxypropylcellulose, polyvinyl alcohol and polyethylene glycol; stabilizers such as sodium hydrogen sulfite, sodium thiosulfate, sodium edetate, sodium citrate, ascorbic acid and dibutyl hydroxy toluene; and pH adjusters such as hydrochloric acid, sodium hydroxide, phosphoric acid and acetic acid. The injection may further contain an appropriate solubilizing agent, and examples thereof include alcohols such as ethanol; polyalcohols such as propylene glycol and polyethylene glycol; and non-ionic surfactants such as polysorbate 80, polyoxyethylene hydrogenated castor oil 50, lysolecithin and pluronic polyols. Also, proteins such as bovine serum albumin and keyhole limpet hemocyanin; polysaccharides such as aminodextran; etc. may be contained in the injection. For preparation of the oily injection, for example, sesame oil or soybean oil is used as an oily solvent, and benzyl benzoate or benzyl alcohol may be blended as a solubilizing agent. The prepared injection is usually stored in an appropriate ampule, vial, etc. The liquid preparations, such as injections, can also be deprived of moisture and preserved by cryopreservation or lyophilization. The lyophilized preparations become ready to use by redissolving them in added distilled water for injection etc. just before use.

Another dosage form of the cancer vaccine composition of the present invention may be a liposome containing the WT1 protein or WT1 peptide and, if needed, polysaccharides and/or other ingredients that can be blended into the cancer vaccine composition.

The dose of the cancer vaccine composition of the present invention varies with the kind of the WT1 protein, WT1 peptide or DNA to be used, the age and body weight of the patient, the disease to be treated, etc. For example, in the case of the vaccine composition comprising the WT1 peptide, for example the $WT1_{187}$ peptide or the $WT1_{126}$ peptide, the daily dose is preferably about 0.1 µg/kg bw to 1 mg/kg bw as the amount of the WT1 peptide. The dose of the WT1 peptide is usually 0.0001 mg to 1000 mg, preferably 0.01 mg to 1000 mg, and more preferably 0.1 mg to 10 mg. This amount is preferably administered once in several days to several months.

The cancer vaccine composition of the present invention is a cancer vaccine composition for HLA-A*0206-positive persons. The HLA type, which is a measure for selecting HLA-A*0206-positive persons, can be determined from, for example, donors' peripheral blood. Examples of the method of determining the HLA type include known methods, such as the DNA typing method, for example, the SBT (Sequencing Based Typing) method or the SSP method, and the HLA typing method. In the SBT method, the base sequence of a PCR-amplified DNA is compared with the base sequence data of the known alleles to precisely identify the HLA gene type. In the SSP method, after PCR amplification using a variety of primers specific to respective HLA alleles, subsequent electrophoresis is performed to check a positive band. Thus, the HLA gene type can be identified.

When the cancer vaccine composition of the present invention has been administered into an HLA-A*0206-positive person, the HLA-A*0206-restricted WT1 protein or WT1 peptide in the vaccine composition, or the WT1 protein or WT1 peptide expressed from DNA or RNA in the vaccine composition binds to an HLA-A*0206 molecule on the surface of an antigen presenting cell (dendritic cell) of the HLA-A*0206-positive person. This induces specific antitumor immunity, i.e., WT1-specific CTLs, which destroy cancer cells in the subject (HLA-A*0206-positive person). Such antitumor immunity can be checked, for example by the WT1-specific CTL response, the cytotoxicity test against cancer cells (for example, $^{51}Cr$ release cytotoxicity test), etc. For example, the HLA-A*0201-restricted $WT1_{187}$ peptide and $WT1_{126}$ peptide each consisting of 9 amino acids derived from the WT1 protein, which have been reported to be capable of inducing a WT1-specific CTL response, can induce an HLA-A*0206-restricted response. About 17% of Japanese people are HLA-A*0206-positive, while almost the same proportion are HLA-A*0201-positive. In the following Examples 1 to 5, $WT1_{187}$ peptide-specific CTLs were prepared from PBMCs of three HLA-A*0206-positive blood donors. The induced CTLs showed the cytotoxic effect on WT1-expressing, HLA-A*0206-positive leukemia cells. Since $WT1_{187}$ peptide- and $WT1_{126}$ peptide-specific CTL activity can be inhibited by an anti-HLA class I antibody, the activity is found to be exhibited by HLA class I-restricted CTLs. The WT1 protein or WT1 peptide including the $WT1_{187}$ peptide and/or the $WT1_{126}$ peptide, or a modified peptide thereof can be a vaccine for HLA-A*0206-positive cancer patients as well as HLA-A*0201-positive cancer patients. Therefore, the immunotherapy based on the WT1 protein or WT1 peptide for patients with malignant tumors, such as hematopoietic tumors and solid cancers, can be applied further to HLA-A*0206-positive cancer patients. The method of cancer treatment and/or prevention in HLA-A*0206-positive persons, comprising administering the cancer vaccine composition of the present invention into an HLA-A*0206-positive person, is one of preferable embodiments of the present invention.

In HLA-A*0206-positive persons, the cancer vaccine composition of the present invention can be used for treatment and/or prevention of cancers accompanied by increased expression of the WT1 gene: for example, hematopoietic tumors such as leukemia, myelodysplastic syndrome, multiple myeloma and malignant lymphoma; and solid cancers such as gastric cancer, colon cancer, lung cancer, breast cancer, germ cell cancer, hepatic cancer, skin cancer, bladder cancer, prostate cancer, uterine cancer, cervical cancer and ovarian cancer.

An exemplary administration method of the cancer vaccine composition of the present invention is a method comprising collecting PBMCs from peripheral blood of an HLA-A*0206-positive patient, extracting dendritic cells from the PBMCs, pulsing the dendritic cells with a peptide, for example the $WT1_{187}$ peptide or the $WT1_{126}$ peptide, or a polynucleotide, for example DNA or RNA, contained as an active ingredient in the cancer vaccine composition of the present invention, and returning the dendritic cells to the patient via subcutaneous administration etc. The conditions for pulsing dendritic cells with the WT1 peptide etc. are not particularly limited as long as the effect of the present invention is achieved, and may be ordinary conditions.

In the case where RNA encoding the WT1 protein or WT1 peptide is used for the cancer vaccine composition, it is preferable that the composition is administered so that the RNA is introduced into dendritic cells of an HLA-A*0206-positive person. An exemplary method for introducing RNA into dendritic cells of an HLA-A*0206-positive person is a method comprising collecting dendritic cells from an HLA-A*0206-positive person in the same manner as mentioned above, and introducing RNA into the dendritic cells with an electric pulse. The WT1 protein or WT1 peptide expressed from the introduced RNA in the dendritic cells is allowed to be presented on the surface thereof. By returning the dendritic cells pulsed with the RNA into the HLA-A*0206-positive person, cancer immunity can be quickly produced in the living body. Such a method of cancer treatment or prevention, comprising introducing RNA encoding the WT1 protein or WT1 peptide into dendritic cells of an HLA-A*0206-positive person, is one of preferable embodiments of the present invention.

Another embodiment of the present invention relates to a method for inducing WT1-specific CTLs, by culturing, in the presence of the WT1 protein or WT1 peptide, PBMCs derived from an HLA-A*0206-positive person, to obtain WT1-specific CTLs induced therefrom. The subject from which PBMCs are derived is not particularly limited as long as the subject is HLA-A*0206-positive. Examples of the WT1 protein or WT1 peptide include the $WT1_{187}$ peptide, the $WT1_{126}$ peptide and a modified peptide thereof, and preferably the $WT1_{187}$ peptide and the $WT1_{126}$ peptide. For example, WT1-specific CTLs can be induced from CTL precursor cells among PBMCs by culturing PBMCs derived from an HLA-A*0206-positive person in the presence of the $WT1_{187}$ peptide (or $WT1_{126}$ Peptide). The culture conditions for PBMCs derived from an HLA-A*0206-positive person is not particularly limited, and may be ordinary conditions. The thus-obtained CTLs recognize a complex of the $WT1_{187}$ peptide (or the $WT1_{126}$ peptide) and an HLA-A*0206 molecule. Therefore, by use of WT1-specific CTLs induced according to the present invention, WT1-highly-expressing tumor cells can be specifically destroyed in an HLA-A*0206-positive person, and thereby hematopoietic tumors and solid cancers in the subject, i.e., an HLA-A*0206-positive person, can be treated and/or prevented. The method for administering such WT1-specific CTLs into an HLA-A*0206-positive subject is not particularly limited, and for example, may be the same as the administration method of the above-mentioned cancer vaccine composition.

Another embodiment of the present invention relates to a kit for inducing WT1-specific CTLs, comprising the HLA-A*0206-restricted WT1 protein or WT1 peptide as an essential constituent. Preferably, the kit is used for the above-mentioned method for inducing WT1-specific CTLs derived from an HLA-A*0206-positive person. Such a kit may comprise, for example, a means for collecting PBMCs, an adjuvant and a reaction container in addition to the HLA-A*0206-restricted WT1 protein or WT1 peptide. By use of the kit, WT1-specific CTLs that recognize a complex of a cancer antigen, such as the $WT1_{187}$ peptide and the $WT1_{126}$ peptide, and an HLA-A*0206 molecule can be efficiently induced.

Another embodiment of the present invention relates to a method for inducing dendritic cells that present the WT1 protein or WT1 peptide, by culturing, in the presence of the WT1 protein or WT1 peptide, immature dendritic cells derived from an HLA-A*0206-positive person, to obtain dendritic cells induced therefrom which present the WT1 protein or WT1 peptide. Examples of the WT1 protein or WT1 peptide include the $WT1_{187}$ peptide, the $WT1_{126}$ peptide and a modified peptide thereof, and preferably the $WT1_{187}$ peptide and the $WT1_{126}$ peptide. The subject from which immature dendritic cells are derived is not particularly limited as long as the subject is HLA-A*0206-positive. Since immature dendritic cells are present among PBMCs etc., PBMCs may also be cultured in the presence of the $WT1_{187}$ peptide or the $WT1_{126}$ peptide, for example. By administration of the thus-obtained dendritic cells to an HLA-A*0206-positive person, the above-mentioned WT1-specific CTLs are efficiently induced, and thereby hematopoietic tumors and solid cancers in the subject can be treated and/or prevented. The method for administering such dendritic cells into an HLA-A*0206-positive subject is not particularly limited, and for example, may be the same as the administration method of the above-mentioned cancer vaccine composition.

Another embodiment of the present invention relates to a kit for inducing dendritic cells that present the WT1 protein or WT1 peptide, comprising the HLA-A*0206-restricted WT1 protein or WT1 peptide as an essential constituent. Preferably, the kit is used for the above-mentioned method for inducing dendritic cells. Such a kit may comprise, for example, a means for collecting immature dendritic cells and PBMCs, an adjuvant and a reaction container in addition to the HLA-A*0206-restricted WT1 protein or WT1 peptide. By use of the kit, dendritic cells that present the WT1 protein or WT1 peptide via an HLA-A*0206 molecule can be efficiently induced.

Cancers in HLA-A*0206-positive persons can be diagnosed by use of
(1) the WT1 protein or WT1 peptide, WT1-specific CTLs induced by the above-mentioned method, or dendritic cells induced by the above-mentioned method, or
(2) an antibody against the following: the WT1 protein or WT1 peptide, WT1-specific CTLs induced by the above-mentioned method, or dendritic cells induced by the above-mentioned method.

Such a method of cancer diagnosis is also one aspect of the present invention. In the above (1), cancer diagnosis is conducted preferably using WT1-specific CTLs induced by above-mentioned method. Examples of the WT1 protein or WT1 peptide include the $WT1_{187}$ peptide, the $WT1_{126}$ peptide and a modified peptide thereof, and preferably the $WT1_{187}$ peptide and the $WT1_{126}$ peptide.

According to the present invention, an exemplary method of cancer diagnosis for HLA-A*0206-positive persons comprises a step of detecting or quantifying the WT1 protein or WT1 peptide, an antibody thereagainst or WT1-specific CTLs in a sample from an HLA-A*0206-positive person, and a step of comparing the amount of the protein or a partial peptide thereof, an antibody thereagainst or the WT1-specific CTLs, with that in the case where cancer is not developed.

In a cancer patient sample (for example, blood), the WT1 peptide and/or WT1 protein released from cancer cells is present, and the immunological response against a cancer antigen is enhanced. That is, the cancer patient sample has an increased amount of an antibody against the WT1 peptide or WT1 protein, WT1-specific CTLs, etc. For this reason, when the amount of the WT1 peptide or WT1 protein, an antibody thereagainst or the WT1-specific CTLs in the sample is increased compared with that in the case where cancer is not developed, cancer may have been developed. The amount of the antibody can be measured by the ELISA method, for example. The WT1-specific CTLs can be detected by a method using WT1 multimers such as MHC tetramers described below.

Alternatively, cancer diagnosis can also be performed by incubating the above-mentioned CTLs, dendritic cells or antibody together with a sample from an HLA-A*0206-positive subject, or administering the above-mentioned CTLs, dendritic cells or antibody into an HLA-A*0206-positive subject; and then determining the position, region, amount, etc. of the CTLs, dendritic cells or antibody. Since CTLs and dendritic cells have a property to gather around cancer cells, cancer diagnosis can be performed by administering the CTLs or dendritic cells into the subject, and examining the position or region thereof. A method of cancer diagnosis for HLA-A*0206-positive persons, comprising a step of administering WT1-specific CTLs or dendritic cells induced by the above-mentioned method into an HLA-A*0206-positive subject, and a step of determining the position or region of the CTLs or dendritic cells in the HLA-A*0206-positive subject is also one aspect of the present invention.

Cancer diagnosis can also be performed by incubating CTLs or dendritic cells together with a sample from an HLA-A*0206-positive subject to allow them to react, adding an antibody against the CTLs or dendritic cells, continuing incubation, and detecting or quantifying an antibody-bound complex of the cancer cell and CTLs, antibody-bound dendritic cells, etc. via a label etc. bound to the antibody. When the amount of the antibody-bound complex of the cancer cell and CTLs or the antibody-bound dendritic cells is increased compared with that in the case where cancer is not developed, cancer may have been developed. The above-mentioned CTLs, dendritic cells or antibody may be labeled. The labeling enables the diagnosis to be efficiently performed. Examples of the sample from an HLA-A*0206-positive subject include biological specimens obtained from HLA-A*0206-positive persons, such as urine, blood, tissue extract fluid, saliva, tear and other body fluids, and blood is preferable.

Examples of the method of cancer diagnosis for HLA-A*0206-positive persons using the above-mentioned WT1 protein or WT1 peptide include the MHC tetramer assay, the MHC pentamer assay and the MHC dextramer assay, each of which uses the WT1 peptide as an antigen. For example, in the MHC tetramer assay or MHC pentamer assay using the $WT1_{187}$ peptide or $WT1_{126}$ peptide as an antigen peptide, WT1-specific CTLs in HLA-A*0206-positive persons can be detected by use of an MHC/$WT1_{187}$ peptide complex or an MHC/$WT1_{126}$ peptide complex as a probe. Since cancer patients show high expression of WT1-specific CTLs, cancer can be diagnosed by measuring the expression of WT1-specific CTLs in HLA-A*0206-positive persons. Since cancer patients manifest an enhanced immunological response against cancer antigens, cancer can be diagnosed also by examining immunological response against the WT1 protein or WT1 peptide in HLA-A*0206-positive persons. Examples of the method of examining immunological response include a method involving measuring an antibody against the WT1 protein or WT1 peptide by ELISA. Such a method of cancer diagnosis for HLA-A*0206-positive persons using a protein product of the tumor suppressor gene WT1 or a partial peptide thereof is also one aspect of the present invention. The MHC tetramer assay and MHC pentamer assay can be performed by a known method using a commercially available kit, for example, "WT1 tetramer" (Medical & Biological Laboratories, Co., Ltd.).

Cancer diagnosis for HLA-A*0206-positive persons can also be performed by a method comprising a step of reacting a sample from an HLA-A*0206-positive subject with an antibody against the following: the WT1 protein or WT1 peptide, WT1-specific CTLs induced by the above-mentioned method or dendritic cells induced by the above-mentioned, and a step of detecting or quantifying a complex of the antibody with the WT1 protein or WT1 peptide, or a complex of the antibody with WT1-specific CTLs or dendritic cells. When the amount of the complex of the antibody with the WT1 protein or WT1 peptide, or the complex of the antibody with WT1-specific CTLs or dendritic cells is increased compared with that in the case where cancer is not developed, cancer may have been developed.

Examples of the antibody against dendritic cells include an antibody which recognizes a WT1 peptide/HLA-A*0206 complex. Since such an antibody can recognize the WT1 peptide and an HLA-A*0206 molecule, the antibody can recognize dendritic cells having the WT1 peptide presented via HLA Class I.

An antibody which recognizes a complex of WT1 peptide/HLA-A*0206/TCR (T cell antigen receptor) of CTLs can also be used as the antibody against dendritic cells. Such an antibody can recognize a complex of a dendritic cell and a CTL, and a complex of a cancer cell and a CTL.

Cancer diagnosis can be performed by incubating such an antibody together with a sample from an HLA-A*0206-positive subject to allow them to form a complex, and detecting or quantifying an antibody-bound complex of the cancer cell and CTLs, antibody-bound dendritic cells presenting the WT1 peptide, or the like via the fluorescence emitted by the antibody. When the amount of the antibody-bound complex of the cancer cell and CTLs, the antibody-bound dendritic cells presenting the WT peptide, or the like is increased compared with that in the case where cancer is not developed, cancer may have been developed.

A method of cancer treatment or prevention, comprising administering a composition containing the WT1 protein or WT1 peptide into an HLA-A*0206-positive person, is also one aspect of the present invention. The composition comprising the WT1 protein or WT1 peptide and preferable embodiments thereof are the same as described regarding the above-mentioned cancer vaccine composition.

Use of the WT1 protein or WT1 peptide for cancer treatment or prevention in HLA-A*0206-positive persons, and use thereof for production of a cancer vaccine composition used for cancer treatment or prevention in HLA-A*0206-positive persons is also one aspect of the present invention. The WT1 protein or WT1 peptide and preferable embodiments thereof are the same as described regarding the above-mentioned cancer vaccine composition.

A cancer vaccine composition for HLA-A*0201-positive persons, comprising a modified peptide of the $WT1_{187}$ peptide (SEQ ID NO: 2) or the $WT1_{126}$ peptide (SEQ ID NO: 3), either of which is a partial peptide of a protein product of the tumor suppressor gene WT1, the modified peptide being immunogenic in HLA-A*0201-positive persons, is also one aspect of the present invention.

Examples of a modified WT1$_{187}$ peptide or a modified WT1$_{126}$ peptide include peptides comprising deletion, substitution or addition of one or several amino acids of the above-mentioned WT1$_{187}$ peptide or WT1$_{126}$ peptide. The modified WT1$_{187}$ peptide is preferably a peptide comprising the same amino acid residues at positions 4 to 8 from the N terminus as the WT1$_{187}$ peptide has at the corresponding positions. As such a modified peptide, preferred are the above-mentioned peptides of SEQ ID NOS: 4 to 12, 15 and 16, 18 to 20 and 22 to 25. The WT1$_{187}$P9L peptide (SLGEQQYSL; SEQ ID NO: 53) is also preferred. The modified WT1$_{126}$ peptide is preferably a peptide comprising the same amino acid residues at positions 4 to 8 from the N terminus as the WT1$_{126}$ peptide has at the corresponding positions. For example, preferred are the above-mentioned peptides of SEQ ID NOS: 27 to 37 and 39 to 52.

In yet another preferable embodiment of the present invention, the above-mentioned peptides of SEQ ID NOS: 4 to 26 and 53 to 62 may be used as a modified WT1$_{187}$ peptide, and the above-mentioned peptides of SEQ ID NOS: 27 to 52 and 63 to 75 may be used as a modified WT1$_{126}$ peptide. Among the modified peptides of SEQ ID NOS: 4 to 75, the peptides except the WT1$_{187}$P1D peptide, the WT1$_{187}$P1E peptide, the WT1$_{187}$P1H peptide, the WT1$_{187}$P1P peptide and the WT1$_{187}$P2Q peptide; and the WT1$_{126}$P1D peptide, the WT1$_{126}$P1E peptide, the WT1$_{126}$P1P peptide, the WT1$_{126}$P2A peptide and the WT1$_{126}$P2Q peptide are preferred.

Inter alia, the modified WT1$_{187}$ peptide is preferably the WT1$_{187}$P1F peptide, the WT1$_{187}$P2M peptide or the WT1$_{187}$P3M peptide, and more preferably the WT1$_{187}$P1F peptide or the WT1$_{187}$P2M peptide. The modified WT1$_{126}$ peptide is preferably the WT1$_{126}$P1F peptide, the WT1$_{126}$P2L peptide, the WT1$_{126}$P3M peptide or the WT1$_{126}$P9V peptide, and more preferably the WT1$_{126}$P1F peptide or the WT1$_{126}$P2L peptide.

The amount for use of the modified WT1$_{187}$ peptide or WT1$_{126}$ peptide which is immunogenic in HLA-A*0201-positive persons is the same as that of the WT1 peptide in the above-mentioned cancer vaccine composition for HLA-A*0206-positive persons. The other ingredients of the cancer vaccine composition for HLA-A*0201-positive persons and preferable embodiments thereof are the same as those of the above-mentioned vaccine composition for HLA-A*0206-positive persons.

DNA and RNA encoding the above-mentioned modified WT1$_{187}$ peptide or WT1$_{126}$ peptide which is immunogenic in HLA-A*0201-positive persons can also be used as an active ingredient of the cancer vaccine composition for HLA-A*0201-positive persons. Such a cancer vaccine composition for HLA-A*0201-positive persons is also one aspect of the present invention.

The other ingredients than the above-mentioned DNA and RNA in the cancer vaccine composition for HLA-A*0201-positive persons and preferable embodiments thereof are the same as those of the above-mentioned cancer vaccine composition for HLA-A*0206-positive persons.

WT1-specific CTLs can be induced from PBMCs derived from an HLA-A*0201-positive person by culturing the PBMCs in the presence of the modified WT1$_{187}$ peptide or WT1$_{126}$ peptide which is immunogenic in the above-mentioned HLA-A*0201-positive person. Such a method of inducing WT1-specific CTLs is also one aspect of the present invention.

Preferable examples of the modified WT1$_{187}$ peptide or WT1$_{126}$ peptide which is immunogenic in HLA-A*0201-positive persons are the same as used for the above-mentioned cancer vaccine composition for HLA-A*0201-positive persons.

Dendritic cells that present the modified WT1$_{187}$ peptide or WT1$_{126}$ peptide can be induced from immature dendritic cells derived from an HLA-A*0201-positive person by culturing the immature dendritic cells in the presence of the modified peptide which is immunogenic in the above-mentioned HLA-A*0201-positive person. Such a method for inducing dendritic cells that present the modified WT1$_{187}$ peptide or WT1$_{126}$ peptide is also one aspect of the present invention. Preferable examples of the modified peptide are the same as used for the above-mentioned cancer vaccine composition for HLA-A*0201-positive persons.

Cancers in HLA-A*0201-positive persons can be diagnosed by use of the above-mentioned modified WT1$_{187}$ peptide or modified WT1$_{126}$ peptide immunogenic in HLA-A*0201-positive persons, an antibody thereagainst, WT1-specific CTLs induced by the modified peptide or dendritic cells induced by the modified peptide. Such a method of cancer diagnosis for HLA-A*0201-positive persons is also one aspect of the present invention. The method of cancer diagnosis for HLA-A*0201-positive persons and preferable embodiments thereof are the same as the above-mentioned method of cancer diagnosis for HLA-A*0206-positive persons and preferable embodiments thereof.

Examples of the method of cancer diagnosis for HLA-A*0201-positive persons include the MHC tetramer assay, the MHC pentamer assay and the MHC dextramer assay, each of which uses the modified WT1$_{187}$ peptide or modified WT1$_{126}$ peptide immunogenic in HLA-A*0201-positive persons as an antigen. Preferable examples of the modified peptide are the same as used for the above-mentioned cancer vaccine composition for HLA-A*0201-positive persons.

Cancers in HLA-A*0201-positive persons can be diagnosed by use of an antibody against the following: the above-mentioned modified WT1$_{187}$ peptide or modified WT1$_{126}$ peptide immunogenic in HLA-A*0201-positive persons, WT1-specific CTLs induced by the modified peptide or dendritic cells induced by the modified peptide. Such a method of cancer diagnosis for HLA-A*0201-positive persons is also one aspect of the present invention. Preferable examples of the modified peptide are the same as used for the above-mentioned cancer vaccine composition for HLA-A*0201-positive persons. The method of cancer diagnosis for HLA-A*0201-positive persons and preferable embodiments thereof are the same as the above-mentioned method of cancer diagnosis for HLA-A*0206-positive persons and preferable embodiments thereof.

A method of cancer treatment or prevention, comprising administering an HLA-A*0201-positive person a cancer vaccine composition containing the following peptide:
a modified peptide of the WT1$_{187}$ peptide (SEQ ID NO: 2) or the WT1$_{126}$ peptide (SEQ ID NO: 3), either of which is a partial peptide of a protein product of the tumor suppressor gene WT1, the modified peptide being immunogenic in HLA-A*0201-positive persons,
is also one aspect of the present invention.

Preferable examples of the modified peptide are the same as used for the above-mentioned cancer vaccine composition for HLA-A*0201-positive persons. The cancer vaccine composition and preferable embodiments thereof are the same as described regarding the above-mentioned vaccine composition for HLA-A*0201-positive persons.

The present invention relates to use of the following peptide:

a modified peptide of the WT1$_{187}$ peptide (SEQ ID NO: 2) or the WT1$_{126}$ peptide (SEQ ID NO: 3), either of which is a partial peptide of a protein product of the tumor suppressor gene WT1, the modified peptide being immunogenic in an HLA-A*0201-positive person, for cancer treatment or prevention in HLA-A*0201-positive persons, and use thereof for production of a cancer vaccine composition used for cancer treatment or prevention in HLA-A*0201-positive persons.

Preferable examples of the modified peptide are the same as used for the above-mentioned cancer vaccine composition for HLA-A*0201-positive persons. The cancer vaccine composition and preferable embodiments thereof are the same as described regarding the above-mentioned vaccine composition for HLA-A*0201-positive persons.

EXAMPLES

Hereinafter, the present invention will be illustrated in more detail by way of examples, but is not limited thereto. Abbreviations in Examples indicate the following meanings. Synthetic peptides were purchased from SIGMA GENOSYS JAPAN.
DCs: Dendritic cells
PBMCs: Peripheral blood mononuclear cells
CD: Cluster of Differentiation (leukocyte differentiation antigen)
GM-CSF: Granulocyte monocyte colony stimulating factor
IL: Interleukin
TNFα: Tumor necrosis factor-α
PGE: Prostaglandin
Gy: Gray
B-LCLs: B-lymphoblastoid cell line
EB virus: Epstein-Barr virus
tBu: t-butyl
Trt: Triphenylmethyl
Fmoc: 9-fluorenylmethyloxycarbonyl Example 1

Prediction of HLA Molecules Capable of Binding with the WT1 Peptide

HLA molecules capable of binding with the WT1$_{187}$ peptide (SEQ ID NO: 2) were predicted using the NetMHC2.0 Server-prediction program.

As a result, the HLA-A*0201-restricted WT1$_{187}$ peptide capable of inducing WT1-specific CTLs was ranked high in terms of binding affinity to an HLA-A*0206 molecule in the NetMHC2.0 Server-prediction program.

Example 2

Preparation of WT1$_{187}$ Peptide-Specific CTLs from PBMCs of HLA-A*0206-Positive Healthy Blood Donors, and Cytotoxicity Test of the CTLs (1) Separation of PBMCs of HLA-A*0206-Positive Healthy Blood Donors, and Preparation of DCs First, PBMCs were isolated from peripheral blood of each of HLA-A*0206 healthy blood donors (three persons) by Ficoll-Hypaque density gradient centrifugation. Then, CD14-positive cells were selected from the PBMCs using anti-human CD14 Magnetic Particles-DM (manufactured by Becton, Dickinson and company (BD)). In this case, it was considered that a large number of CD14-positive cells are present in the monocyte population. The selected CD14-positive cells were cultured in an X-VIVO15 medium (manufactured by BioWhittaker, Walkersville, Md.) supplemented with 1 v/v % human AB serum, 800 IU/mL GM-CSF (manufactured by Pepro Tech INC, Rocky Hill, N.J.) and 1000 IU/mL IL-4 (manufactured by Pepro Tech INC) to prepare DCs.

(2) Induction of Autologous Mature DCs

The DCs prepared in the above (1) were cultured at 37° C. for 1 day, and then a maturation cytokine cocktail containing 10 ng/mL TNFα (tumor necrosis factor-α; Pepro Tech INC, Rocky Hill, N.J.), 10 ng/mL IL-β, 1000 IU/mL IL-6 and 1 μg/mL PGE2 was added to culture wells containing the DCs. After 24 hour-culture at 37° C., autologous mature DCs were obtained.

(3) Induction of WT1$_{187}$ Peptide-Specific CTLs

The autologous mature DCs were pulsed with the WT1$_{187}$ peptide, irradiated with 30 Gy of radiation, and co-cultured with CD8-positive T cell-enriched PBMCs obtained from the HLA-A*0206-positive healthy blood donor. The pulsing of the DCs with the WT1$_{187}$ peptide was performed by culturing the DCs in the presence of 10 μg/mL of the WT1$_{187}$ peptide at 37° C. for 30 minutes. The CD8-positive T cells were enriched from PBMCs of the HLA-A*0206-positive healthy blood donor using CD8 MicroBeads and MS column (manufactured by Miltenyi Biotec GmbH).

From the second stimulation, autologous PBMCs which had been pulsed with the peptide and then irradiated with radiation were used as selective stimulator cells. Two days after the second stimulation, recombinant IL-2 (provided by Shionogi & Co., Ltd.) and IL-7 (manufactured by Pepro Tech INC) were added to the culture medium at the concentrations of 10 IU/mL and 10 ng/mL, respectively. After the 4th stimulation, the cells were cultured for 10 days at 37° C. and then the resulting cells (CTLs) were collected by centrifugation using a centrifuge. The cytotoxic activity of these cells (CTLs) against target cells was examined by a $^{51}$Cr release cytotoxicity test.

(4) Cytotoxicity Test

The cytotoxicity test was performed by a $^{51}$Cr release cytotoxicity test. The $^{51}$Cr release cytotoxicity test was performed as follows. First, target cells (1×10$^7$ cells/mL) were incubated in the presence of 100 μL of $^{51}$Cr (specific activity: 1 mCi/mi) in RPMI1640 (manufactured by NIHON PHARMACEUTICAL CO., LTD.) supplemented with 10% fetal bovine serum at 37° C. for 1.5 hours to label the target cells with $^{51}$Cr. Then, the $^{51}$Cr-labeled target cells were added to wells of 96 round-bottom well plates containing various numbers of CTLs obtained in the above (3) (suspended in 100 μL of an assay medium), mixed with the CTLs and then incubated at 37° C. for 4 hours. These cells were mixed so that the E/T ratio (cell number ratio) was 1:1, 5:1, 20:1 or 25:1, with the proviso that CTLs and the $^{51}$Cr-labeled target cells are expressed as "E" and "T", respectively. After the completion of incubation, 100 μL of the supernatant was collected from each well. The amount of $^{51}$Cr release from the labeled cells was determined, and the specific lysis (%) based on the $^{51}$Cr release was calculated. The specific lysis (%) was calculated in the following manner.

Specific lysis (%)=(release from a test sample−spontaneous release)/(maximum release−spontaneous release)×100

In the formula, the amount of spontaneous release refers to the amount of fluorescence of culture supernatant in the wells containing target cells only, and the maximum release refers to the amount of fluorescence of culture medium in which the target cells have been completely lysed by treatment with 1 mass % Triton X-100.

The target cells to be used were B-LCLs, K562 cells, JY cells, and KH88 cells, which will be described in detail below. KH88 cells are the same as KH88OF8 cells used in the following Example 9.

B-LCLs, which were established by EB virus-mediated transformation of peripheral blood B lymphocytes obtained from an HLA-A*0206-positive blood donor, do not express WT1.

K562 cells, which were established from a patient with chronic myelogenous leukemia in blastic crisis, are a WT1-expressing, non-HLA class I-expressing cell line. The present inventor was not able to obtain a WT1-expressing, HLA-A*0206-positive wild-type leukemia cell line. For this reason, 0206K562 cells, which were prepared by transformation of K562 cells with HLA-A*0206 genes, were also used. The FACS analysis using an anti-HLA-A2 antibody (cloneBB7.2; manufactured by BD Biosciences Pharmingen) showed that the 0206K562 cells transformed with HLA-A*0206 genes express HLA-A*0206 molecules on the cell surfaces.

The western blot analysis showed that B-LCL cells transformed with the WT1 gene express WT1. B-LCL cells transformed with a mock vector were used as a control.

JY cells are a non-WT1-expressing, HLA-A*0206-negative B cell line established by EB virus-mediated transformation.

KH88 cells are a WT1-expressing, HLA-A*0206-negative leukemia cell line.

Each cell line was cultured in a RPMI1640 culture medium supplemented with 10 v/v % heat-inactivated fetal bovine serum, 50 IU/mL penicillin and 50 mg/mL streptomycin.

(5) Antibody and Flow Cytometry Analysis

Anti-human CD14, CD86, CD80, CD83 and HLA-DR mAbs were purchased from BD. Concentration and maturation of DCs were confirmed by analysis of cell surface antigens using the monoclonal antibodies (mAbs) listed above. Samples were analyzed with a flow cytometer (FACS Calibur; manufactured by BD) using CellQest software.

(6) Results

Figure 2:
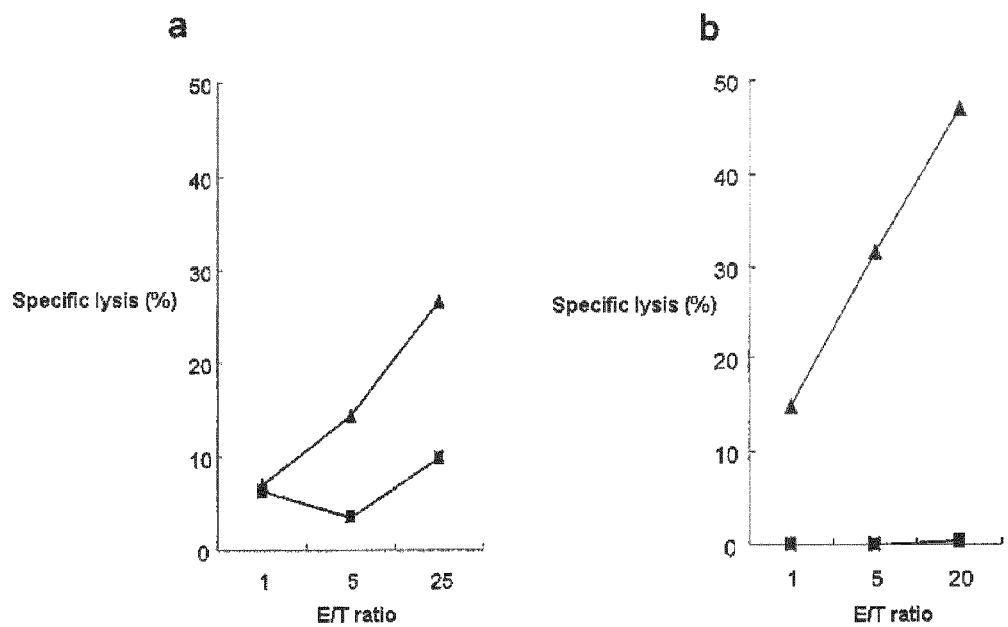
FIG. 2 shows the cytotoxic activity of $WT1_{187}$ peptide-specific CTLs induced from PBMCs of an HLA-A*0206-positive healthy blood donor.

It was examined whether $WT1_{187}$ peptide-specific CTLs can be prepared from PBMCs of HLA-A*0206-positive blood donors. The $WT1_{187}$ peptide-specific cytotoxic activity was examined using the CTLs obtained by repeatedly stimulating the CD8-positive T cell-enriched PBMCs from the HLA-A*0206-positive healthy blood donor with $WT1_{187}$ peptide-pulsed autologous DCs or PBMCs. The CTLs showed a stronger cytotoxic activity against $WT1_{187}$ peptide-pulsed autologous B-LCL cells than against non-$WT1_{187}$ peptide-pulsed B-LCL cells (FIG. 1a). In FIG. 1a, the vertical axis represents the cytotoxic activity, and the horizontal axis represents the ratio of CTLs obtained by peptide stimulation (effector: E) relative to target cells (target: T) (E/T ratio). The closed triangle represents the cells pulsed with 10 µg/mL of the $WT1_{187}$ peptide, and the closed square represents the cells not pulsed with the $WT1_{187}$ peptide. The same cytotoxic activity as above was shown also by the CTLs similarly prepared from the PBMCs isolated from the two different HLA-A*0206-positive healthy blood donors (FIGS. 2a and 2b). In FIG. 2, the closed triangle represents the cells pulsed with 10 µg/mL of the $WT1_{187}$ peptide, and the closed square represents the cells not pulsed with the $WT1_{187}$ peptide. These results show that each cytotoxic activity is specific to the $WT1_{187}$ peptide.

The cytotoxic activity of the CTLs increased in parallel with the concentration of the $WT1_{187}$ peptide used to pulse the DCs or PBMCs with, and reached the plateau at the peptide concentration of 0.1 µg/mL (FIG. 1b). The half maximum concentration of the $WT1_{187}$ peptide for specific lysis (half-maximal lysis value) was about $5 \times 10^{-5}$ µg/mL. This shows that the affinity of TCRs (T cell antigen receptors) of the CTLs to a $WT1_{187}$ peptide/HLA-A*0206 complex was relatively high. This result strongly suggests that CTLs induced with the $WT1_{187}$ peptide can recognize the $WT1_{187}$ peptide.

Figure 3:
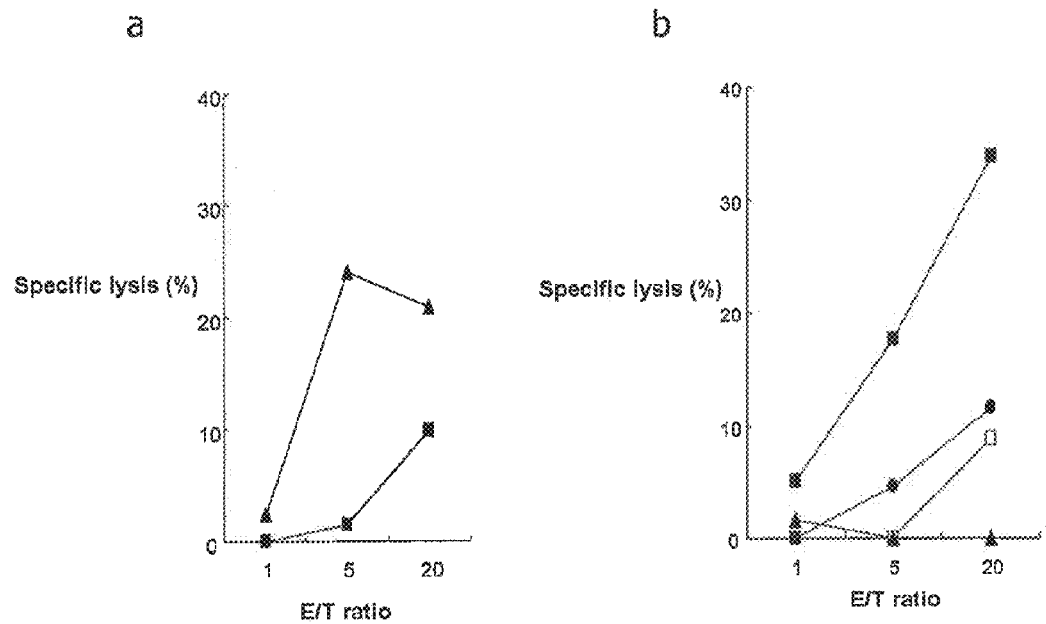
FIG. 3a shows the cytotoxic activity of $WT1_{187}$ peptide-specific CTLs against B-LCLs transformed with the WT1 gene, or B-LCLs transformed with a mock vector.
FIG. 3b shows the cytotoxic activity of $WT1_{187}$ peptide-specific CTLs against 0206K562 cells, K562 cells, KH88 cells or JY cells.

In the same manner as above, the cytotoxic activity against various target cells endogenously expressing WT1 was examined using the CTLs obtained by stimulating the CD8-positive T cell-enriched PBMCs from the HLA-A*0206-positive blood donor with $WT1_{187}$ peptide-pulsed DCs or PBMCs. The results are shown in FIGS. 3a and 3b. The respective cytotoxic activities for the target cells shown in FIGS. 3a and 3b were determined at the same time. FIG. 3a shows the cytotoxic activity of $WT1_{187}$ peptide-specific CTLs against B-LCLs transformed with the WT1 gene (WT1-expressing, HLA-A*0206-positive; closed triangle), or B-LCLs transformed with a mock vector (non-WT1-expressing, HLA-A*0206-positive; closed square). FIG. 3b shows that the cytotoxic activity of $WT1_{187}$ peptide-specific CTLs against 0206K562 cells (WT1-expressing, HLA-A*0206-positive; closed square), K562 cells (WT1-expressing, HLA-A*0206-negative; open square), KH88 cells (WT1-expressing, HLA-A*0206-negative; closed circle), or JY cells (non-WT1-expressing, HLA-A*0206-negative; closed triangle).

The CTLs showed a stronger cytotoxic activity against the B-LCLs transformed with WT1 (WT1-expressing, HLA-A*0206-positive) than against the B-LCLs transformed with a mock vector (non-WT1-expressing, HLA-A*0206-positive) (FIG. 3a). Further, as shown in FIG. 3b, the CTLs showed a stronger cytotoxic activity against the 0206K562 cells transformed with HLA-A*0206 (WT1-expressing, HLA-A*0206-positive) than against the K562 cells (WT1-expressing, HLA-A*0206-negative), the KH88 cells (WT1-expressing, HLA-A*0206-negative), or the JY cells (non-WT1-expressing, HLA-A*0206-negative). In other words, the CTLs showed a significant cytotoxic activity against WT1-expressing, HLA-A*0206-positive target leukemia cells, but no cytotoxic activity against non-WT1-expressing and/or HLA-A*0206-negative cells. This result demonstrates that $WT1_{187}$ peptide-specific CTLs prepared in vitro show the cytotoxic activity against tumor cells endogenously expressing WT1 like leukemia cells and being HLA-A*0206-positive. The result in FIG. 3b strongly suggests that the cytotoxic activity of $WT1_{187}$ peptide-specific CTLs was restricted by HLA-A class I. This is based on the fact that a stronger cytotoxic activity was observed against 0206K562 cells than against K562 cells.

The above results demonstrate that the above-mentioned cultured CTLs are $WT1_{187}$ peptide-specific CTLs.

The results of each figure are typical data, and basically reproducible with some variation.

Example 3

Confirmation of the HLA Class by which $WT1_{187}$ Peptide-Specific CTLs are Restricted It was examined whether the cytotoxic activity of the $WT1_{187}$ peptide-specific CTLs obtained in Example 2 was restricted by HLA class I. The $^{51}$Cr release cytotoxicity test was performed in the presence or absence of mAbs against HLA class I or HLA class II. Autologous B-LCLs were used as a target cell. In this experiment, the E/T ratio was 5:1.

Figure 4:
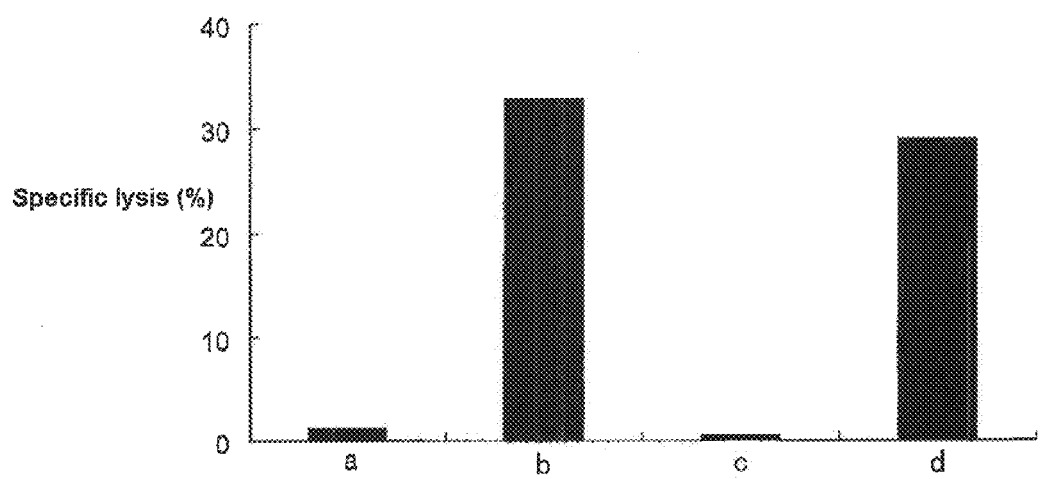
FIG. 4 shows the inhibition of the cytotoxic activity of $WT1_{187}$ peptide-specific CTLs by HLA class I and/or class II antibodies.

The results are shown in FIG. 4. FIG. 4a shows the results of the test that was performed using B-LCLs (non-WT1$_{187}$-expressing, HLA-A*0206-positive) as a target cell in the absence of mAbs against HLA class I (anti-HLA class I mAbs) and mAbs against HLA class II (anti-HLA class II mAbs). FIG. 4b shows the results of the test that was performed using WT1$_{187}$ peptide-pulsed B-LCLs (WT1$_{187}$-expressing, HLA-A*0206-positive) as a target cell in the absence of anti-HLA class I mAbs and in the presence of anti-HLA class II mAbs. FIG. 4c shows the results of the test that was performed using WT1$_{187}$ peptide-pulsed B-LCLs (WT1$_{187}$-expressing, HLA-A*0206-positive) as a target cell in the presence of anti-HLA class I mAbs and in the absence of anti-HLA class II mAbs. FIG. 4d shows the results of the test that was performed using WT1$_{187}$ peptide-pulsed B-LCLs (WT1$_{187}$-expressing, HLA-A*0206-positive) as a target cell in the absence of anti-HLA class I mAbs and anti-HLA class II mAbs.

As shown in FIG. 4, the cytotoxic activity of the WT1$_{187}$ peptide-specific CTLs was completely inhibited by addition of an anti-HLA class I antibody, not an anti-HLA class II antibody. The result shows that the cytotoxic activity of WT1$_{187}$ peptide-specific CTLs was restricted by HLA class I as expected.

Example 4

Cytotoxicity Test Against Tumor Cells

The cytotoxicity test against WT1-expressing, HLA-A*0206-positive tumor cells was performed in vitro using the WT1$_{187}$ peptide-specific CTLs obtained in Example 2. The cytotoxicity test was performed according to the $^{51}$Cr release cytotoxicity test described in Example 2. As a result, the WT1$_{187}$ peptide-specific CTLs showed the cytotoxic activity against WT1-expressing tumor cells (data not shown).

Example 5

Figure 5:
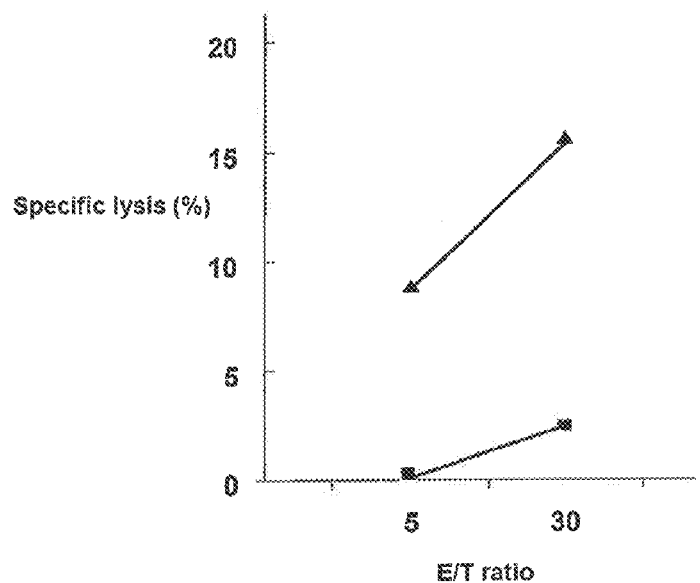
FIG. 5 shows the cytotoxic activity, against $^{51}$Cr-labeled B-LCLs, of $WT1_{126}$ peptide-specific CTLs induced from PBMCs of an HLA-A*0206-positive healthy blood donor.

Preparation of WT1$_{126}$ Peptide-Specific CTLs, and Cytotoxicity Test of the CTLs WT1$_{126}$ peptide-specific CTLs were prepared in the same manner as in Example 2 (3) except that the WT1$_{126}$ peptide (SEQ ID NO: 3) was used instead of the WT1$_{187}$ peptide. The cytotoxicity test was performed using these CTLs in the same manner as in Example 2, to determine the WT1$_{126}$ peptide-specific cytotoxic activity. FIG. 5 shows the cytotoxic activity of WT1$_{126}$ peptide-specific CTLs induced from PBMCs of the same HLA-A*0206-positive healthy blood donor as in FIG. 2b. In FIG. 5, the closed triangle represents cells pulsed with 10 μg/mL of the WT1$_{126}$ peptide, and the closed square represents cells not pulsed with the WT1$_{126}$ peptide. The CTLs showed a stronger cytotoxic activity against the WT1$_{126}$ peptide-pulsed autologous B-LCL cells than against the non-WT1$_{126}$ peptide-pulsed B-LCL cells (FIG. 5). This result shows that the cytotoxic activity of the CTLs is specific to the WT1$_{126}$ peptide.

Figure 6:
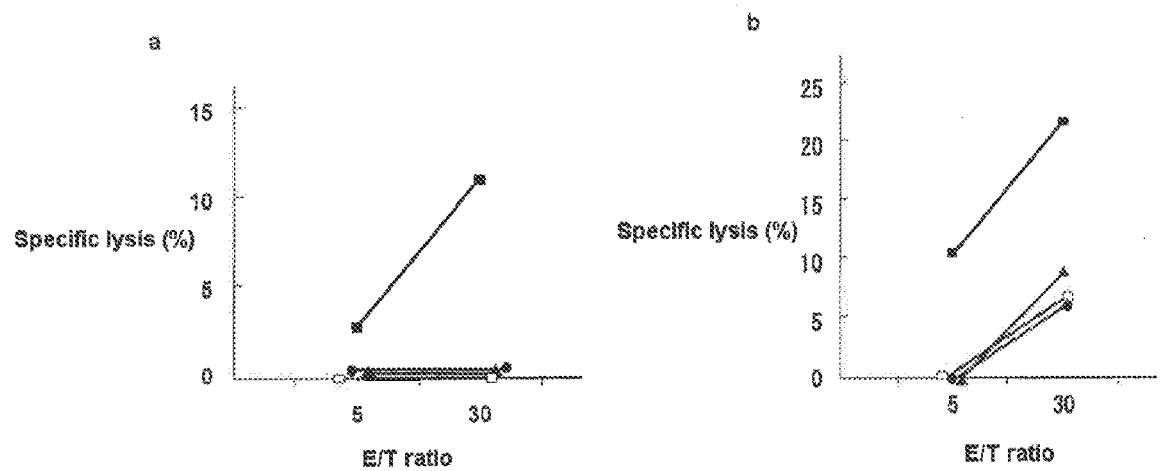
FIGS. 6a and 6b show the respective cytotoxic activities of $WT1_{126}$ peptide-specific CTLs separately induced from two different donors, against 0206K562 cells, K562 cells, KH88 cells or JY cells.

In the same manner as in Example 2, the cytotoxic activity against various target cells endogenously expressing WT1 was examined using the CTLs prepared by stimulating the CD8-positive T cell-enriched PBMCs from the HLA-A*0206-positive blood donors with WT1$_{126}$ peptide-pulsed DCs or PBMCs. The cytotoxic activity against each target cell is shown in FIGS. 6a and 6b. The target cells in FIGS. 6a and 6b are 0206K562 cells (WT1-expressing, HLA-A*0206-positive; closed square), K562 cells (WT1-expressing, HLA-A*0206-negative; open square), KH88 cells (WT1-expressing, HLA-A*0206-negative; closed circle), and JY cells (non-WT1-expressing, HLA-A*0206-negative; closed triangle). FIG. 6a shows the cytotoxic activity of WT1$_{126}$ peptide-specific CTLs induced from PBMCs of the same HLA-A*0206-positive healthy blood donor as in FIG. 2a. FIG. 6b shows the cytotoxic activity of WT1$_{126}$ peptide-specific CTLs induced from PBMCs of the same HLA-A*0206-positive healthy blood donor as in FIG. 2b.

Like WT1$_{187}$ peptide-specific CTLs, the WT1$_{126}$ peptide-specific CTLs showed a significant cytotoxic activity against WT1-expressing, HLA-A*0206-positive target leukemia cells, but no cytotoxic activity against non-WT1-expressing and/or HLA-A*0206-negative cells. This result demonstrates that WT1$_{126}$ peptide-specific CTLs prepared in vitro show the cytotoxic activity against tumor cells endogenously expressing WT1 like leukemia cells and being HLA-A*0206-positive. The results of FIGS. 6a and 6b strongly suggest that the cytotoxic activity of WT1$_{126}$ peptide-specific CTLs was restricted by HLA-A class I. This is based on the fact that a stronger cytotoxic activity was observed against 0206K562 cells than against K562 cells.

The above results demonstrate that the obtained CTLs are WT1$_{126}$ peptide-specific CTLs.

The results of each figure are typical data, and basically reproducible with some variation.

Example 6

Preparation of Vaccine Compositions

The following cancer vaccine compositions 1 to 8 were prepared. These are only examples of the cancer vaccine composition of the present invention.

Cancer Vaccine Composition 1

| | |
|---|---|
| WT1$_{187}$ peptide | 3 mg |
| Montanide ISA-51 | 400 mg |
| 5% glucose in water | 400 mg |

The above-mentioned ingredients were mixed and the mixture was named cancer vaccine composition 1.

Cancer Vaccine Composition 2

| | |
|---|---|
| WT1$_{187}$ peptide | 1 mg |
| Montanide ISA-51 | 400 mg |
| 5% glucose in water | 400 mg |

The above-mentioned ingredients were mixed and the mixture was named cancer vaccine composition 2.

Cancer Vaccine Composition 3

| | |
|---|---|
| WT1$_{187}$ peptide | 0.001 mg |
| Montanide ISA-51 | 400 mg |
| 5% glucose in water | 400 mg |

The above-mentioned ingredients were mixed and the mixture was named cancer vaccine composition 3.

Cancer Vaccine Composition 4

| | |
|---|---|
| WT1$_{187}$ peptide | 10 mg |
| Montanide ISA-51 | 400 mg |
| 5% glucose in water | 400 mg |

The above-mentioned ingredients were mixed and the mixture was named cancer vaccine composition 4.

Cancer Vaccine Compositions 5 to 8

Cancer vaccine compositions 5 to 8 were prepared in the same manner as in the above-mentioned cancer vaccine compositions 1 to 4 except that the WT1$_{126}$ peptide was used instead of the WT1$_{187}$ peptide.

Example 7

Affinity of Modified Peptides to HLA-A*0206 Molecules

As for the WT1$_{187}$ peptide, the WT1$_{126}$ peptide, and modified peptides comprising substitution of an amino acid residue at position 1, 2, 3 or 9 from the N terminus of the WT1$_{187}$ peptide or the WT1$_{126}$ peptide, the affinity to HLA-A*0206 molecules was analyzed by use of the NetMHC2.0 Server-prediction program. The analysis results of modified WT1$_{187}$ peptides and modified WT1$_{126}$ peptides are shown in Tables 1 and 2, respectively. The smaller value (the peptide has a binding ability at a lower concentration) indicates the higher affinity.

TABLE 1

| Peptide | Amino acid sequence | SEQ ID NO | Predicted score | Affinity (nM) | Binding Strength |
|---|---|---|---|---|---|
| WT1$_{187}$ | SLGEQQYSV | 2 | 0.776 | 11 | Strong binding (SB) |
| WT1$_{187}$P1G | GLGEQQYSV | 4 | 0.756 | 13 | SB |
| WT1$_{187}$P1A | ALGEQQYSV | 5 | 0.812 | 7 | SB |
| WT1$_{187}$P1V | VLGEQQYSV | 6 | 0.755 | 14 | SB |
| WT1$_{187}$P1L | LLGEQQYSV | 7 | 0.810 | 7 | SB |
| WT1$_{187}$P1I | ILGEQQYSV | 8 | 0.782 | 10 | SB |
| WT1$_{187}$P1M | MLGEQQYSV | 9 | 0.877 | 3 | SB |
| WT1$_{187}$P1W | WLGEQQYSV | 10 | 0.876 | 3 | SB |
| WT1$_{187}$P1F | FLGEQQYSV | 11 | 0.926 | 2 | SB |
| WT1$_{187}$P1Y | YLGEQQYSV | 12 | 0.896 | 3 | SB |
| WT1$_{187}$P2V | SVGEQQYSV | 13 | 0.722 | 20 | SB |
| WT1$_{187}$P2Q | SQGEQQYSV | 14 | 0.824 | 6 | SB |
| WT1$_{187}$P2I | SIGEQQYSV | 15 | 0.734 | 17 | SB |
| WT1$_{187}$P2M | SMGEQQYSV | 16 | 0.798 | 8 | SB |
| WT1$_{187}$P3L | SLLEQQYSV | 17 | 0.865 | 4 | SB |
| WT1$_{187}$P3A | SLAEQQYSV | 18 | 0.844 | 5 | SB |
| WT1$_{187}$P3V | SLVEQQYSV | 19 | 0.869 | 4 | SB |

TABLE 1-continued

| Peptide | Amino acid sequence | SEQ ID NO | Predicted score | Affinity (nM) | Binding Strength |
|---|---|---|---|---|---|
| WT1$_{187}$P3M | SLMEQQYSV | 20 | 0.896 | 3 | SB |
| WT1$_{187}$P3P | SLPEQQYSV | 21 | 0.791 | 9 | SB |
| WT1$_{187}$P3W | SLWEQQYSV | 22 | 0.883 | 3 | SB |
| WT1$_{187}$P3F | SLFEQQYSV | 23 | 0.864 | 4 | SB |
| WT1$_{187}$P3Y | SLYEQQYSV | 24 | 0.857 | 4 | SB |
| WT1$_{187}$P3S | SLSEQQYSV | 25 | 0.801 | 8 | SB |
| WT1$_{187}$P3I | SLIEQQYSV | 26 | 0.880 | 3 | SB |
| WT1$_{187}$P9L | SLGEQQYSL | 53 | 0.586 | 88 | weak binding |

TABLE 2

| Peptide | Amino acid sequence | SEQ ID NO | Predicted score | Affinity (nM) | Binding Strength |
|---|---|---|---|---|---|
| WT1$_{126}$ | RMFPNAPYL | 3 | 0.83 | 6 | SB |
| WT1$_{126}$P1G | GMFPNAPYL | 27 | 0.76 | 14 | SB |
| WT1$_{126}$P1A | AMFPNAPYL | 28 | 0.80 | 8 | SB |
| WT1$_{126}$P1V | VMFPNAPYL | 29 | 0.75 | 15 | SB |
| WT1$_{126}$P1L | LMFPNAPYL | 30 | 0.80 | 8 | SB |
| WT1$_{126}$P1I | IMFPNAPYL | 31 | 0.77 | 11 | SB |
| WT1$_{126}$P1M | MMFPNAPYL | 32 | 0.86 | 4 | SB |
| WT1$_{126}$P1W | WMFPNAPYL | 33 | 0.88 | 3 | SB |
| WT1$_{126}$P1F | FMFPNAPYL | 34 | 0.91 | 2 | SB |
| WT1$_{126}$P1Y | YMFPNAPYL | 35 | 0.88 | 3 | SB |
| WT1$_{126}$P2V | RVFPNAPYL | 36 | 0.78 | 11 | SB |
| WT1$_{126}$P2Q | RQFPNAPYL | 37 | 0.85 | 4 | SB |
| WT1$_{126}$P2A | RAFPNAPYL | 38 | 0.67 | 35 | SB |
| WT1$_{126}$P2L | RLFPNAPYL | 39 | 0.80 | 8 | SB |
| WT1$_{126}$P2I | RIFPNAPYL | 40 | 0.78 | 10 | SB |
| WT1$_{126}$P3I | RMIPNAPYL | 41 | 0.84 | 5 | SB |
| WT1$_{126}$P3L | RMLPNAPYL | 42 | 0.83 | 6 | SB |
| WT1$_{126}$P3G | RMGPNAPYL | 43 | 0.71 | 23 | SB |
| WT1$_{126}$P3A | RMAPNAPYL | 44 | 0.79 | 9 | SB |
| WT1$_{126}$P3V | RMVPNAPYL | 45 | 0.82 | 6 | SB |
| WT1$_{126}$P3M | RMMPNAPYL | 46 | 0.86 | 4 | SB |
| WT1$_{126}$P3P | RMPPNAPYL | 47 | 0.72 | 21 | SB |
| WT1$_{126}$P3W | RMWPNAPYL | 48 | 0.85 | 5 | SB |
| WT1$_{126}$P9V | RMFPNAPYV | 49 | 0.91 | 2 | SB |
| WT1$_{126}$P9A | RMFPNAPYA | 50 | 0.77 | 12 | SB |

TABLE 2-continued

| Peptide | Amino acid sequence | SEQ ID NO | Predicted score | Affinity (nM) | Binding Strength |
|---|---|---|---|---|---|
| $WT1_{126}$P9I | RMFPNAPYI | 51 | 0.81 | 7 | SB |
| $WT1_{126}$P9M | RMFPNAPYM | 52 | 0.65 | 42 | SB |

Example 8

Affinity of Modified Peptides to HLA-A*0201 Molecules

As for the $WT1_{187}$ peptide, the $WT1_{126}$ peptide, and modified peptides comprising substitution of an amino acid residue at position 1, 2, 3 or 9 from the N terminus of the $WT1_{187}$ peptide or the $WT1_{126}$ peptide, the affinity to HLA-A*0201 molecules was analyzed by use of the NetMHC2.0 Server-prediction program. The analysis results of modified $WT1_{187}$ peptides and modified $WT1_{126}$ peptides are shown in Tables 3 and 4, respectively. The smaller value indicates the higher affinity.

TABLE 3

| Peptide | Amino acid sequence | SEQ ID NO | Predicted score | Affinity (nM) | Binding Strength |
|---|---|---|---|---|---|
| $WT1_{187}$ | SLGEQQYSV | 2 | 0.721 | 20 | SB |
| $WT1_{187}$P1G | GLGEQQYSV | 4 | 0.672 | 34 | SB |
| $WT1_{187}$P1A | ALGEQQYSV | 5 | 0.648 | 44 | SB |
| $WT1_{187}$P1V | VLGEQQYSV | 6 | 0.705 | 24 | SB |
| $WT1_{187}$P1L | LLGEQQYSV | 7 | 0.658 | 40 | SB |
| $WT1_{187}$P1I | ILGEQQYSV | 8 | 0.698 | 26 | SB |
| $WT1_{187}$P1M | MLGEQQYSV | 9 | 0.717 | 21 | SB |
| $WT1_{187}$P1W | WLGEQQYSV | 10 | 0.628 | 55 | SB |
| $WT1_{187}$P1F | FLGEQQYSV | 11 | 0.824 | 6 | SB |
| $WT1_{187}$P1Y | YLGEQQYSV | 12 | 0.809 | 7 | SB |
| $WT1_{187}$P2I | SIGEQQYSV | 15 | 0.556 | 121 | SB |
| $WT1_{187}$P2M | SMGEQQYSV | 16 | 0.740 | 16 | SB |
| $WT1_{187}$P3A | SLAEQQYSV | 18 | 0.811 | 7 | SB |
| $WT1_{187}$P3V | SLVEQQYSV | 19 | 0.766 | 12 | SB |
| $WT1_{187}$P3M | SLMEQQYSV | 20 | 0.876 | 3 | SB |
| $WT1_{187}$P3W | SLWEQQYSV | 22 | 0.863 | 4 | SB |
| $WT1_{187}$P3F | SLFEQQYSV | 23 | 0.852 | 4 | SB |
| $WT1_{187}$P3Y | SLYEQQYSV | 24 | 0.854 | 4 | SB |
| $WT1_{187}$P3S | SLSEQQYSV | 25 | 0.793 | 9 | SB |
| $WT1_{187}$P9L | SLGEQQYSL | 53 | 0.640 | 49 | SB |

TABLE 4

| Peptide | Amino acid sequence | SEQ ID NO | Predicted score | Affinity (nM) | Binding Strength |
|---|---|---|---|---|---|
| $WT1_{126}$P1G | GMFPNAPYL | 27 | 0.80 | 9 | SB |
| $WT1_{126}$P1A | AMFPNAPYL | 28 | 0.81 | 7 | SB |
| $WT1_{126}$P1V | VMFPNAPYL | 29 | 0.81 | 8 | SB |
| $WT1_{126}$P1L | LMFPNAPYL | 30 | 0.82 | 7 | SB |
| $WT1_{126}$P1I | IMFPNAPYL | 31 | 0.81 | 8 | SB |
| $WT1_{126}$P1M | MMFPNAPYL | 32 | 0.85 | 4 | SB |
| $WT1_{126}$P1W | WMFPNAPYL | 33 | 0.80 | 8 | SB |
| $WT1_{126}$P1F | FMFPNAPYL | 34 | 0.91 | 2 | SB |
| $WT1_{126}$P1Y | YMFPNAPYL | 35 | 0.90 | 2 | SB |
| $WT1_{126}$P2V | RVFPNAPYL | 36 | 0.55 | 127 | SB |
| $WT1_{126}$P2Q | RQFPNAPYL | 37 | 0.49 | 262 | SB |
| $WT1_{126}$P2L | RLFPNAPYL | 39 | 0.78 | 10 | SB |
| $WT1_{126}$P2I | RIFPNAPYL | 40 | 0.64 | 48 | SB |
| $WT1_{126}$P3I | RMIPNAPYL | 41 | 0.74 | 16 | SB |
| $WT1_{126}$P3L | RMLPNAPYL | 42 | 0.78 | 10 | SB |
| $WT1_{126}$P3G | RMGPNAPYL | 43 | 0.60 | 73 | SB |
| $WT1_{126}$P3A | RMAPNAPYL | 44 | 0.73 | 17 | SB |
| $WT1_{126}$P3V | RMVPNAPYL | 45 | 0.68 | 31 | SB |
| $WT1_{126}$P3M | RMMPNAPYL | 46 | 0.83 | 6 | SB |
| $WT1_{126}$P3P | RMPPNAPYL | 47 | 0.61 | 66 | SB |
| $WT1_{126}$P3W | RMWPNAPYL | 48 | 0.83 | 6 | SB |
| $WT1_{126}$P9V | RMFPNAPYV | 49 | 0.84 | 5 | SB |
| $WT1_{126}$P9A | RMFPNAPYA | 50 | 0.73 | 18 | SB |
| $WT1_{126}$P9I | RMFPNAPYI | 51 | 0.79 | 9 | SB |
| $WT1_{126}$P9M | RMFPNAPYM | 52 | 0.69 | 29 | SB |

Example 9

Comparison of HLA-A*0201-Restricted CTLs Induced by Various Modified $WT1_{126}$ Peptides (1) Purpose In view of the results of Example 8, the $WT1_{126}$P1F peptide (SEQ ID NO: 34), the $WT1_{126}$P2L peptide (SEQ ID NO: 39), the $WT1_{126}$P3M peptide (SEQ ID NO: 46) and the $WT1_{126}$P9V peptide (SEQ ID NO: 49) were selected as modified $WT1_{126}$ peptides to be tested, and the following experiments were conducted to screen for modified $WT1_{126}$ peptides capable of inducing CTLs having a high cytotoxic activity. The reagents, media, experimental methods, etc. used in Examples 9 to 12 were the same as in Example 1, unless otherwise specified. In Examples 9 to 12, culture was performed at 37° C., unless otherwise specified.

(2) Materials and Methods

From a healthy human donor showing expression of HLA-A*0201 molecules (HLA-A*0201-positive healthy blood donor), PBMCs were isolated, and CD14-positive cells were separated from the PBMCs by use of anti-human CD14 Magnetic Particles-DM. A culture medium was prepared by adding 800 IU/mL GM-CSF and 1000 IU/mL IL-4 to an X-VIVO15 medium supplemented with 1 v/v % human AB serum, and the CD14-positive cells were cultured in the culture medium for 1 day.

To the above culture, a maturation cytokine cocktail containing 10 ng/mL TNFα, 10 ng/mL IL-β, 1000 IU/mL IL-6 and 1 μg/mL PGE2 was added. After additional one day culture, autologous mature DCs were obtained.

The autologous mature DCs were pulsed with 10 μg/mL of a $WT1_{126}$ modified peptide obtained in Example 13 (the $WT1_{126}P1F$ peptide, the $WT1_{126}P2L$ peptide, the $WT1_{126}P3M$ peptide or the $WT1_{126}P9V$ peptide), cultured for 4 hours, and irradiated with 35 Gy of radiation. The thus-obtained cells were used as stimulator cells for CTL induction.

The PBMCs ($2\times10^6$ cells/well) serving as responder cells and the above-mentioned DCs ($2\times10^5$ cells/well) were co-cultured in a 24-well plate. One week later, re-stimulation was given by addition of T2 cells which had been pulsed with the peptide and irradiated with 75 Gy of radiation. Three days after re-stimulation, 20 IU/mL of IL-2 was added. The same re-stimulation was repeated another 3 times by addition of the peptide-pulsed, irradiated T2 cells, and then CD8-positive cells in the responder cells were enriched.

As for the CD8-positive T cells, the reactivity on an HLA-A*0201 tetramer bound to the $WT1_{126}$ peptide was analyzed by a flow cytometer, and the cytotoxic activity against various target cells was examined.

The target cells to be used were K562 cells, 0206K562 cells, JY cells, KH88OF8 cells, TF-1 cells and THP-1 cells, which are shown in Table 5. The features of these cells are shown in Table 5. A B-lymphoblastoid cell line (B-LCL) established by EB viral infection from the blood of an HLA-A*0201-positive donor was also used as a target cell.

TABLE 5

| Target cell | HLA-A*0201 | HLA-A*0206 | WT1 |
|---|---|---|---|
| K562 | negative | negative | expressed |
| 0206K562 | negative | positive | expressed |
| JY | positive | negative | not expressed |
| KH88OF8 | negative | negative | expressed |
| TF-1 | positive | negative | expressed |
| THP-1 | positive | negative | expressed |

(3) Results

Figure 7:
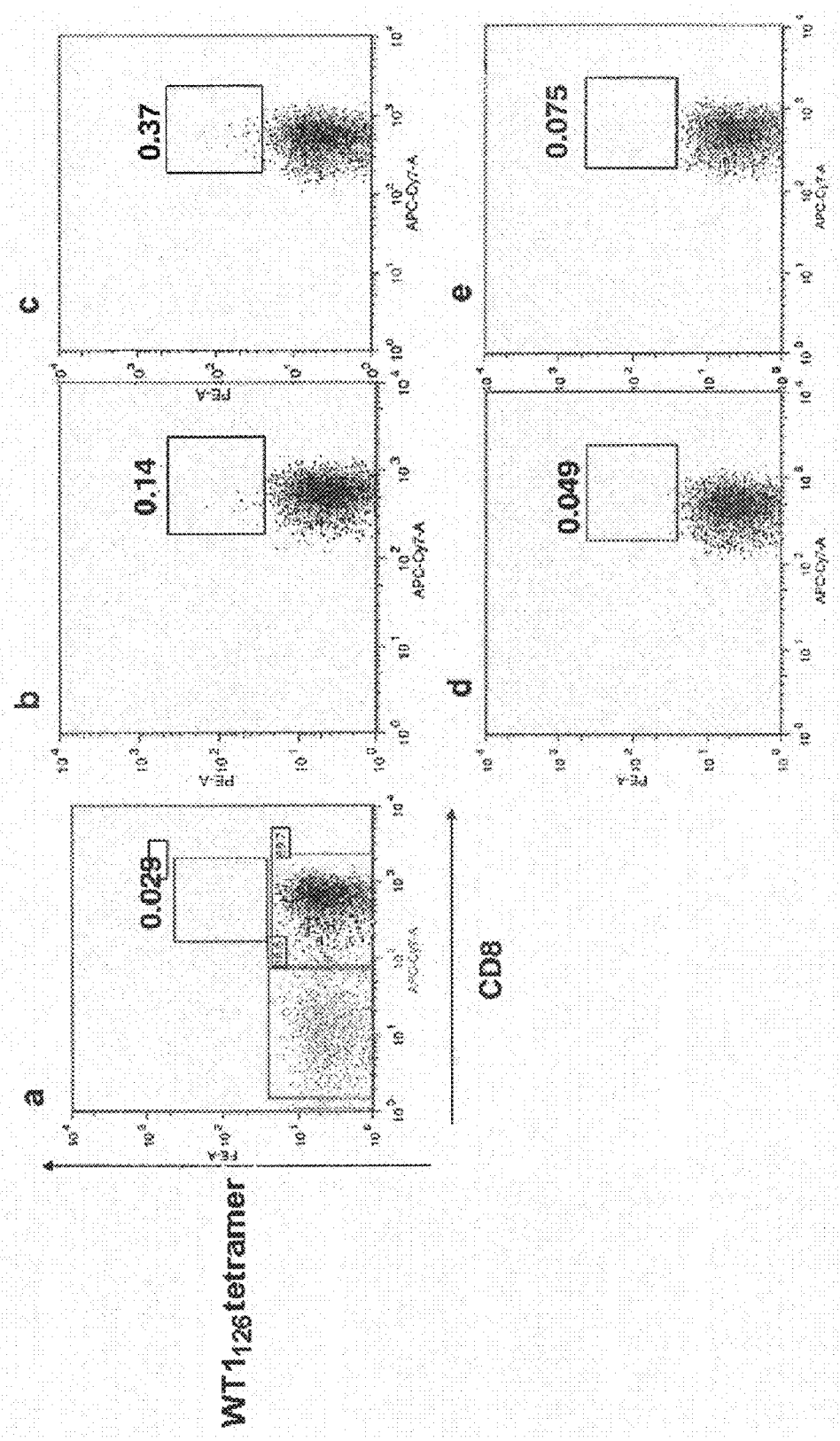
FIG. 7 shows the results of the flow cytometric analysis of CTLs stained with the HLA tetramer bound to the $WT1_{126}$ peptide and the anti-CD8 antibody. The CTLs have been induced by stimulation of PBMCs from the HLA-A*0201-positive donor 1 with modified peptides.

FIG. 7 shows the results of flow cytometric analysis of PBMCs from the HLA-A*0201-positive donor 1 which were stimulated with different modified $WT1_{126}$ peptides and then stained with a PE (Phycoerythrin)-labeled HLA-A*0201 tetramer bound to the $WT1_{126}$ peptide (Medical & Biological Laboratories, Co., Ltd.), and an APC-Cy7-labeled anti-CD8 antibody (APC-Cy7: Allophycocyanin-Cyanine-7). When the PBMCs are stained with the above-mentioned tetramer and anti-CD8 antibody, CTLs induced by stimulation with the modified peptide bind to the tetramer and the anti-CD8 antibody, and thereby, fluorescence emitted by the tetramer and fluorescence emitted by the anti-CD8 antibody can be detected, respectively. In FIGS. 7a to 7e, the vertical axis represents the intensity of fluorescence emitted by the HLA-A*0201 tetramer, and the horizontal axis represents the intensity of fluorescence emitted by the anti-CD8 antibody. Each box in FIGS. 7a to 7e shows the frequency (%) of induced, HLA-A*0201-restricted CTLs capable of recognizing the $WT1_{126}$ peptide. FIG. 7a shows the analysis result of PBMCs which were not stimulated with any $WT1_{126}$ modified peptide and stained with the above-mentioned tetramer and anti-CD8 antibody (background). FIG. 7b shows the analysis result of PBMCs which were stimulated with the $WT1_{126}P1F$ peptide and stained. FIG. 7c shows the analysis result of PBMCs which were stimulated with the $WT1_{126}P2L$ peptide and stained. FIG. 7d shows the analysis result of PBMCs which were stimulated with the $WT1_{126}P3M$ peptide and stained. FIG. 7e shows the analysis result of PBMCs which were stimulated with the $WT1_{126}P9V$ peptide and stained.

The frequency of the above-mentioned CTLs induced by stimulation of PBMCs with the $WT1_{126}P1F$ peptide was 0.14% (FIG. 7b). The frequency of the above-mentioned CTLs induced by stimulation of PBMCs with the $WT1_{126}P2L$ peptide was 0.37% (FIG. 7c). The CTLs induced separately with these peptides were HLA tetramer-positive, CD8-positive and capable of binding to the HLA-A*0201 tetramer bound to the $WT1_{126}$ peptide. These results show that stimulation of PBMCs with the modified $WT1_{126}$ peptide induced CTLs which can recognize the wild-type peptide ($WT1_{126}$ peptide).

Figure 8:
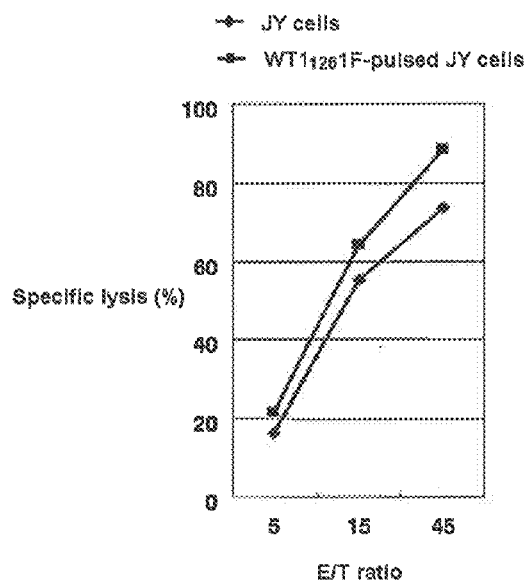
FIG. 8 shows the measurement results of the cytotoxic activity of CTLs induced by stimulation of PBMCs from the HLA-A*0201-positive donor 1 with the $WT1_{126}P1F$ peptide.

FIG. 8 shows the measurement results of the cytotoxic activity of CTLs induced by stimulation of PBMCs from the donor 1 with the $WT1_{126}P1F$ peptide. In FIG. 8, the vertical axis represents the cytotoxic activity, and the horizontal axis represents the ratio of CD8-positive T cells obtained by peptide stimulation (effector: E) relative to target cells (target: T) (E/T ratio). The closed diamond represents the group in which JY cells were used as a target cell, and the closed square represents the group in which JY cells pulsed with the $WT1_{126}P1F$ peptide were used as a target cell.

JY cells are HLA-A*0201-positive and WT1-negative. The CTLs showed a stronger cytotoxic activity against the $WT1_{126}P1F$ peptide-pulsed JY cells than against the non-$WT1_{126}P1F$ peptide-pulsed JY cells. This result shows that CTLs which are specific to the peptide used for the above-mentioned stimulation and restricted by HLA-A*0201 were induced.

Figure 9:
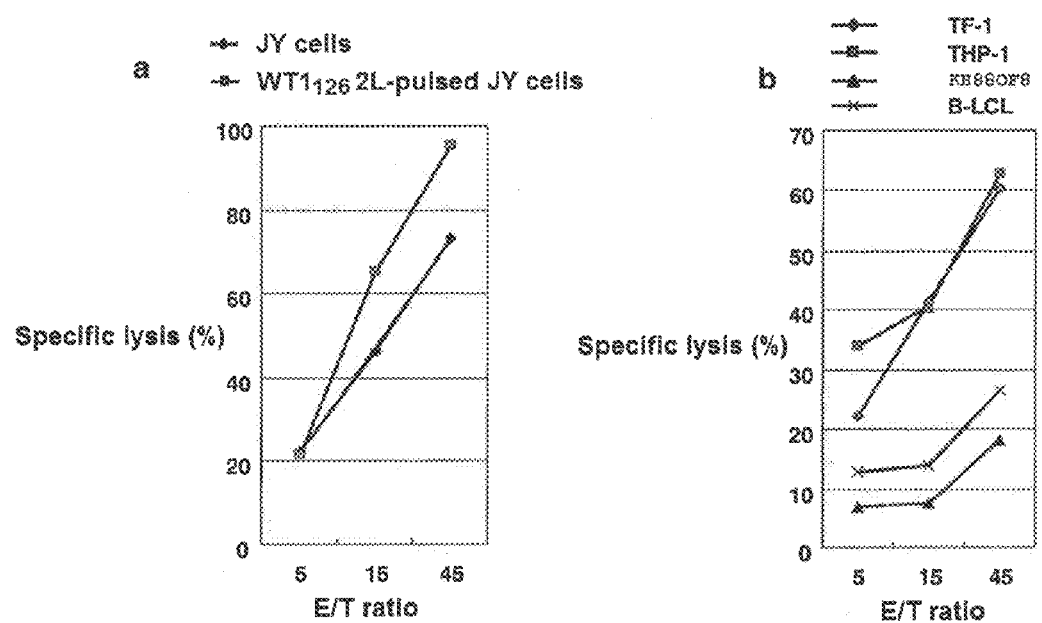
FIG. 9 shows the measurement results of the cytotoxic activity of CTLs induced by stimulation of PBMCs from the HLA-A*0201-positive donor 1 with the $WT1_{126}P2L$ peptide.

FIG. 9 shows the measurement results of the cytotoxic activity of CTLs induced by stimulation of PBMCs from the donor 1 with the $WT1_{126}P2L$ peptide. In FIG. 9, the vertical axis represents the cytotoxic activity, and the horizontal axis represents the ratio of CD8-positive T cells obtained by peptide stimulation (effector: E) relative to target cells (target: T) (E/T ratio). In FIG. 9a, the closed diamond represents the group in which JY cells were used as a target cell, and the closed square represents the group in which JY cells pulsed with the $WT1_{126}P2L$ peptide were used as a target cell. In FIG. 9b, the closed diamond represents the group in which TF-1 cells were used as a target cell, the closed square represents the group in which THP-1 cells were used as a target cell, the closed triangle represents the group in which KH88OF8 cells were used as a target cell, and the cross represents the group in which B-LCL cells were used as a target cell.

The induced CTLs showed a stronger cytotoxic activity against the $WT1_{126}P2L$ peptide-pulsed JY cells than against the non-$WT1_{126}P2L$ peptide-pulsed JY cells (FIG. 9a). The induced CTLs showed a stronger cytotoxic activity against the TF-1 cells and THP-1 cells, both of which are HLA-A*0201-positive and WT1-positive, than against the KH88OF8 cells, which are HLA-A*0201-negative and WT1-positive, and the B-LCL cells, which are HLA-A*0201-positive and WT1-negative (FIG. 9b). As is clear from the results, the CTLs induced by stimulation with the $WT1_{126}P2L$ peptide are restricted by HLA-A*0201, and capable of destroying cancer cells endogenously expressing WT1.

Figure 10:
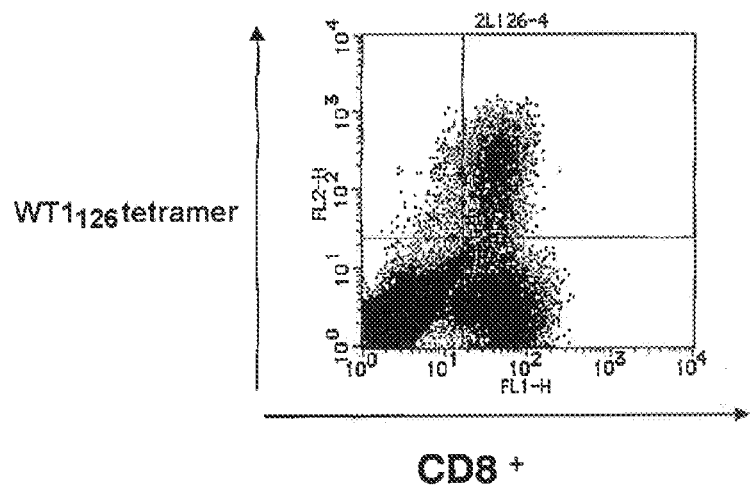
FIG. 10 shows the results of the flow cytometric analysis of CTLs stained with the HLA tetramer bound to the $WT1_{126}$ peptide and the anti-CD8 antibody. The CTLs have been induced by stimulation of PBMCs from the HLA-A*0201-positive donor 2 with the $WT1_{126}P2L$ peptide.

FIG. 10 shows the results of flow cytometric analysis of PBMCs from the HLA-A*0201-positive donor 2 which were stimulated with the $WT1_{126}P2L$ peptide and then stained with the PE-labeled HLA-A*0201 tetramer bound to the $WT1_{126}$ peptide, and the APC-Cy7-labeled anti-CD8 antibody. Namely, FIG. 10 shows the results of the flow cytometric analysis of induced CTLs which were stained with the HLA tetramer bound to the $WT1_{126}$ peptide, and the anti-CD8 antibody. The vertical axis represents the intensity of fluorescence emitted by the HLA-A*0201 tetramer, and the horizontal axis represents the intensity of fluorescence emitted by the anti-CD8 antibody.

The cells in the upper right area of FIG. 10 are induced CTLs which are restricted by HLA-A*0201 and can recognize the $WT1_{126}$ peptide. 5.43% of lymphocytes of the PBMCs stimulated with the $WT1_{126}P2L$ peptide were HLA tetramer-positive, CD8-positive CTLs which are capable of binding to the tetramer of HLA-A*0201 bound to the $WT1_{126}$ peptide. This result shows that stimulation of PBMCs with the modified peptide induced CD8-positive CTLs which can recognize the wild-type peptide.

Figure 11:
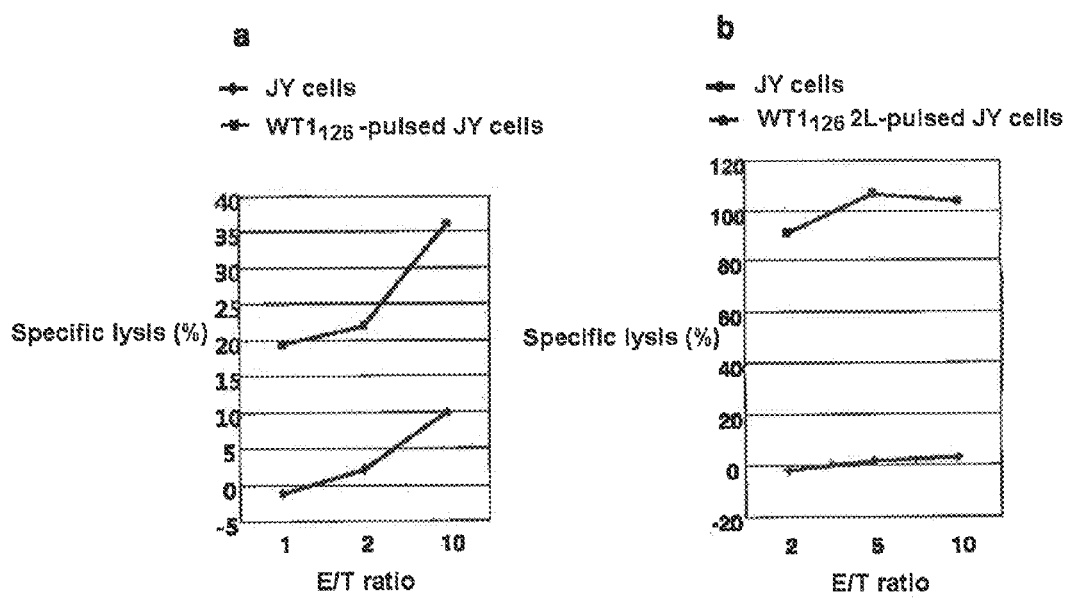
FIG. 11 shows the measurement results of the cytotoxic activity of CTLs induced by stimulation of PBMCs from the donor 2 with the $WT1_{126}P2L$ peptide.

FIG. 11 shows the measurement results of the cytotoxic activity of the CTLs induced by stimulation of PBMCs from the donor 2 with the $WT1_{126}P2L$ peptide. In FIGS. 11a and 11b, the vertical axis represents the cytotoxic activity, and the horizontal axis represents the ratio of CD8-positive T cells obtained by peptide stimulation (effector: E) relative to target cells (target: T) (E/T ratio). In FIG. 11a, the closed diamond represents the group in which JY cells were used as a target cell, and the closed square represents the group in which JY cells pulsed with the $WT1_{126}$ peptide were used as a target cell. In FIG. 11b, the closed diamond represents the group in which JY cells were used as a target cell, and the closed square represents the group in which JY cells pulsed with the $WT1_{126}P2L$ peptide were used as a target cell.

The induced CTLs showed a stronger cytotoxic activity against the $WT1_{126}$ peptide-pulsed JY cells than against the non-$WT1_{126}$ peptide-pulsed JY cells (FIG. 11a). The induced CTLs also showed a stronger cytotoxic activity against the $WT1_{126}P2L$ peptide-pulsed JY cells than against the non-$WT1_{126}P2L$ peptide-pulsed JY cells (FIG. 11b). As is clear from the results, the CTLs induced by stimulation with the $WT1_{126}P2L$ peptide can recognize both of the $WT1_{126}P2L$ peptide and the wild-type $WT1_{126}$ peptide.

Example 10

Comparison of HLA-A*0206-Restricted CTLs Induced by Various Modified $WT1_{126}$ Peptides (1) Purpose In view of the results of Example 7, the $WT1_{126}P1F$ peptide, the $WT1_{126}P2L$ peptide, the $WT1_{126}P3M$ peptide and the $WT1_{126}P9V$ peptide were selected as modified $WT1_{126}$ peptides to be tested, and the following experiments were conducted to screen for modified $WT1_{126}$ peptides capable of inducing CTLs having a high cytotoxic activity.

(2) Materials and Methods

From a healthy human donor showing expression of HLA-A*0206 molecules (HLA-A*0206-positive healthy blood donor), PBMCs were isolated, and CD14-positive cells were separated from the PBMCs by use of anti-human CD14 Magnetic Particles-DM. A culture medium was prepared by adding 800 IU/mL GM-CSF and 1000 IU/mL IL-4 to an X-VIVO15 medium supplemented with 1 v/v % human AB serum, and the CD14-positive cells were cultured in the culture medium for 1 day.

To the above culture, a maturation cytokine cocktail containing 10 ng/mL TNFα, 10 ng/mL IL-β, 1000 IU/mL IL-6 and 1 μg/mL PGE2 was added. After additional one day culture, autologous mature DCs were obtained.

The autologous mature DCs were pulsed with 10 μg/mL of a $WT1_{126}$ modified peptide obtained in Example 13 (the $WT1_{126}P1F$ peptide, the $WT1_{126}P2L$ peptide, the $WT1_{126}P3M$ peptide or the $WT1_{126}P9V$ peptide), cultured for 4 hours, and irradiated with 35 Gy of radiation. The thus-obtained cells were used as stimulator cells for CTL induction.

CD8-positive T cell-enriched PBMCs ($2 \times 10^6$ cells/well) and the above-mentioned DCs ($1 \times 10^5$ cells/well) were co-cultured in a 24-well plate. Ten days later, re-stimulation was given by addition of PBMCs which had been pulsed with the peptide and irradiated with 35 Gy of radiation. Two days after re-stimulation, 10 IU/mL of IL-2 and 10 ng/mL of IL-7 were added. After the same re-stimulation was repeated another 4 times, CD8-positive T cells were enriched. The CD8-positive T cells were examined for the cytotoxic activity against various target cells.

The target cells to be used were B-LCLs established by EB viral infection from the blood of an HLA-A*0206-positive donor, K562 cells and 0206K562 cells.

(3) Results

Figure 12:
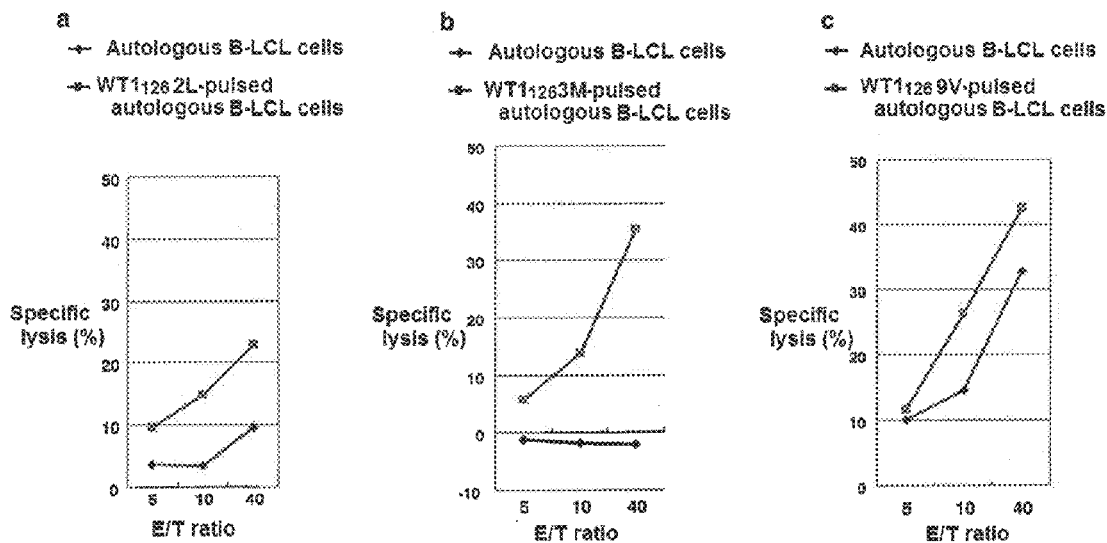
FIG. 12 shows the measurement results of the cytotoxic activity of CTLs induced by stimulation of PBMCs from the HLA-A*0206-positive donor 3 with modified $WT1_{126}$ peptides.

FIG. 12 shows the measurement results of the cytotoxic activity of CTLs induced by stimulation of PBMCs from the HLA-A*0206-positive donor 3 with different peptides. FIG. 12a shows the cytotoxic activity of CTLs induced by stimulation with the $WT1_{126}P2L$ peptide. FIG. 12b shows the cytotoxic activity of CTLs induced by stimulation with the $WT1_{126}P3M$ peptide. FIG. 12c shows the cytotoxic activity of CTLs induced by stimulation with the $WT1_{126}P9V$ peptide. In FIGS. 12a to 12c, the vertical axis represents the cytotoxic activity, and the horizontal axis represents the ratio of CD8-positive T cells obtained by peptide stimulation (effector: E) relative to target cells (target: T) (E/T ratio). The closed diamond represents the group in which autologous B-LCL cells were used as a target cell, and the closed square represents the group in which autologous B-LCL cells pulsed with the same modified $WT1_{126}$ peptide as used for the above-mentioned stimulation were used as a target cell.

The CTLs induced by stimulation with the $WT1_{126}P2L$ peptide showed a stronger cytotoxic activity against the $WT1_{126}P2L$ peptide-pulsed autologous B-LCL cells, which are HLA-A*0206-positive and WT1-negative, than against the non-$WT1_{126}P2L$ peptide-pulsed autologous B-LCL cells (FIG. 12a). The CTLs induced by stimulation with the $WT1_{126}P3M$ peptide showed a stronger cytotoxic activity against the $WT1_{126}P3M$ peptide-pulsed autologous B-LCL cells, which are HLA-A*0206-positive and WT1-negative, than against the non-$WT1_{126}P3M$ peptide-pulsed autologous B-LCL cells (FIG. 12b). The CTLs induced by stimulation with the $WT1_{126}P9V$ peptide showed a stronger cytotoxic activity against the $WT1_{126}P9V$ peptide-pulsed autologous B-LCL cells, which are HLA-A*0206-positive and WT1-negative, than against the non-$WT1_{126}P9V$ peptide-pulsed autologous B-LCL cells (FIG. 12c).

These results show that CTLs which are specific to the peptide used for the above-mentioned stimulation and restricted by HLA-A*0206 were induced.

Figure 13:
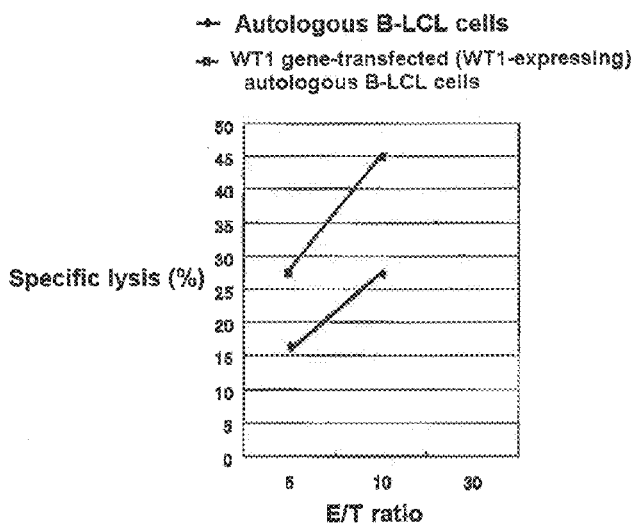
FIG. 13 shows the measurement results of the cytotoxic activity of CTLs induced by stimulation of PBMCs from the HLA-A*0206-positive donor 3 with the $WT1_{126}P9V$ peptide.

FIG. 13 shows the measurement results of the cytotoxic activity of CTLs induced by stimulation of PBMCs from the HLA-A*0206-positive donor 3 with the $WT1_{126}P9V$ peptide.

In FIG. 13, the vertical axis represents the cytotoxic activity, and the horizontal axis represents the ratio of CD8-positive T cells obtained by peptide stimulation (effector: E) relative to target cells (target: T) (E/T ratio). The closed diamond represents the group in which autologous B-LCL cells were used as a target cell, and the closed square represents the group in which WT1 gene-transfected autologous B-LCL cells were used as a target cell.

In FIG. 13, the CTLs induced by stimulation with the $WT1_{126}P9V$ peptide showed a stronger cytotoxic activity against autologous B-LCL cells made to be WT1-positive by transfection of the WT1 gene into B-LCL cells, which were originally HLA-A*0206-positive and WT1-negative, than against the non-WT1 gene-transfected autologous B-LCL cells (FIG. 12c). As is clear from the result, the CTLs induced by stimulation with the $WT1_{126}P9V$ peptide are restricted by HLA-A*0206, and show the cytotoxic activity by recognizing the wild-type $WT1_{126}$ peptide presented endogenously.

Figure 14:
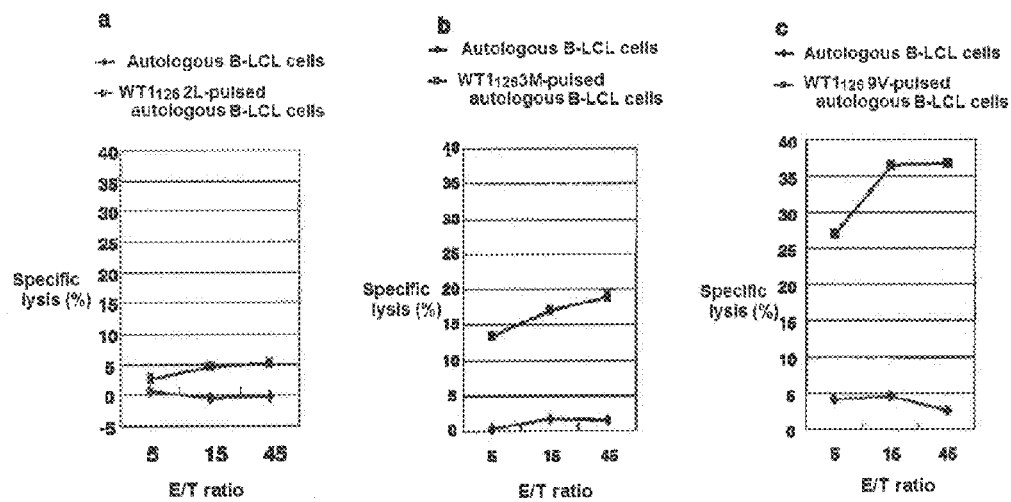
FIG. 14 shows the measurement results of the cytotoxic activity of CTLs induced by stimulation of PBMCs from the HLA-A*0206-positive donor 4 with modified $WT1_{126}$ peptides.

FIG. 14 shows the measurement results of the cytotoxic activity of CTLs induced by stimulation of PBMCs from the HLA-A*0206-positive donor 4 with different peptides. FIG. 14a shows the cytotoxic activity of CTLs induced by stimulation with the $WT1_{126}P2L$ peptide. FIG. 14b shows the cytotoxic activity of CTLs induced by stimulation with the $WT1_{126}P3M$ peptide. FIG. 14c shows the cytotoxic activity of CTLs induced by stimulation with the $WT1_{126}P9V$ peptide. In FIGS. 14a to 14c, the vertical axis represents the cytotoxic activity, and the horizontal axis represents the ratio of CD8-positive T cells obtained by peptide stimulation (effector: E) relative to target cells (target: T) (E/T ratio). The closed diamond represents the group in which autologous B-LCL cells were used as a target cell, and the closed square represents the group in which autologous B-LCL cells pulsed with the same modified $WT1_{126}$ peptide as used for the above-mentioned stimulation were used as a target cell.

The CTLs induced by stimulation with the $WT1_{126}P2L$ peptide showed a stronger cytotoxic activity against the $WT1_{126}P2L$ peptide-pulsed autologous B-LCL cells, which are HLA-A*0206-positive and WT1-negative, than against the non-$WT1_{126}P2L$ peptide-pulsed autologous B-LCL cells (FIG. 14a). The CTLs induced by stimulation with the $WT1_{126}P3M$ peptide showed a stronger cytotoxic activity against the $WT1_{126}P3M$ peptide-pulsed autologous B-LCL cells, which are HLA-A*0206-positive and WT1-negative, than against the non-$WT1_{126}P3M$ peptide-pulsed autologous B-LCL cells (FIG. 14b). The CTLs induced by stimulation with the $WT1_{126}P9V$ peptide showed a stronger cytotoxic activity against the $WT1_{126}P9V$ peptide-pulsed autologous B-LCL cells, which are HLA-A*0206-positive and WT1-negative, than against the non-$WT1_{126}P9V$ peptide-pulsed autologous B-LCL cells (FIG. 14c). These results show that CTLs which are specific to the peptide used for the above-mentioned stimulation and restricted by HLA-A*0206 were induced.

Figure 15:
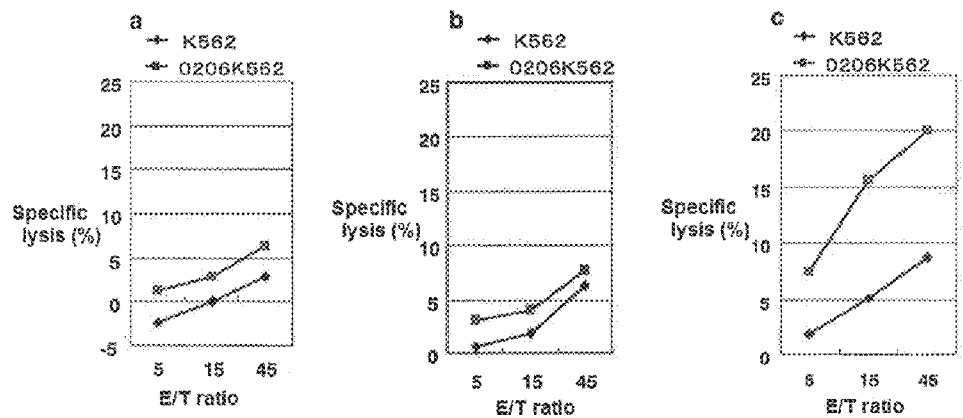
FIG. 15 shows the measurement results of the cytotoxic activity of CTLs induced by stimulation of PBMCs from the HLA-A*0206-positive donor 4 with modified $WT1_{126}$ peptides.

FIG. 15 shows the measurement results of the cytotoxic activity of CTLs induced by stimulation of PBMCs from the HLA-A*0206-positive donor 4 with different peptides. The target cells to be used were HLA-A*0206-negative, WT1-positive K562 cells, and K562 cells made to endogenously present WT1 antigen peptides by transfection of the HLA-A*0206 gene thereinto (0206K562 cells). FIG. 15a shows the cytotoxic activity of CTLs induced by stimulation with the $WT1_{126}P2L$ peptide. FIG. 15b shows the cytotoxic activity of CTLs induced by stimulation with the $WT1_{126}P3M$ peptide. FIG. 15c shows the cytotoxic activity of CTLs induced by stimulation with the $WT1_{126}P9V$ peptide. In FIGS. 15a to 15c, the vertical axis represents the cytotoxic activity, and the horizontal axis represents the ratio of CD8-positive T cells obtained by peptide stimulation (effector: E) relative to target cells (target: T) (E/T ratio). The closed diamond represents the group in which K562 cells were used as a target cell, and the closed square represents the group in which 0206K562 cells, i.e., K562 cells made to endogenously present WT1 antigen peptides by transfection of the HLA-A*0206 gene thereinto, were used as a target cell.

In FIGS. 15a to 15c, the CTLs induced by stimulation with the $WT1_{126}P2L$ peptide, the $WT1_{126}P3M$ peptide or the $WT1_{126}P9V$ peptide showed a stronger cytotoxic activity against the 0206K562 cells than against the K562 cells, in each case. As is clear from the results, the CTLs induced by stimulation with any of these modified peptides are restricted by HLA-A*0206, and show the cytotoxic activity by recognizing the wild-type $WT1_{126}$ peptide presented endogenously.

Example 11

Comparison of HLA-A*0201-Restricted CTLs Induced by Various Modified $WT1_{187}$ Peptides (1) Purpose In view of the results of Example 8, the $WT1_{187}P1F$ peptide (SEQ ID NO: 11), the $WT1_{187}P2M$ peptide (SEQ ID NO: 16) and the $WT1_{187}P3M$ peptide (SEQ ID NO: 20) were selected as modified $WT1_{187}$ peptides to be tested, and the following experiments were conducted to screen for modified $WT1_{187}$ peptides capable of inducing CTLs having a high cytotoxic activity.

(2) Materials and Methods

From a healthy human donor showing expression of HLA-A*0201 molecules (HLA-A*0201-positive healthy blood donor), PBMCs were isolated, and CD14-positive cells were separated from the PBMCs using anti-human CD14 Magnetic Particles-DM. A culture medium was prepared by adding 800 IU/mL GM-CSF and 1000 IU/mL IL-4 to an X-VIVO15 medium supplemented with 1 v/v % human AB serum, and the CD14-positive cells were cultured in the culture medium for 1 day.

To the above culture, a maturation cytokine cocktail containing 10 ng/mL TNFα, 10 ng/mL IL-β, 1000 IU/mL IL-6 and 1 µg/mL PGE2 was added. After additional one day culture, autologous mature DCs were obtained.

The autologous mature DCs were pulsed with 10 µg/mL of a modified $WT1_{187}$ peptide obtained in Example 13 (the $WT1_{187}P1F$ peptide, the $WT1_{187}P2M$ peptide or the $WT1_{187}P3M$ peptide), cultured for 4 hours, and irradiated with 35 Gy of radiation. The thus-obtained cells were used as stimulator cells for CTL induction.

The PBMCs ($2 \times 10^6$ cells/well) serving as responder cells and the above-mentioned DCs ($2 \times 10^5$ cells/well) were co-cultured in a 24-well plate. One week later, re-stimulation was given by addition of T2 cells which had been pulsed with the peptide and irradiated with 75 Gy of radiation. Three days after re-stimulation, 20 IU/mL of IL-2 was added. The same re-stimulation was repeated another 3 times by addition of the peptide-pulsed, irradiated T2 cells, and then CD8-positive cells in the responder cells were enriched. The CD8-positive T cells were examined for the cytotoxic activity against target cells, i.e., JY cells here.

(3) Results

Figure 16:
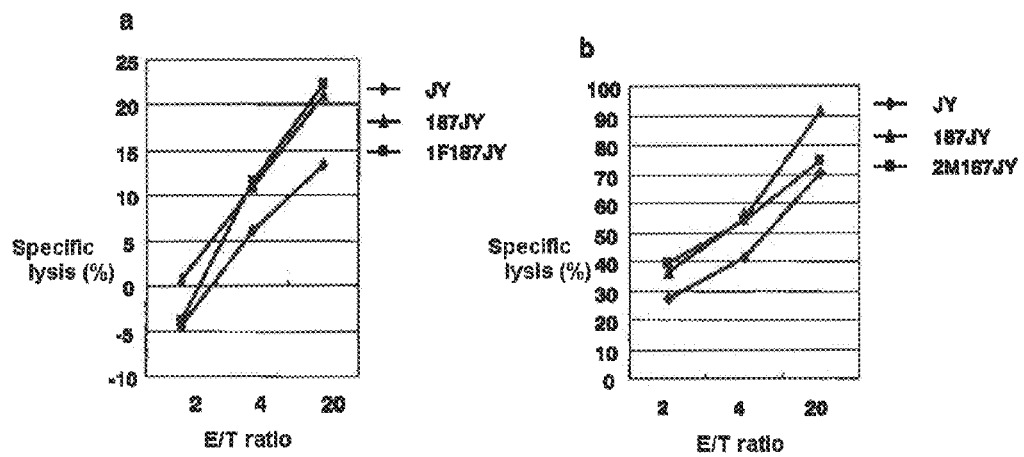
FIG. 16 shows the measurement results of the cytotoxic activity of CTLs induced by stimulation of PBMCs from an HLA-A*0201-positive donor with modified $WT1_{187}$ peptides.

FIG. 16 shows the measurement results of the cytotoxic activity of CTLs induced by stimulation of PBMCs from the HLA-A*0201-positive donor with the $WT1_{187}P1F$ peptide (FIG. 16a) or the $WT1_{187}P2M$ peptide (FIG. 16b). In FIGS.

16a and 16b, the vertical axis represents the cytotoxic activity, and the horizontal axis represents the ratio of CD8-positive T cells obtained by peptide stimulation (effector: E) relative to target cells (target: T) (E/T ratio). The closed diamond represents the group in which JY cells were used as a target cell, the closed triangle represents the group in which $WT1_{187}$ peptide-pulsed JY cells were used as a target cell, and the closed square represents the group in which JY cells pulsed with the $WT1_{187}$ modified peptide ($WT1_{187}$P1F peptide) that was used for the above-mentioned stimulation were used as a target cell. JY cells are HLA-A*0201-positive and WT1-negative.

The CTLs induced by stimulation with the $WT1_{187}$P1F peptide showed an equal cytotoxic activity against the $WT1_{187}$ peptide-pulsed JY cells and the $WT1_{187}$P1F peptide-pulsed JY cells, and the activity was stronger than that against the non-peptide-pulsed JY cells (FIG. 16a). The CTLs induced by stimulation with the $WT1_{187}$P2M peptide showed an equal cytotoxic activity against the $WT1_{187}$ peptide-pulsed JY cells and the $WT1_{187}$P2M peptide-pulsed JY cells, and the activity was stronger than that against the non-peptide-pulsed JY cells (FIG. 16b). As is clear from the results, the CTLs induced by stimulation with the modified peptide can recognize both of the modified peptide and the wild-type $WT1_{187}$ peptide.

Example 12

Comparison of HLA-A*0206-Restricted CTLs Induced by Various Modified $WT1_{187}$ Peptides (1) Purpose In view of the results of Example 7, the $WT1_{187}$P1F peptide, the $WT1_{187}$P2M peptide and the $WT1_{187}$P3M peptide were selected as modified $WT1_{187}$ peptides to be tested, and the following experiments were conducted to screen for modified $WT1_{187}$ peptides capable of inducing CTLs having a high cytotoxic activity.

(2) Materials and Methods

From a healthy human donor showing expression of HLA-A*0206 molecules (HLA-A*0206-positive healthy blood donor), PBMCs were isolated, and CD14-positive cells were separated from the PBMCs using anti-human CD14 Magnetic Particles-DM. A culture medium was prepared by adding 800 IU/mL GM-CSF and 1000 IU/mL IL-4 to an X-VIVO15 medium supplemented with 1 v/v % human AB serum, and the CD14-positive cells were cultured in the culture medium for 1 day.

To the above culture, a maturation cytokine cocktail containing 10 ng/mL TNFα, 10 ng/mL IL-β, 1000 IU/mL IL-6 and 1 μg/mL PGE2 was added. After additional one day culture, autologous mature DCs were obtained.

The autologous mature DCs were pulsed with a modified $WT1_{187}$ peptide obtained in Example 13 (the $WT1_{187}$P1F peptide, the $WT1_{187}$P2M peptide or the $WT1_{187}$P3M peptide), cultured for 4 hours, and irradiated with 35 Gy of radiation. The thus-obtained cells were used as stimulator cells for CTL induction.

CD8-positive T cell-enriched PBMCs ($2\times10^6$ cells/well) and the above-mentioned DCs ($1\times10^5$ cells/well) were co-cultured in a 24-well plate. Ten days later, re-stimulation was given by addition of PBMCs which had been pulsed with the peptide and irradiated with 35 Gy of radiation. Two days after re-stimulation, 10 IU/mL of IL-2 and 10 ng/mL of IL-7 were added. After the same re-stimulation was repeated another 4 times, CD8-positive T cells were enriched. The CD8-positive T cells were examined for the cytotoxic activity against various target cells.

The target cells to be used were B-LCLs established by EB viral infection from the blood of an HLA-A*0206-positive donor, K562 cells and 0206K562 cells.

(3) Results

Figure 17:
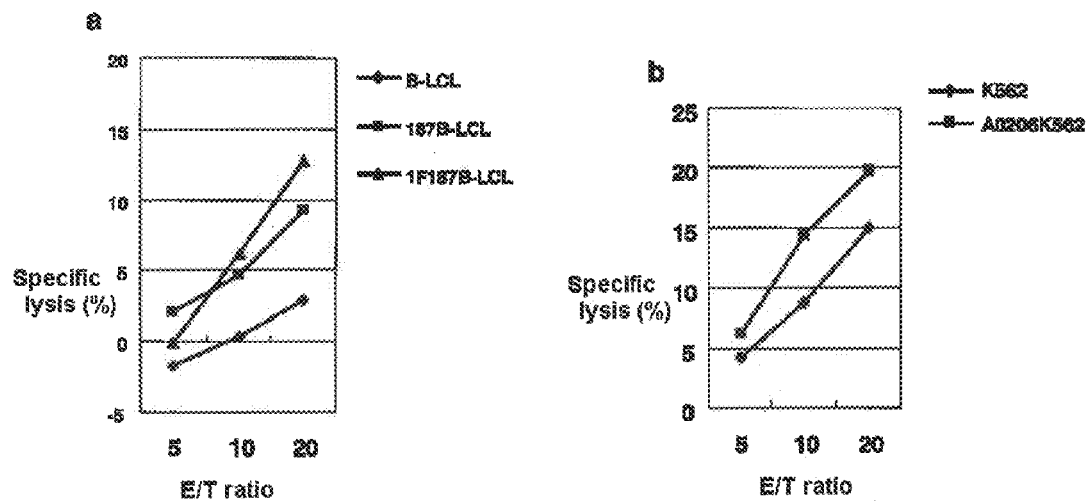
FIG. 17 shows the measurement results of the cytotoxic activity of CTLs induced by stimulation of PBMCs from an HLA-A*0206-positive donor with the $WT1_{187}P1F$ peptide.

FIG. 17 shows the measurement results of the cytotoxic activity of CTLs induced by stimulation of PBMCs from the HLA-A*0206-positive donor with the $WT1_{187}$P1F peptide. In FIG. 17, the vertical axis represents the cytotoxic activity, and the horizontal axis represents the ratio of CD8-positive T cells obtained by peptide stimulation (effector: E) relative to target cells (target: T) (E/T ratio). In FIG. 17a, the closed diamond represents the group in which B-LCL cells were used as a target cell, the closed square represents the group in which $WT1_{187}$ peptide-pulsed B-LCL cells were used as a target cell, and the closed triangle represents the group in which $WT1_{187}$P1F peptide-pulsed B-LCL cells were used as a target cell. In FIG. 17b, the closed diamond represents the group in which K562 cells were used as a target cell, and the closed square represents the group in which 0206K562 cells, i.e., K562 cells made to endogenously present WT1 antigen peptides by transfection of the HLA-A*0206 gene thereinto, were used as a target cell.

The CTLs induced by stimulation with the $WT1_{187}$P1F peptide showed an equal cytotoxic activity against the $WT1_{187}$ peptide-pulsed B-LCL cells and the $WT1_{187}$P1F peptide-pulsed B-LCL cells, and the activity was stronger than that against the non-peptide-pulsed B-LCL cells (FIG. 17a). When HLA-A*0206-negative, WT1-positive K562 cells, and K562 cells made to endogenously present WT1 antigen peptides by transfection of the HLA-A*0206 gene thereinto (0206K562 cells) were used as a target cell, the CTLs induced by stimulation with the $WT1_{187}$P1F peptide showed a stronger cytotoxic activity against the 0206K562 cells than against the K562 cells (FIG. 17b). As is clear from the results, the CTLs induced by stimulation with the $WT1_{187}$P1F peptide can recognize both of the $WT1_{187}$P1F peptide and the wild-type $WT1_{187}$ peptide. Similarly, it was found that the CTLs are restricted by HLA-A*0206, and show the cytotoxic activity by recognizing the wild-type $WT1_{187}$ peptide presented endogenously.

Figure 18:
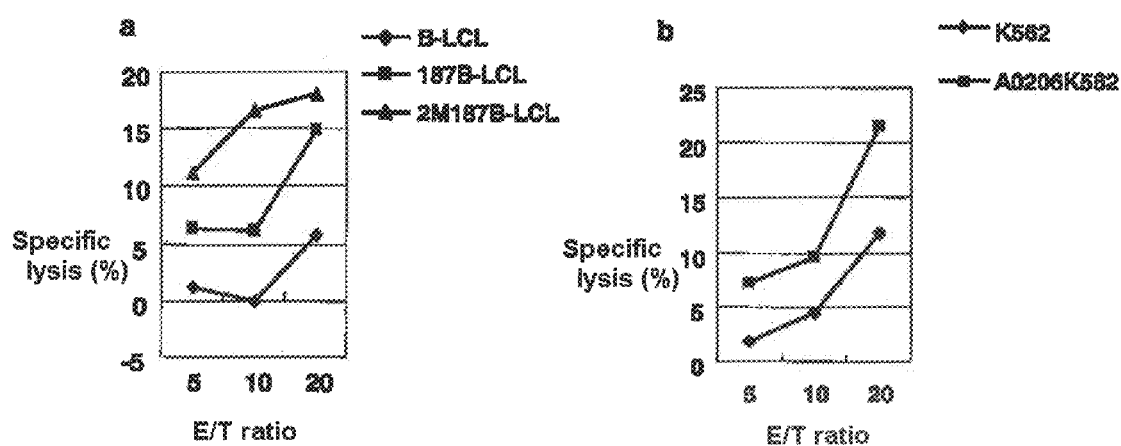
FIG. 18 shows the measurement results of the cytotoxic activity of CTLs induced by stimulation of PBMCs from an HLA-A*0206-positive donor with the $WT1_{187}P2M$ peptide.

FIG. 18 shows the measurement results of the cytotoxic activity of CTLs induced by stimulation of PBMCs from the HLA-A*0206-positive donor with the $WT1_{187}$P2M peptide. In FIG. 18, the vertical axis represents the cytotoxic activity, and the horizontal axis represents the ratio of CD8-positive T cells obtained by peptide stimulation (effector: E) relative to target cells (target: T) (E/T ratio). In FIG. 18a, the closed diamond represents the group in which B-LCL cells were used as a target cell, the closed square represents the group in which $WT1_{187}$ peptide-pulsed B-LCL cells were used as a target cell, and the closed triangle represents the group in which $WT1_{187}$P2M peptide-pulsed B-LCL cells were used as a target cell. In FIG. 18b, the closed diamond represents the group in which K562 cells were used as a target cell, and the closed square represents the group in which 0206K562 cells, i.e., K562 cells made to endogenously present WT1 antigen peptides by transfection of the HLA-A*0206 gene thereinto, were used as a target cell.

The CTLs induced by stimulation with the $WT1_{187}$P2M peptide showed an equal cytotoxic activity against the $WT1_{187}$ peptide-pulsed B-LCL cells and the $WT1_{187}$P2M peptide-pulsed B-LCL cells, and the activity was stronger than that against the non-peptide-pulsed B-LCL cells (FIG. 18a). When HLA-A*0206-negative, WT1-positive K562 cells, and K562 cells made to endogenously present WT1 antigen peptides by transfection of the HLA-A*0206 gene thereinto (0206K562 cells) were used as a target cell, the CTLs induced by stimulation with the WT1$_{187}$P2M peptide showed a stronger cytotoxic activity against the 0206K562 cells than against the K562 cells (FIG. 18b). As is clear from the results, the CTLs induced by stimulation with the WT1$_{187}$P2M peptide can recognize both of the WT1$_{187}$P2M peptide and the wild-type WT1$_{187}$ peptide. Similarly, it was found that the CTLs are restricted by HLA-A*0206, and show the cytotoxic activity by recognizing the wild-type WT1$_{187}$ peptide presented endogenously.

As is clear from the results of Examples 9 to 12, the CTLs induced by stimulation with the modified WT1$_{126}$ peptide, i.e., the WT1$_{126}$P1F peptide, the WT1$_{126}$P2L peptide, the WT1$_{126}$P3M peptide or the WT1$_{126}$P9V peptide, are restricted by HLA-A*0206, and show the cytotoxic activity by recognizing the wild-type WT1$_{126}$ peptide presented endogenously. Inter alia, the WT1$_{126}$P9V peptide, the WT1$_{126}$P2L peptide and the WT1$_{126}$P3M peptide were highly effective.

As is clear from the above results, the CTLs induced by stimulation with the modified WT1$_{187}$ peptide, i.e., the WT1$_{187}$P1F peptide, the WT1$_{187}$P2M peptide or the WT1$_{187}$P3M peptide, are restricted by HLA-A*0206, and show the cytotoxic activity by recognizing the wild-type WT1$_{187}$ peptide presented endogenously. Inter alia, the WT1$_{187}$P2M peptide and the WT1$_{187}$P1F peptide were highly effective.

Therefore, it was shown that these modified peptides are effective in treatment and prevention of cancers accompanied by increased expression of the WT1 gene in HLA-A*0206-positive persons.

As is clear from the above results, the CTLs induced by stimulation with the modified WT1$_{126}$ peptide, i.e., the WT1$_{126}$P1F peptide, the WT1$_{126}$P2L peptide, the WT1$_{126}$P3M peptide or the WT1$_{126}$P9V peptide, are restricted by HLA-A*0201, and show the cytotoxic activity by recognizing the wild-type WT1$_{126}$ peptide presented endogenously. Inter alia, the WT1$_{126}$P1F peptide and the WT1$_{126}$P2L peptide were highly effective.

As is clear from the above results, the CTLs induced by stimulation with the modified WT1$_{187}$ peptide, i.e., the WT1$_{187}$P1F peptide, the WT1$_{187}$P2M peptide or the WT1$_{187}$P3M peptide, are restricted by HLA-A*0201, and show the cytotoxic activity by recognizing the wild-type WT1$_{187}$ peptide presented endogenously. Inter alia, the WT1$_{187}$P2M peptide and the WT1$_{187}$P1F peptide were highly effective. Therefore, it was shown that these modified peptides are effective in treatment and prevention of cancers accompanied by increased expression of the WT1 gene in HLA-A*0201-positive persons.

Example 13

Synthesis of WT1$_{187}$P2V Peptide (SVGEQQYSV; SEQ ID NO: 13; H-Ser-Val-Gly-Glu-Gln-Gln-Tyr-Ser-Val-OH) (SEQ ID NO: 13))

1. Synthesis of Protected Peptide Resin (H-Ser(tBu)-Val-Gly-Glu(OtBu)-Gln(Trt)-Gln(Trt)-Tyr(tBu)-Ser(tBu)-Val-Alko-Resin) (SEQ ID NO: 79))

0.4 g of an Fmoc-Val-Alko-resin (Alko is p-alkoxybenzyl alcohol) (manufactured by WATANABE CHEMICAL INDUSTRIES, LTD; 0.80 mmol/g) was placed into the reaction vessel of the ACT496 solid-phase synthesizer manufactured by Advanced ChemTech, washed with DMF(N,N'-dimethylformamide) (Step 1), treated with a 25% solution of piperidine in DMF (5 minutes×1 time, and 30 minutes×1 time) to remove the Fmoc group (Step 2), and was again washed with DMF (Step 3) to give an H-Val-Alko-resin. To this reaction vessel, 0.7 mL of NMP (N-methylpyrrolidinone) and a solution of 121 mg (0.96 mmol) of DIPCI (N,N'-diisopropylcarbodiimide) in 0.9 mL of NMP, and then a solution of 368 mg (0.96 mmol) of Fmoc-Ser(tBu)-OH and 147 mg (0.96 mmol) of HOBT (1-hydroxybenzotriazol) monohydrate in 1.8 mL of NMP were added. Coupling reaction was performed at room temperature for 60 minutes (Step 4). Additional coupling reaction was performed using the same amounts of Fmoc-Ser(tBu)-OH, HOBT monohydrate and DIPCI as above (Step 5). The resulting resin was washed with DMF (Step 6), deprotected (Step 7) and washed again (Step 8) to give an H-Ser(tBu)-Val-Alko-resin. Then, couplings were successively performed by repeating Steps 4 to 8 using Fmoc-Tyr(tBu)-OH, Fmoc-Gln(Trt)-OH, Fmoc-Gln(Trt)-OH, Fmoc-Glu(OtBu)-OH, Fmoc-Gly-OH, Fmoc-Val-OH and Fmoc-Ser(tBu)-OH. The resulting peptide resin was collected from the reaction vessel, washed with ether and then dried in vacuo to give 980 mg of an H-Ser(tBu)-Val-Gly-Glu(OtBu)-Gln(Trt)-Gln(Trt)-Tyr(tBu)-Ser(tBu)-Val-Alko-resin. (SEQ ID NO: 79)). The outline of the synthesis process mentioned above is shown in Table 6.

<Synthesis Process>

TABLE 6

| Step | Reagent | Repetition (time) | Duration (min) |
|---|---|---|---|
| 1) washing | DMF 3 mL | 5 | 0.3 |
| 2) deprotection | 25% piperidine/DMF 3 mL | 1 | 5 |
|  |  | 1 | 30 |
| 3) washing | DMF 3 mL | 5 | 0.3 |
| 4) coupling | Each Fmoc-amino acid (3 Eq), HOBT (3 Eq), DIPCI (3 Eq)/NMP 3.4 mL | 1 | 60 |
| 5) coupling | Each Fmoc-amino acid (3 Eq), HOBT (3 Eq), DIPCI (3 Eq)/NMP 3.4 mL | 1 | 60 |
| 6) washing | DMF 3 mL | 5 | 0.3 |
| 7) deprotection | 25% piperidine/DMF 3 mL | 1 | 5 |
|  |  | 1 | 30 |
| 8) washing | DMF 3 mL | 5 | 0.3 |

2. Deprotection of Protected Peptide Resin

To 980 mg of the H-Ser(tBu)-Val-Gly-Glu(OtBu)-Gln(Trt)-Gln(Trt)-Tyr(tBu)-Ser(tBu)-Val-Alko-resin (SEQ ID NO: 79))was added 5 mL of a mixed solution of trifluoroacetic acid/water/triisopropylsilane (95/2.5/2.5 (volume ratio)). The mixture was stirred at room temperature for 2.5 hours. The resin was filtered off and the resulting filtrate was added to ice-cold diethyl ether. The resulting precipitate was collected with a glass filter. The residue was washed with diethyl ether and dried in vacuo to give 268 mg of a crude peptide.

3. Purification of Crude Peptide 268 mg of the obtained crude peptide was dissolved in a 20% aqueous acetic acid solution, and purified by reverse phase liquid chromatography.
Pump: Shimadzu LC-8A
Column: YMC-Pack Pro C18 AS12S11-2530WT 3 cmΦ×25 cm
Eluent 1: H$_2$O/0.1% TFA
Eluent 2 (the second eluent): CH$_3$CN/0.1% TFA
Flow rate: 10 mL/min
Detection: UV220 nm After equilibrated with the second eluent at a concentration of 1%, the column was loaded with the crude peptide solution.

After that, the concentration of the second eluent was allowed to increase to 8% over 30 minutes and subsequently to 14% over 120 minutes. Fractions containing the objective compound were collected, acetonitrile was evaporated off in vacuo and then the residue was freeze-dried. Thus, 105 mg of the objective WT1$_{187}$P2V peptide (SVGEQQYSV; SEQ ID NO: 13; H-Ser-Val-Gly-Glu-Gln-Gln-Tyr-Ser-Val-OH) (SEQ ID NO: 13))was obtained.

The conditions used for HPLC analysis and mass spectrometry of the purified peptide are as follows.
HPLC analysis (Shimadzu LC-10Avp)
Column: YMC-Pack Pro C18 AS-302 4.6 mmΦ×150 mm
Eluent 1: H$_2$O/0.1% TFA
Eluent 2: CH$_3$CN/0.1% TFA
Gradient: The concentration of eluent 2 was allowed to increase from 10% to 40% over 30 minutes.
Flow rate: 1 mL/min
Detection: UV220 nm
Purity: 97.4%, Retention time: 11.22 minutes
Amino acid analysis (Hitachi L-8500 Amino acid analyzer)
Hydrolysis: 1% phenol/6N aqueous hydrochloric acid solution, 110° C., 24 hour
Analysis method: Ninhydrin method
Ser:1.78(2) Glx:3.26(3) * Gly:(1) Val:2.04(2) Tyr:1.06(1) *)
  Gly=standard amino acid, the number in parentheses is a theoretical value.
Mass spectrometry (Applied Biosystems API 150EX Mass spectrometer)
m/z=996.9 [M+1]$^+$ (theoretical value=996.5)
Amino acid sequence analysis (Applied Biosystems 491 Protein sequencer)

The amino acid sequence was checked sequentially from the N terminal Ser to the C terminal Val.

The peptides shown in Tables 7 and 8 were synthesized in the same manner as above.

TABLE 7

| Peptide | Amino acid sequence | SEQ ID NO | Amount of crude peptide obtained (mg) | Amount of purified peptide obtained (mg) | HPLC purity (%) | HPLC retention time (min) | Mass spectrometry (m/z) |
|---|---|---|---|---|---|---|---|
| WT1$_{187}$P2Q | SQGEQQYSV | 14 | 251 | 88 | 98.2 | 9.21 | 1026.0 |
| WT1$_{187}$P2I | SIGEQQYSV | 15 | 244 | 91 | 97.6 | 12.98 | 1010.7 |
| WT1$_{187}$P2M | SMGEQQYSV | 16 | 260 | 22 | 96.9 | 11.91 | 1029.1 |
| WT1$_{187}$P3L | SLLEQQYSV | 17 | 238 | 176 | 96.8 | 18.24 | 1066.9 |
| WT1$_{187}$P3A | SLAEQQYSV | 18 | 268 | 172 | 99.1 | 13.67 | 1024.8 |
| WT1$_{187}$P3V | SLVEQQYSV | 19 | 267 | 182 | 98.7 | 15.26 | 1052.8 |
| WT1$_{187}$P3M | SLMEQQYSV | 20 | 280 | 63 | 94.8 | 16.12 | 1084.8 |
| WT1$_{187}$P3P | SLPEQQYSV | 21 | 227 | 132 | 98.1 | 14.02 | 1050.8 |
| WT1$_{187}$P3W | SLWEQQYSV | 22 | 248 | 40 (of crude peptide 100 mg) | 99.4 | 20.00 | 1139.5 |
| WT1$_{187}$P3F | SLFEQQYSV | 23 | 224 | 110 | 98.3 | 19.44 | 1100.8 |
| WT1$_{187}$P3Y | SLYEQQYSV | 24 | 236 | 114 | 98.5 | 15.76 | 1116.7 |
| WT1$_{187}$P3S | SLSEQQYSV | 25 | 261 | 130 | 99.1 | 13.33 | 1040.8 |
| WT1$_{187}$P3I | SLIEQQYSV | 26 | 270 | 162 | 97.3 | 17.51 | 1066.9 |

TABLE 8

| Peptide | Amino acid sequence | SEQ ID NO | Amount of crude peptide obtained (mg) | Amount of purified peptide obtained (mg) | HPLC purity (%) | HPLC retention time (min) | Mass spectrometry (m/z) |
|---|---|---|---|---|---|---|---|
| WT1$_{126}$P2V | RVFPNAPYL | 36 | 253 | 130 | 96.5 | 20.65 | 1077.1 |
| WT1$_{126}$P2Q | RQFPNAPYL | 37 | 274 | 87 | 98.7 | 18.43 | 1106.1 |
| WT1$_{126}$P2A | RAFPNAPYL | 38 | 240 | 63 | 99.0 | 19.03 | 1049.1 |
| WT1$_{126}$P9A | RMFPNAPYA | 50 | 262 | 139 | 94.3 | 16.59 | 1066.8 |
| WT1$_{126}$P9M | RMFPNAPYM | 52 | 295 | 167 | 95.7 | 19.75 | 1126.8 |

The peptides shown in Tables 9 to 12 were similarly synthesized, but the conditions used for HPLC analysis and mass spectrometry of the purified peptides are as follows.

HPLC analysis (Agilent HP1100 or Thermo Fisher Scientific Surveyor)
Column: Thermo Fischer Scientific BioBasic-18 3 mmΦ× 250 mm
Eluent 1: $H_2O$/0.1% TFA
Eluent 2: $CH_3CN$/0.1% TFA
Gradient: The concentration of eluent 2 was allowed to change to the concentration shown in the table over 20 minutes.
Flow rate: 0.4 mL/min
Detection: 215 nm
Mass Spectrometry
Thermo Bioanalysis Dynamo Mass Spectrometer (MALDI-TOF)

TABLE 9

| Peptide | Amino acid sequence | SEQ ID NO | HPLC purity (%) | HPLC retention time (min) | HPLC gradient | Mass spectrometry (m/z) |
|---|---|---|---|---|---|---|
| $WT1_{187}$P1G | GLGEQQYSV | 4 | 100 | 12.72 | 5-60% | 980.7 |
| $WT1_{187}$P1A | ALGEQQYSV | 5 | 98.9 | 12.00 | 10-50% | 993.0 |
| $WT1_{187}$P1V | VLGEQQYSV | 6 | 98.9 | 14.98 | 5-50% | 1022.3 |
| $WT1_{187}$P1L | LLGEQQYSV | 7 | 97.6 | 12.75 | 10-65% | 1037.6 |
| $WT1_{187}$P1I | ILGEQQYSV | 8 | 98.8 | 13.46 | 5-60% | 1037.2 |
| $WT1_{187}$P1M | MLGEQQYSV | 9 | 95.5 | 14.15 | 5-60% | 1054.0 |
| $WT1_{187}$P1W | WLGEQQYSV | 10 | 98.9 | 15.60 | 5-60% | 1109.9 |
| $WT1_{187}$P1F | FLGEQQYSV | 11 | 95.8 | 13.14 | 10-65% | 1070.8 |
| $WT1_{187}$P9L | SLGEQQYSL | 53 | 95.4 | 12.49 | 10-55% | 1024.6 |

TABLE 10

| Peptide | Amino acid sequence | SEQ ID NO | HPLC purity (%) | HPLC retention time (min) | HPLC gradient | Mass spectrometry (m/z) |
|---|---|---|---|---|---|---|
| $WT1_{126}$P1G | GMFPNAPYL | 27 | 99.6 | 15.39 | 10-70% | 1009.5 |
| $WT1_{126}$P1A | AMFPNAPYL | 28 | 98.8 | 13.79 | 10-85% | 1023.3 |
| $WT1_{126}$P1V | VMFPNAPYL | 29 | 98.4 | 14.00 | 10-85% | 1052.2 |
| $WT1_{126}$P1L | LMFPNAPYL | 30 | 98.9 | 14.91 | 10-80% | 1066.3 |
| $WT1_{126}$P1I | IMFPNAPYL | 31 | 99.2 | 13.93 | 10-80% | 1065.4 |
| $WT1_{126}$P1M | MMFPNAPYL | 32 | 100 | 13.77 | 10-80% | 1083.5 |
| $WT1_{126}$P1W | WMFPNAPYL | 33 | 97.5 | 15.64 | 10-80% | 1139.3 |
| $WT1_{126}$P1F | FMFPNAPYL | 34 | 98.8 | 14.78 | 10-85% | 1099.7 |
| $WT1_{126}$P2L | RLFPNAPYL | 39 | 98.6 | 13.11 | 10-80% | 1090.9 |
| $WT1_{126}$P2I | RIFPNAPYL | 40 | 100 | 13.74 | 10-70% | 1090.1 |
| $WT1_{126}$P3I | RMIPNAPYL | 41 | 97.4 | 14.17 | 10-70% | 1076.7 |
| $WT1_{126}$P3L | RMLPNAPYL | 42 | 100 | 13.88 | 10-65% | 1076.4 |
| $WT1_{126}$P3G | RMGPNAPYL | 43 | 96.7 | 12.63 | 10-65% | 1020.9 |
| $WT1_{126}$P3A | RMAPNAPYL | 44 | 95.2 | 13.95 | 10-60% | 1034.9 |
| $WT1_{126}$P3V | RMVPNAPYL | 45 | 92.9 | 14.67 | 10-60% | 1062.7 |
| $WT1_{126}$P3M | RMMPNAPYL | 46 | 91.8 | 14.87 | 10-60% | 1094.8 |
| $WT1_{126}$P3P | RMPPNAPYL | 47 | 95.8 | 13.56 | 10-65% | 1058.8 |
| $WT1_{126}$P3W | RMWPNAPYL | 48 | 99.6 | 15.21 | 10-70% | 1149.7 |

TABLE 10-continued

| Peptide | Amino acid sequence | SEQ ID NO | HPLC purity (%) | HPLC retention time (min) | HPLC gradient | Mass spectrometry (m/z) |
|---|---|---|---|---|---|---|
| WT1₁₂₆P9V | RMFPNAPYV | 49 | 99.2 | 13.86 | 10-60% | 1096.5 |
| WT1₁₂₆P9I | RMFPNAPYI | 51 | 99.4 | 14.00 | 10-65% | 1110.7 |

TABLE 11

| Peptide | Amino acid sequence | SEQ ID NO | HPLC purity (%) | HPLC retention time (min) | HPLC gradient | Mass spectrometry (m/z) |
|---|---|---|---|---|---|---|
| WT1₁₈₇P1D | DLGEQQYSV | 54 | 96.6 | 13.43 | 5-60% | 1038.2 |
| WT1₁₈₇P1E | ELGEQQYSV | 55 | 96.4 | 11.83 | 10-60% | 1052.2 |
| WT1₁₈₇P1H | HLGEQQYSV | 56 | 98.0 | 15.79 | 5-40% | 1060.2 |
| WT1₁₈₇P1K | KLGEQQYSV | 57 | 99.0 | 13.77 | 5-45% | 1052.2 |
| WT1₁₈₇P1N | NLGEQQYSV | 58 | 95.8 | 14.34 | 5-50% | 1037.0 |
| WT1₁₈₇P1P | PLGEQQYSV | 59 | 95.9 | 14.68 | 5-50% | 1020.0 |
| WT1₁₈₇P1Q | QLGEQQYSV | 60 | 96.8 | 13.28 | 5-60% | 1051.3 |
| WT1₁₈₇P1R | RLGEQQYSV | 61 | 100 | 13.27 | 5-60% | 1079.6 |
| WT1₁₈₇P1T | TLGEQQYSV | 62 | 96.7 | 14.40 | 5-50% | 1025.0 |

TABLE 12

| Peptide | Amino acid sequence | SEQ ID NO | HPLC purity (%) | HPLC retention time (min) | HPLC gradient | Mass spectrometry (m/z) |
|---|---|---|---|---|---|---|
| WT1₁₂₆P1D | DMFPNAPYL | 63 | 99.2 | 14.72 | 10-75% | 1067.3 |
| WT1₁₂₆P1E | EMFPNAPYL | 64 | 99.1 | 15.20 | 5-70% | 1082.1 |
| WT1₁₂₆P1H | HMFPNAPYL | 65 | 96.7 | 14.52 | 10-70% | 1089.9 |
| WT1₁₂₆P1K | KMFPNAPYL | 66 | 95.9 | 13.96 | 10-75% | 1080.0 |
| WT1₁₂₆P1N | NMFPNAPYL | 67 | 99.8 | 14.69 | 10-75% | 1066.3 |
| WT1₁₂₆P1P | PMFPNAPYL | 68 | 96.9 | 14.26 | 10-80% | 1049.3 |
| WT1₁₂₆P1Q | QMFPNAPYL | 69 | 95.1 | 14.94 | 10-70% | 1080.3 |
| WT1₁₂₆P1S | SMFPNAPYL | 70 | 99.8 | 14.28 | 10-80% | 1040.8 |
| WT1₁₂₆P1T | TMFPNAPYL | 71 | 98.8 | 13.72 | 10-85% | 1053.5 |
| WT1₁₂₆P2I&P9I | RIFPNAPYI | 72 | 97.0 | 14.23 | 10-65% | 1089.5 |
| WT1₁₂₆P2I&P9V | RIFPNAPYV | 73 | 100 | 12.23 | 10-80% | 1077.0 |
| WT1₁₂₆P2L&P9I | RLFPNAPYI | 74 | 97.7 | 13.43 | 10-75% | 1090.8 |
| WT1₁₂₆P2L&P9V | RLFPNAPYV | 75 | 97.0 | 12.83 | 10-75% | 1076.9 |

Example 14

Evaluation of Modified Peptides on the Activity of Inducing Specific Immune Cells Using HLA-A*0201-Expressing Transgenic Mice, and Confirmation of Cross Reactivity of Induced Specific Immune Cells to the Wild-Type Peptide <Methods>
(1) Modified Peptide Candidates As for the $WT1_{187}$ peptide, the $WT1_{126}$ peptide, and modified peptides thereof (peptides comprising substitution of one or two amino acid residues at position 1, 2, 3 and/or 9 from the N terminus of the $WT1_{187}$ peptide or the $WT1_{126}$ peptide), the affinity against HLA-A*0201 molecules was analyzed using the known method in the technical field, i.e., the method mediated by the following four computer databases: BIMAS, SYFPEITHI, RANLPEP, and NetMHC3.0. The analysis results of the $WT1_{187}$ peptide and its modified peptides are shown in Tables 13 to 16 and 21. The analysis results of the $WT1_{126}$ peptide and its modified peptides are shown in Tables 17 to 20 and 22 to 23. The predicted affinity is shown in scores.

TABLE 13

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| $WT1_{187}$ | SLGEQQYSV | 2 | 285 | 27 | 96/64.43% | 0.721 |
| $WT1_{187}$P1A | ALGEQQYSV | 5 | 285 | 27 | 95/63.76% | 0.720 |
| $WT1_{187}$P1F | FLGEQQYSV | 11 | 1312 | 26 | 82/55.03% | 0.862 |
| $WT1_{187}$P1G | GLGEQQYSV | 4 | 285 | 26 | 86/57.72% | 0.672 |
| $WT1_{187}$P1I | ILGEQQYSV | 8 | 485 | 27 | 90/60.40% | 0.698 |
| $WT1_{187}$P1L | LLGEQQYSV | 7 | 485 | 27 | 89/59.73% | 0.719 |
| $WT1_{187}$P1M | MLGEQQYSV | 9 | 485 | 25 | 92/61.74% | 0.770 |
| $WT1_{187}$P1V | VLGEQQYSV | 6 | 485 | 26 | 92/61.74% | 0.705 |
| $WT1_{187}$P1W | WLGEQQYSV | 10 | 1312 | 25 | 71/47.65% | 0.693 |

TABLE 14

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| $WT1_{187}$ | SLGEQQYSV | 2 | 285 | 27 | 96/64.43% | 0.721 |
| $WT1_{187}$P2I | SIGEQQYSV | 15 | 39 | 25 | 85/57.05% | 0.556 |
| $WT1_{187}$P2M | SMGEQQYSV | 16 | 206 | 25 | 84/56.38% | 0.740 |
| $WT1_{187}$P2Q | SQGEQQYSV | 14 | 29 | 17 | 52/34.90% | 0.455 |
| $WT1_{187}$P2V | SVGEQQYSV | 13 | 25 | 21 | 78/52.35% | 0.461 |

TABLE 15

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| $WT1_{187}$ | SLGEQQYSV | 2 | 285 | 27 | 96/64.43% | 0.721 |
| $WT1_{187}$P3A | SLAEQQYSV | 18 | 285 | 29 | 110/73.83% | 0.811 |
| $WT1_{187}$P3F | SLFEQQYSV | 23 | 1055 | 28 | 114/76.51% | 0.852 |
| $WT1_{187}$P3I | SLIEQQYSV | 26 | 285 | 29 | 115/77.18% | 0.817 |
| $WT1_{187}$P3L | SLLEQQYSV | 17 | 1055 | 29 | 116/77.85% | 0.839 |
| $WT1_{187}$P3M | SLMEQQYSV | 20 | 1055 | 28 | 114/76.51% | 0.876 |
| $WT1_{187}$P3P | SLPEQQYSV | 21 | 285 | 27 | 95/63.76% | 0.748 |

TABLE 15-continued

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{187}$P3S | SLSEQQYSV | 25 | 285 | 27 | 110/73.83% | 0.793 |
| WT1$_{187}$P3V | SLVEQQYSV | 19 | 285 | 27 | 113/75.84% | 0.766 |
| WT1$_{187}$P3W | SLWEQQYSV | 22 | 2367 | 28 | 98/65.77% | 0.863 |
| WT1$_{187}$P3Y | SLYEQQYSV | 24 | 913 | 28 | 111/74.50% | 0.854 |

TABLE 16

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{187}$ | SLGEQQYSV | 2 | 285 | 27 | 96/64.43% | 0.721 |
| WT1$_{187}$P9L | SLGEQQYSL | 53 | 88 | 27 | 89/59.73% | 0.640 |

TABLE 17

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{126}$ | RMFPNAPYL | 3 | 314 | 22 | 70/46.98% | 0.802 |
| WT1$_{126}$P1A | AMFPNAPYL | 28 | 314 | 24 | 77/51.68% | 0.808 |
| WT1$_{126}$P1F | FMFPNAPYL | 34 | 1444 | 23 | 64/42.95% | 0.909 |
| WT1$_{126}$P1G | GMFPNAPYL | 27 | 314 | 23 | 68/45.64% | 0.795 |
| WT1$_{126}$P1I | IMFPNAPYL | 31 | 534 | 24 | 72/48.32% | 0.802 |
| WT1$_{126}$P1L | LMFPNAPYL | 30 | 534 | 24 | 71/47.65% | 0.819 |
| WT1$_{126}$P1M | MMFPNAPYL | 32 | 534 | 22 | 74/49.66% | 0.852 |
| WT1$_{126}$P1V | VMFPNAPYL | 29 | 534 | 23 | 74/49.66% | 0.804 |
| WT1$_{126}$P1W | WMFPNAPYL | 33 | 1444 | 22 | 53/35.57% | 0.799 |

TABLE 18

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{126}$ | RMFPNAPYL | 3 | 314 | 22 | 70/46.98% | 0.802 |
| WT1$_{126}$P2A | RAFPNAPYL | 38 | 6 | 18 | 47/31.54% | 0.376 |
| WT1$_{126}$P2I | RIFPNAPYL | 40 | 60 | 22 | 71/47.65% | 0.640 |
| WT1$_{126}$P2L | RLFPNAPYL | 39 | 435 | 24 | 82/55.03% | 0.784 |
| WT1$_{126}$P2Q | RQFPNAPYL | 37 | 44 | 14 | 38/25.50% | 0.485 |
| WT1$_{126}$P2V | RVFPNAPYL | 36 | 38 | 18 | 64/42.95% | 0.552 |

TABLE 19

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{126}$ | RMFPNAPYL | 3 | 314 | 22 | 70/46.98% | 0.802 |
| WT1$_{126}$P3A | RMAPNAPYL | 44 | 85 | 23 | 66/44.30% | 0.734 |
| WT1$_{126}$P3G | RMGPNAPYL | 43 | 85 | 21 | 52/34.90% | 0.602 |
| WT1$_{126}$P3I | RMIPNAPYL | 41 | 85 | 23 | 71/47.65% | 0.741 |
| WT1$_{126}$P3L | RMLPNAPYL | 42 | 314 | 23 | 72/48.32% | 0.781 |
| WT1$_{126}$P3M | RMMPNAPYL | 46 | 314 | 22 | 70/46.98% | 0.834 |
| WT1$_{126}$P3P | RMPPNAPYL | 47 | 85 | 21 | 51/34.23% | 0.613 |
| WT1$_{126}$P3V | RMVPNAPYL | 45 | 85 | 21 | 69/46.31% | 0.680 |
| WT1$_{126}$P3W | RMWPNAPYL | 48 | 2293 | 22 | 61/40.94% | 0.867 |

TABLE 20

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{126}$ | RMFPNAPYL | 3 | 314 | 22 | 70/46.98% | 0.802 |
| WT1$_{126}$P9A | RMFPNAPYA | 50 | 73 | 16 | 53/35.57% | 0.731 |
| WT1$_{126}$P9I | RMFPNAPYI | 51 | 153 | 20 | 74/49.66% | 0.790 |
| WT1$_{126}$P9M | RMFPNAPYM | 52 | 73 | 16 | 65/43.62% | 0.686 |
| WT1$_{126}$P9V | RMFPNAPYV | 49 | 1022 | 22 | 77/51.68% | 0.838 |

TABLE 21

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{187}$ | SLGEQQYSV | 2 | 285 | 27 | 96/64.43% | 0.721 |
| WT1$_{187}$P1D | DLGEQQYSV | 54 | 21 | 24 | 81/54.36% | 0.252 |
| WT1$_{187}$P1E | ELGEQQYSV | 55 | 21 | 22 | 85/57.05% | 0.366 |
| WT1$_{187}$P1H | HLGEQQYSV | 56 | 10 | 25 | 83/55.70% | 0.610 |
| WT1$_{187}$P1K | KLGEQQYSV | 57 | 998 | 26 | 89/59.73% | 0.745 |
| WT1$_{187}$P1N | NLGEQQYSV | 58 | 285 | 25 | 90/60.40% | 0.613 |
| WT1$_{187}$P1P | PLGEQQYSV | 59 | 6 | 22 | 78/52.35% | 0.287 |
| WT1$_{187}$P1Q | QLGEQQYSV | 60 | 285 | 25 | 87/58.39% | 0.630 |
| WT1$_{187}$P1R | RLGEQQYSV | 61 | 285 | 25 | 88/59.06% | 0.690 |
| WT1$_{187}$P1T | TLGEQQYSV | 62 | 285 | 25 | 93/62.42% | 0.669 |

TABLE 22

| Peptide | Amino acid sequence | SEQ ID NO | HLA-A*0201 binding score | | | |
|---|---|---|---|---|---|---|
| | | | BIMAS | SYFPEITHI | RANKPEP | NetMHC3.0 |
| WT1$_{126}$ | RMFPNAPYL | 3 | 314 | 22 | 70/46.98% | 0.802 |
| WT1$_{126}$P1D | DMFPNAPYL | 63 | 24 | 21 | 63/42.28% | 0.353 |

TABLE 22-continued

| Peptide | Amino acid sequence | SEQ ID NO | BIMAS | SYFPEITHI | RANKPEP | NetMHC3.0 |
|---|---|---|---|---|---|---|
| WT1₁₂₆P1E | EMFPNAPYL | 64 | 24 | 19 | 67/44.97% | 0.501 |
| WT1₁₂₆P1H | HMFPNAPYL | 65 | 11 | 22 | 65/43.62% | 0.747 |
| WT1₁₂₆P1K | KMFPNAPYL | 66 | 1099 | 23 | 71/47.65% | 0.841 |
| WT1₁₂₆P1N | NMFPNAPYL | 67 | 314 | 22 | 72/48.32% | 0.734 |
| WT1₁₂₆P1P | PMFPNAPYL | 68 | 7 | 19 | 60/40.27% | 0.802 |
| WT1₁₂₆P1Q | QMFPNAPYL | 69 | 314 | 22 | 69/46.31% | 0.757 |
| WT1₁₂₆P1S | SMFPNAPYL | 70 | 314 | 24 | 78/52.35% | 0.819 |
| WT1₁₂₆P1T | TMFPNAPYL | 71 | 314 | 22 | 75/50.34% | 0.779 |

TABLE 23

| Peptide | Amino acid sequence | SEQ ID NO | BIMAS | SYFPEITHI | RANKPEP | NetMHC3.0 |
|---|---|---|---|---|---|---|
| WT1₁₂₆ | RMFPNAPYL | 3 | 314 | 22 | 70/46.98% | 0.802 |
| WT1₁₂₆P2I&P9I | RIFPNAPYI | 72 | 29 | 20 | 75/50.34% | 0.617 |
| WT1₁₂₆P2I&P9V | RIFPNAPYV | 73 | 195 | 22 | 78/52.35% | 0.722 |
| WT1₁₂₆P2L&P9I | RLFPNAPYI | 74 | 212 | 22 | 86/57.72% | 0.780 |
| WT1₁₂₆P2L&P9V | RLFPNAPYV | 75 | 1415 | 24 | 89/59.73% | 0.818 |

A modified peptide which was predicted to have an equal or higher affinity compared with the wild-type peptide (the WT1₁₈₇ peptide or the WT1₁₂₆ peptide) in at least one of the databases was selected as a sample to be tested in the following (2) to (4), in addition to wild-type peptides.

(2) Preparation and Administration of Peptide Preparations

A peptide synthesized and freeze-dried in Example 13 was prepared at the concentration of 40 mg/mL in DMSO (manufactured by Nacalai Tesque, Inc.). After that, 32.5 μL of the prepared DMSO solution of the peptide was mixed with 540 μL of distilled water for injection (manufactured by Otsuka Pharmaceutical Factory, Inc.). Next, 550 μL of the mixture was mixed with 700 μL of the Freund's incomplete adjuvant (Montanide ISA-51) using a glass syringe to prepare a water-in-oil emulsion. An HLA-A*0201-expressing transgenic mouse (strain name: HLA-A2+HLA-DR1+/Iaβ° β2m, EMMA ID number EM: 01783) was immunized by subcutaneous administration of 300 μL of the preparation (water-in-oil emulsion) into the base of the tail. The evaluation of each peptide was performed using 2 or 3 mice.

(3) Preparation of Splenic Cells

The spleen was isolated 7 days after immunization. The spleen was smashed by rubbing against the frothed part of a slide glass and then subjected to hemolysis treatment with ACK Lysing Buffer (manufactured by Lonza Co.) to prepare splenic cells. In this experiment, CTM (Complete T-cell Medium: RPMI-1640 medium (manufactured by Invitrogen Corporation) supplemented by 10% FBS, 10 mM HEPES, 20 mM L-glutamine, 1 mM sodium pyruvate, 1 mM MEM non-essential amino acid, 1% MEM vitamin and 55 μM 2-mercaptoethanol with the proviso that these concentrations were all final concentrations) was used as the medium for the splenic cells, and the cell suspension was prepared at the concentration of 5×10⁶ cells/mL.

(4) Elispot Method

Whether the administered peptide has the activity of inducing WT1-specific immune cells was examined by the ELISPOT method using IFNγ as an index. The method was performed according to the attached manual. After the CTM was added in a volume of 50 μL/well into plates for ELISPOT (manufactured by BD Japan, catalog No. 551083), the splenic cell suspension was plated therein in a volume of 100 μL (5×10⁵ cells/well). Further, the administered peptide or the wild-type peptide was added thereto in a volume of 50 μL/well (peptide final concentration: 2 μg/mL). This assay method is known as one of the substitute methods that enable prediction of cytotoxic activity (J. Immunological Methods, 1995, 181, 45-54).

<Results>

The evaluation results of the activity of inducing specific cell-mediated immunity are shown in FIGS. 19 to 22 and 28 to 29 for the modified WT1₁₈₇ peptides, and in FIGS. 23 to 27 and 30 to 32 for the modified WT1₁₂₆ peptides. In each of FIGS. 19 to 32, the vertical axis represents the number of antigen peptide-specific responsive cells in 5×10⁵ splenic cells (spots/5×10⁵ cells), and the horizontal axis represents the individual mouse (2 or 3 mice) used for evaluation. The white bar represents the number of the specific immune cells responded under no stimulation with antigen peptides. The gray bar represents the number of the specific immune cells responded to stimulation with the wild-type peptide. The black bar represents the number of the specific immune cells responded to stimulation with the administered (modified) peptide.

FIGS. 19 to 32 show the respective activities of inducing specific cell-mediated immunity regarding the following peptides.

Figure 19:
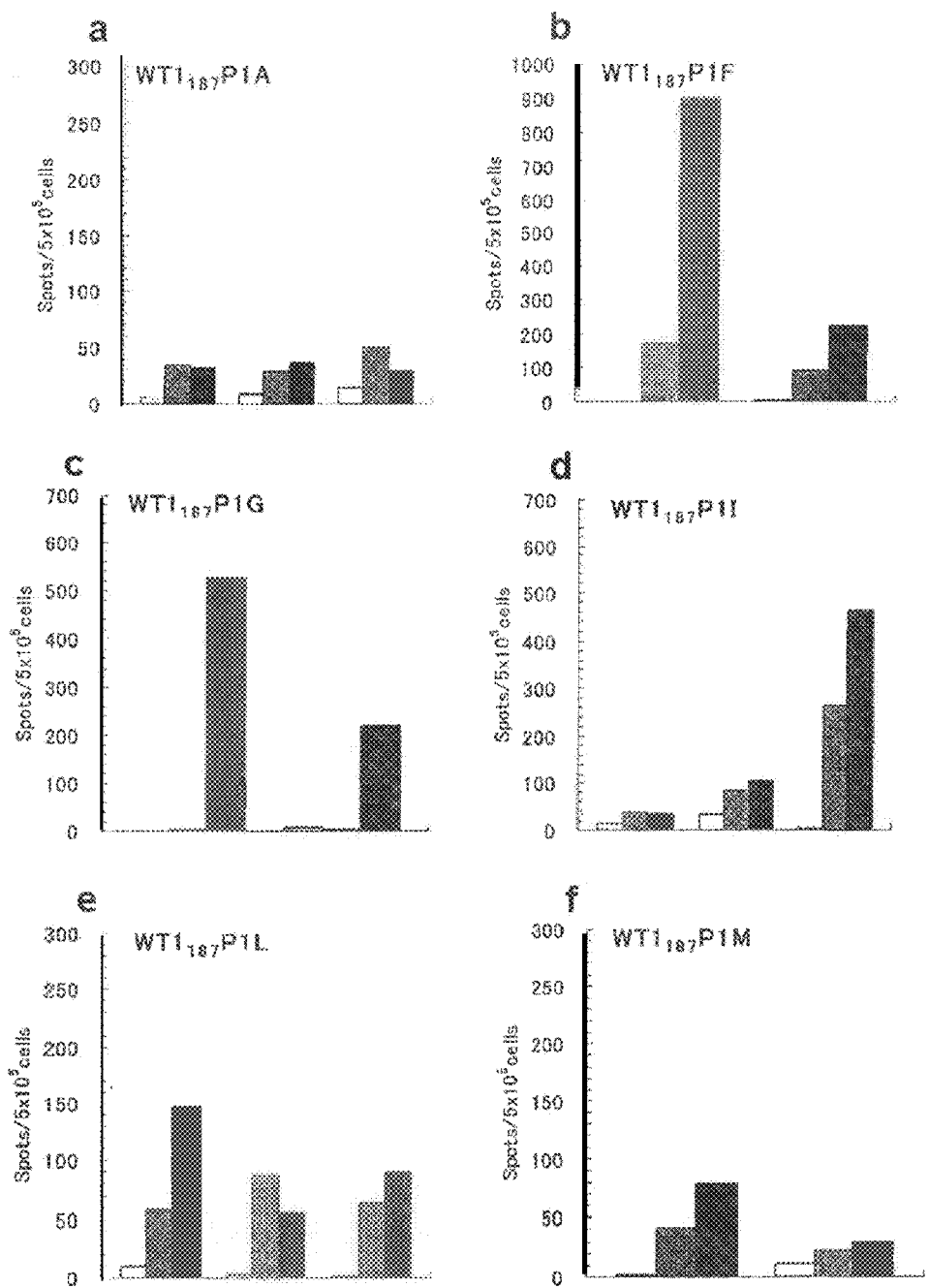
FIG. 19 shows the evaluation results of modified $WT1_{187}$ peptides on the activity of inducing specific cell-mediated immunity.

FIG. 19 a: $WT1_{187}P1A$ peptide, b: $WT1_{187}P1F$ peptide, c: $WT1_{187}P1G$ peptide, d: $WT1_{187}P1I$ peptide, e: $WT1_{187}P1L$ peptide, f: $WT1_{187}P1M$ peptide.

Figure 20:
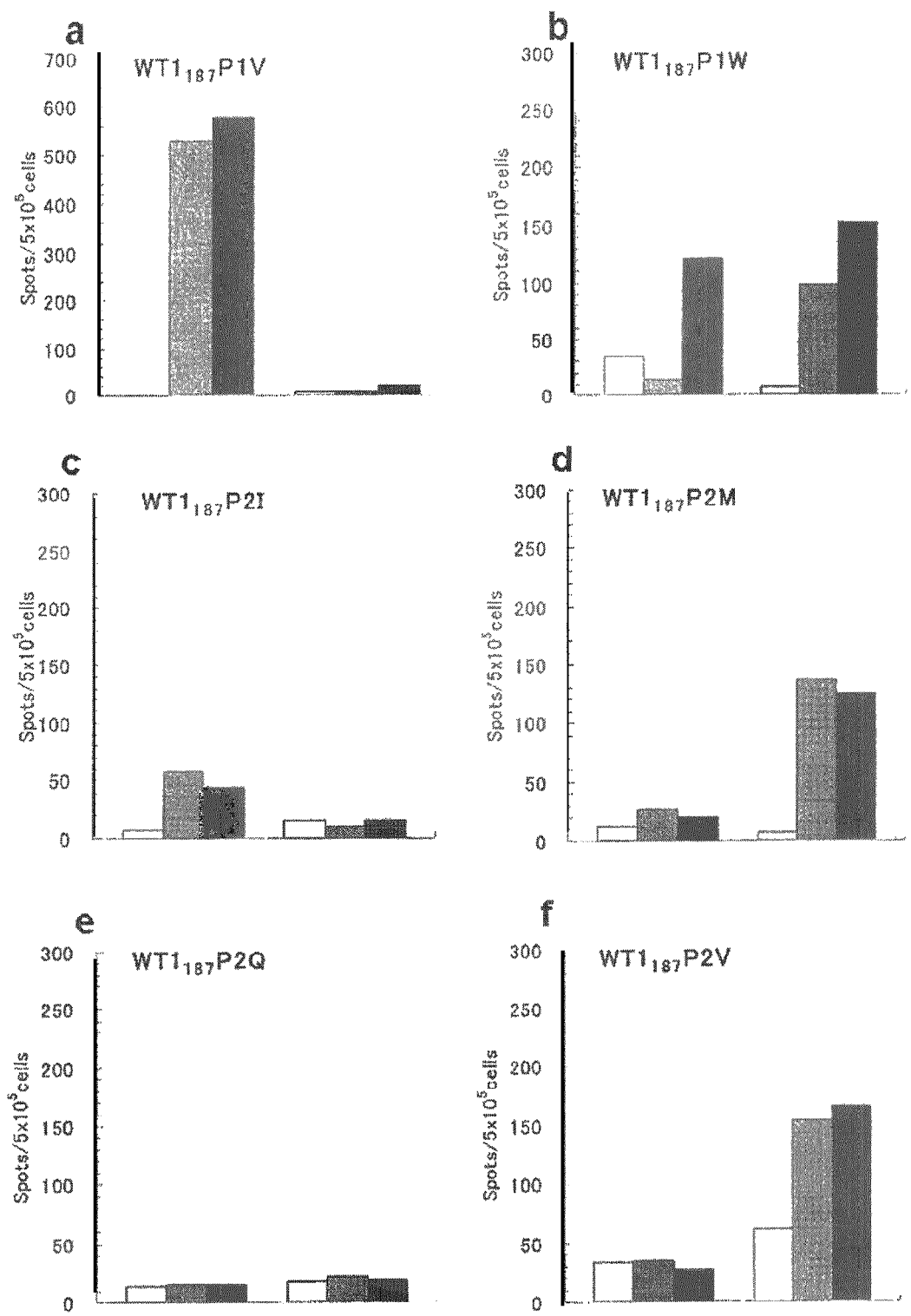
FIG. 20 shows the evaluation results of modified $WT1_{187}$ peptides on the activity of inducing specific cell-mediated immunity.

FIG. 20 a: $WT1_{187}P1V$ peptide, b: $WT1_{187}P1W$ peptide, c: $WT1_{187}P2I$ peptide, d: $WT1_{187}P2M$ peptide, e: $WT1_{187}P2Q$ peptide, f: $WT1_{187}P2V$ peptide.

Figure 21:
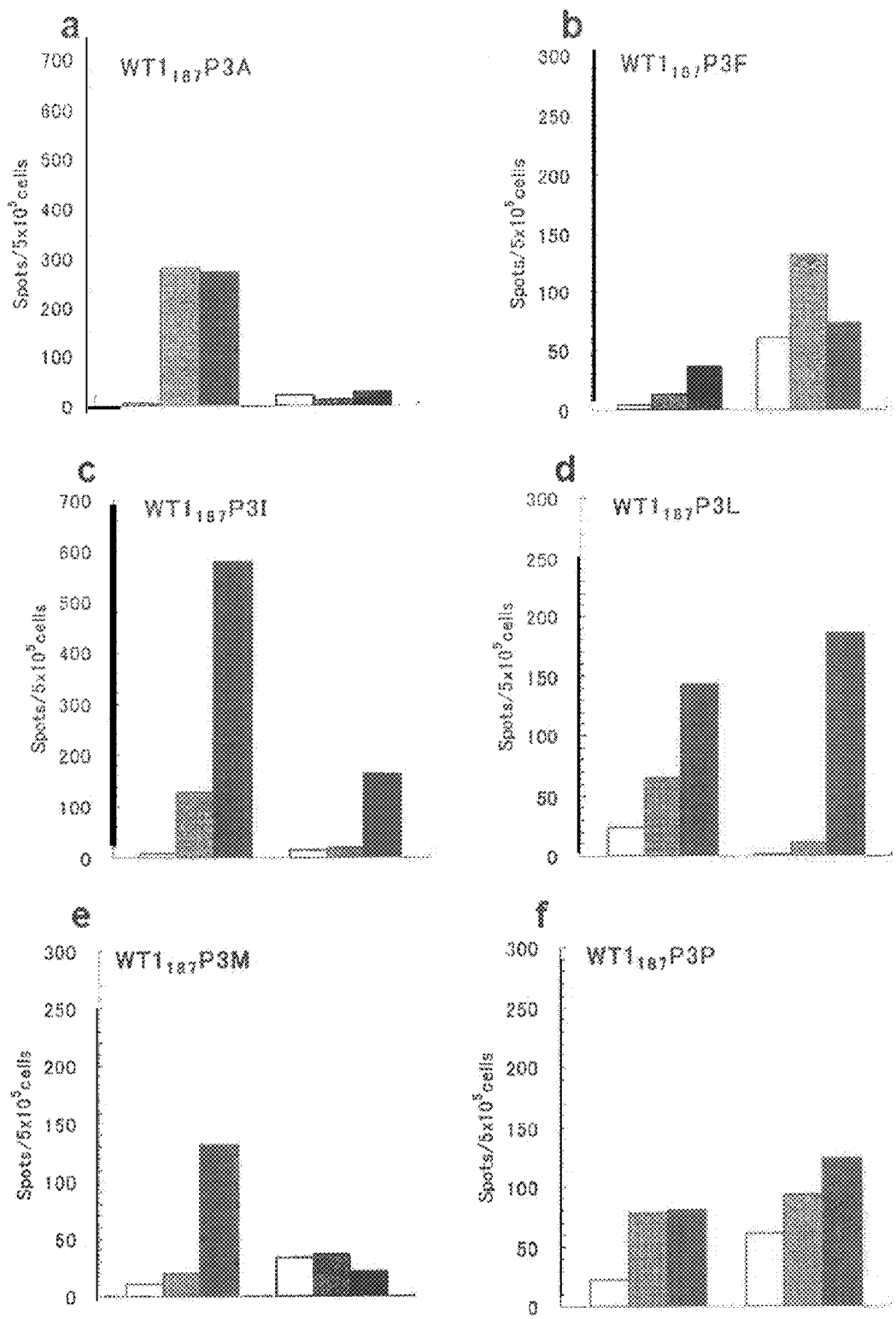
FIG. 21 shows the evaluation results of modified $WT1_{187}$ peptides on the activity of inducing specific cell-mediated immunity.

FIG. 21 a: $WT1_{187}P3A$ peptide, b: $WT1_{187}P3F$ peptide, c: $WT1_{187}P3I$ peptide, d: $WT1_{187}P3L$ peptide, e: $WT1_{187}P3M$ peptide, f: $WT1_{187}$ P3P peptide.

Figure 22:
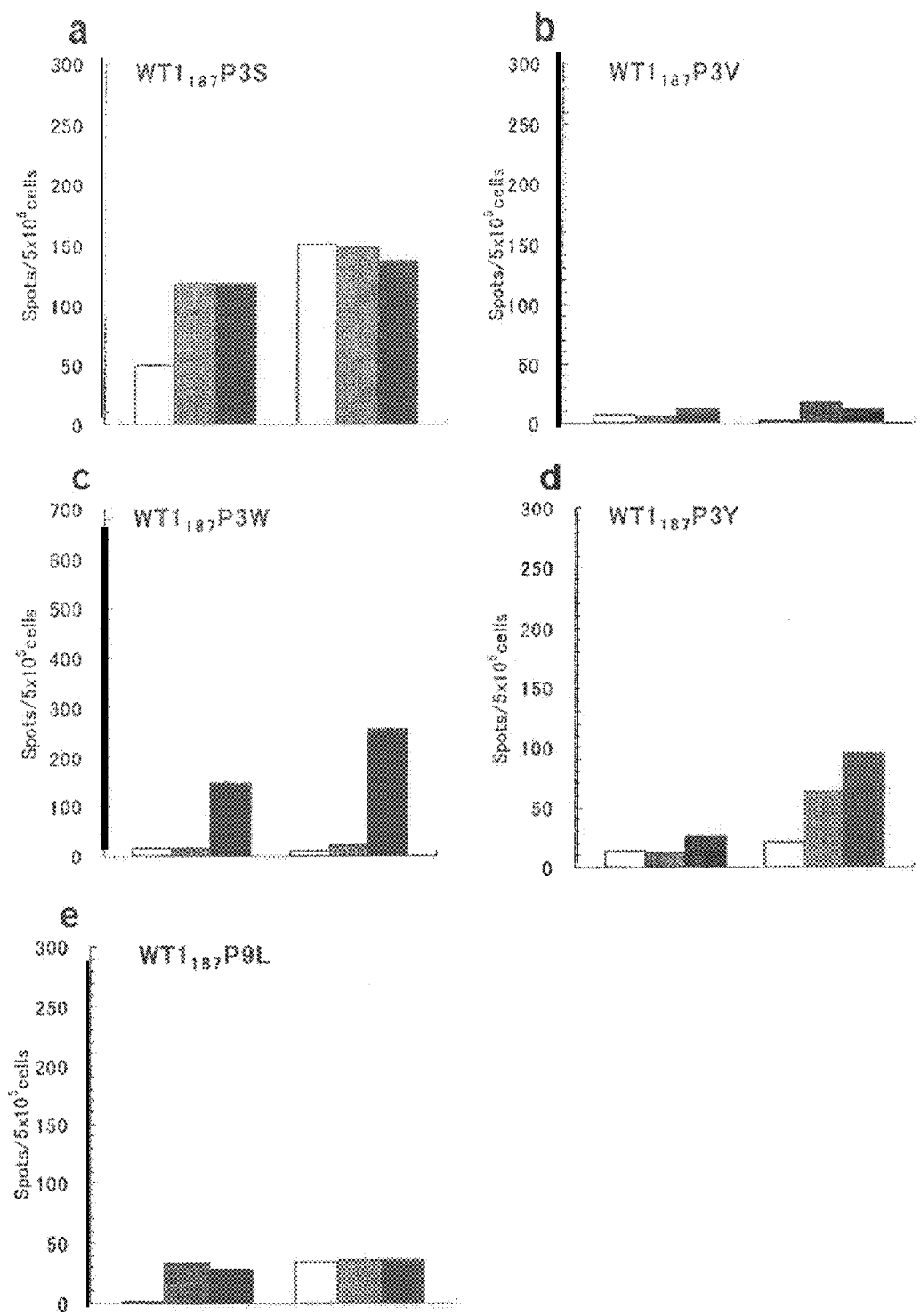
FIG. 22 shows the evaluation results of modified $WT1_{187}$ peptides on the activity of inducing specific cell-mediated immunity.

FIG. 22 a: $WT1_{187}P3S$ peptide, b: $WT1_{187}P3V$ peptide, c: $WT1_{187}P3W$ peptide, d: $WT1_{187}P3Y$ peptide, e: $WT1_{187}P9L$ peptide.

Figure 23:
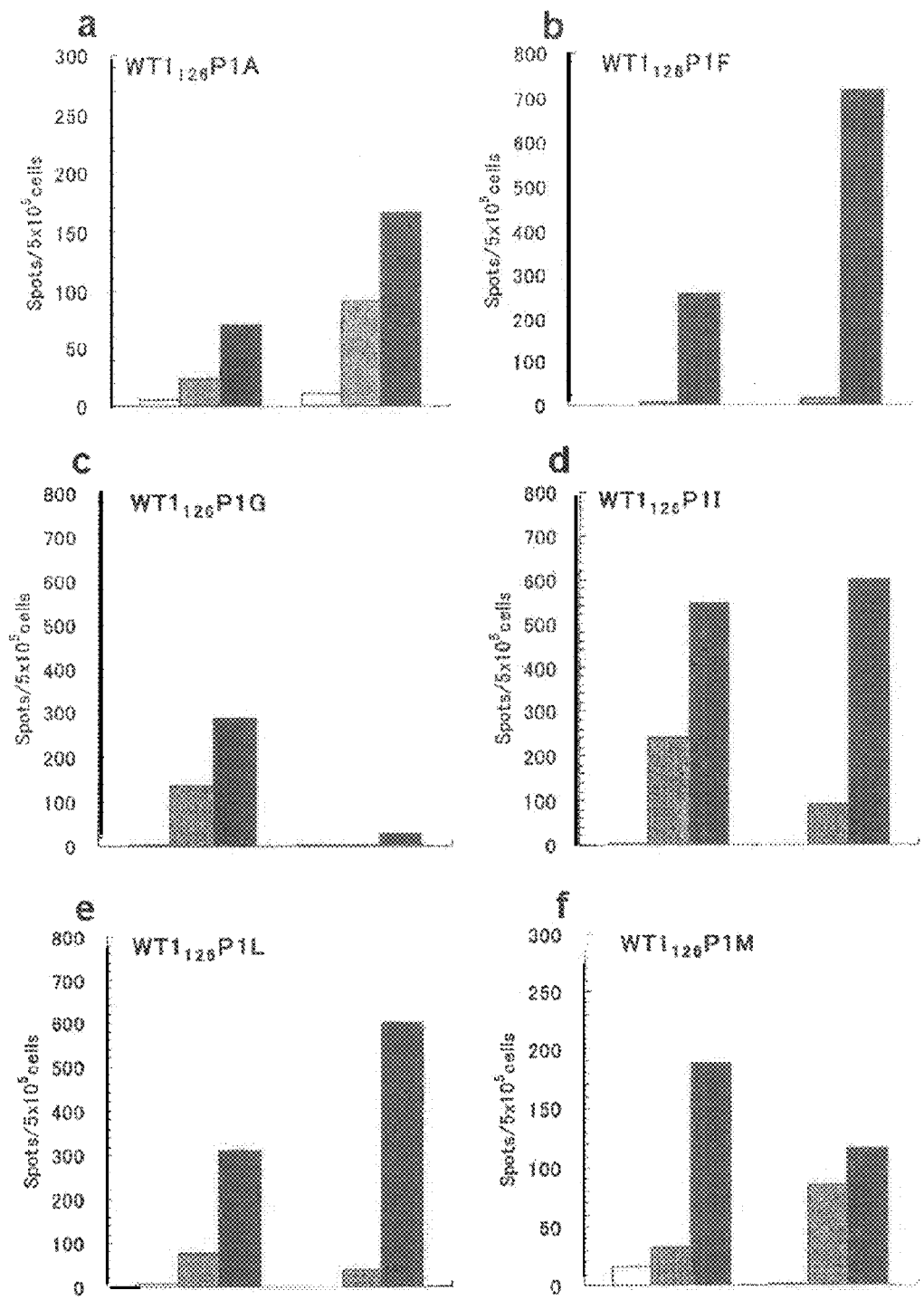
FIG. 23 shows the evaluation results of modified $WT1_{126}$ peptides on the activity of inducing specific cell-mediated immunity.

FIG. 23 a: $WT1_{126}P1A$ peptide, b: $WT1_{126}P1F$ peptide, c: $WT1_{126}P1G$ peptide, d: $WT1_{126}P1I$ peptide, e: $WT1_{126}P1L$ peptide, f: $WT1_{126}P1M$ peptide.

Figure 24:
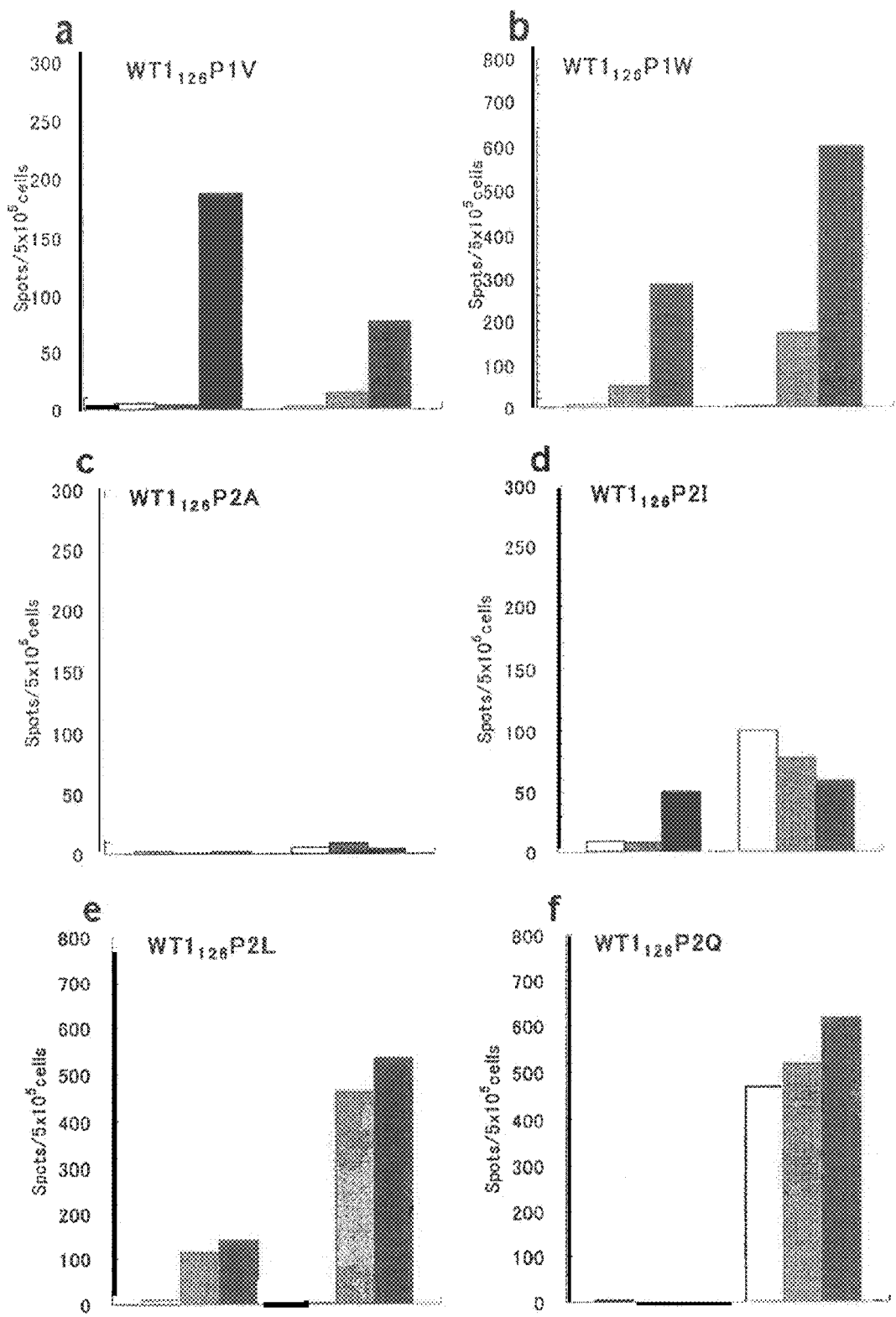
FIG. 24 shows the evaluation results of modified $WT1_{126}$ peptides on the activity of inducing specific cell-mediated immunity.

FIG. 24 a: $WT1_{126}P1V$ peptide, b: $WT1_{126}P1W$ peptide, c: $WT1_{126}P2A$ peptide, d: $WT1_{126}P2I$ peptide, e: $WT1_{126}P2L$ peptide, f: $WT1_{126}P2Q$ peptide.

Figure 25:
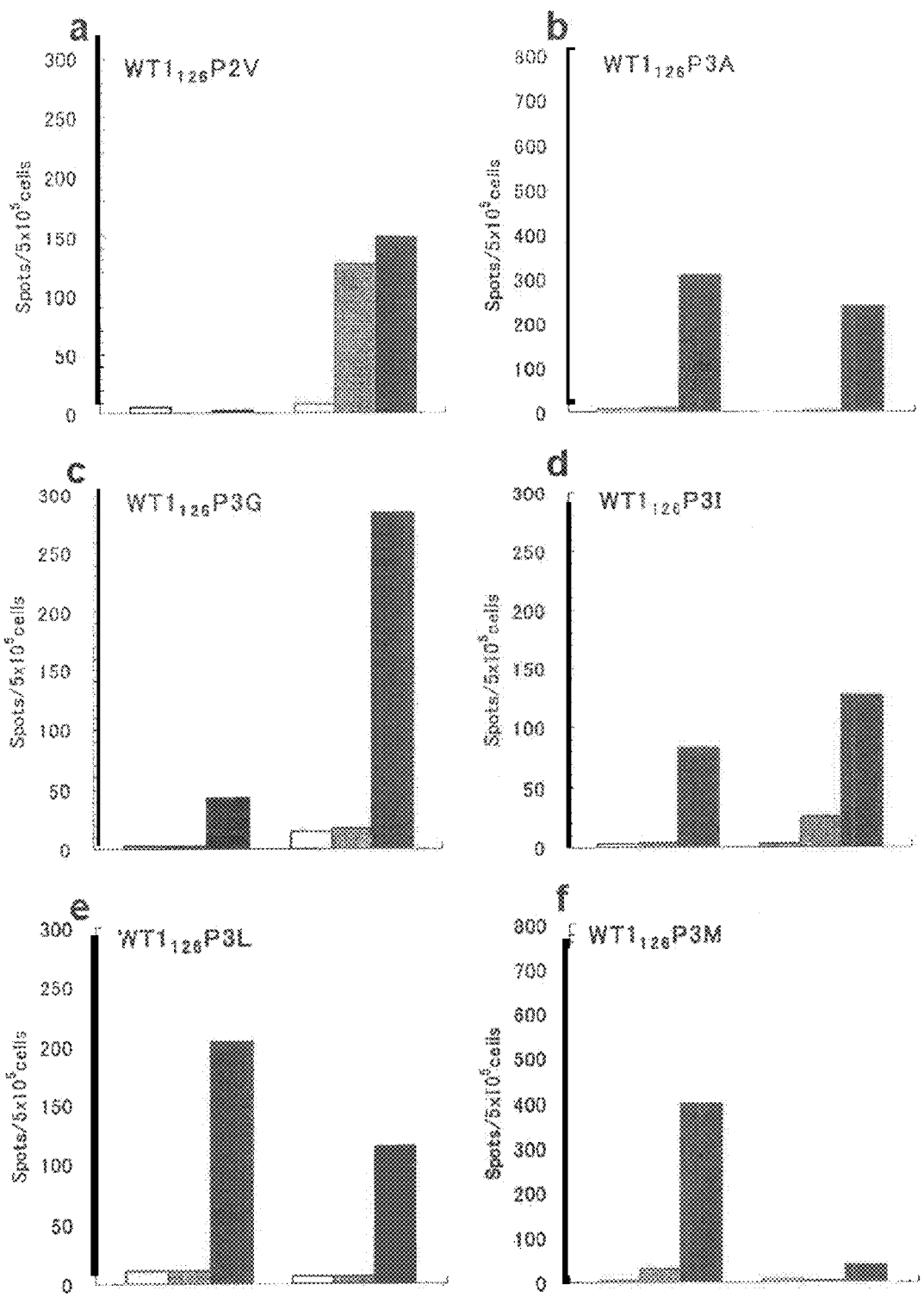
FIG. 25 shows the evaluation results of modified WT1$_{126}$ peptides on the activity of inducing specific cell-mediated immunity.

FIG. 25 a: $WT1_{126}P2V$ peptide, b: $WT1_{126}P3A$ peptide, c: $WT1_{126}P3G$ peptide, d: $WT1_{126}P3I$ peptide, e: $WT1_{126}P3L$ peptide, f: $WT1_{126}P3M$ peptide.

Figure 26:
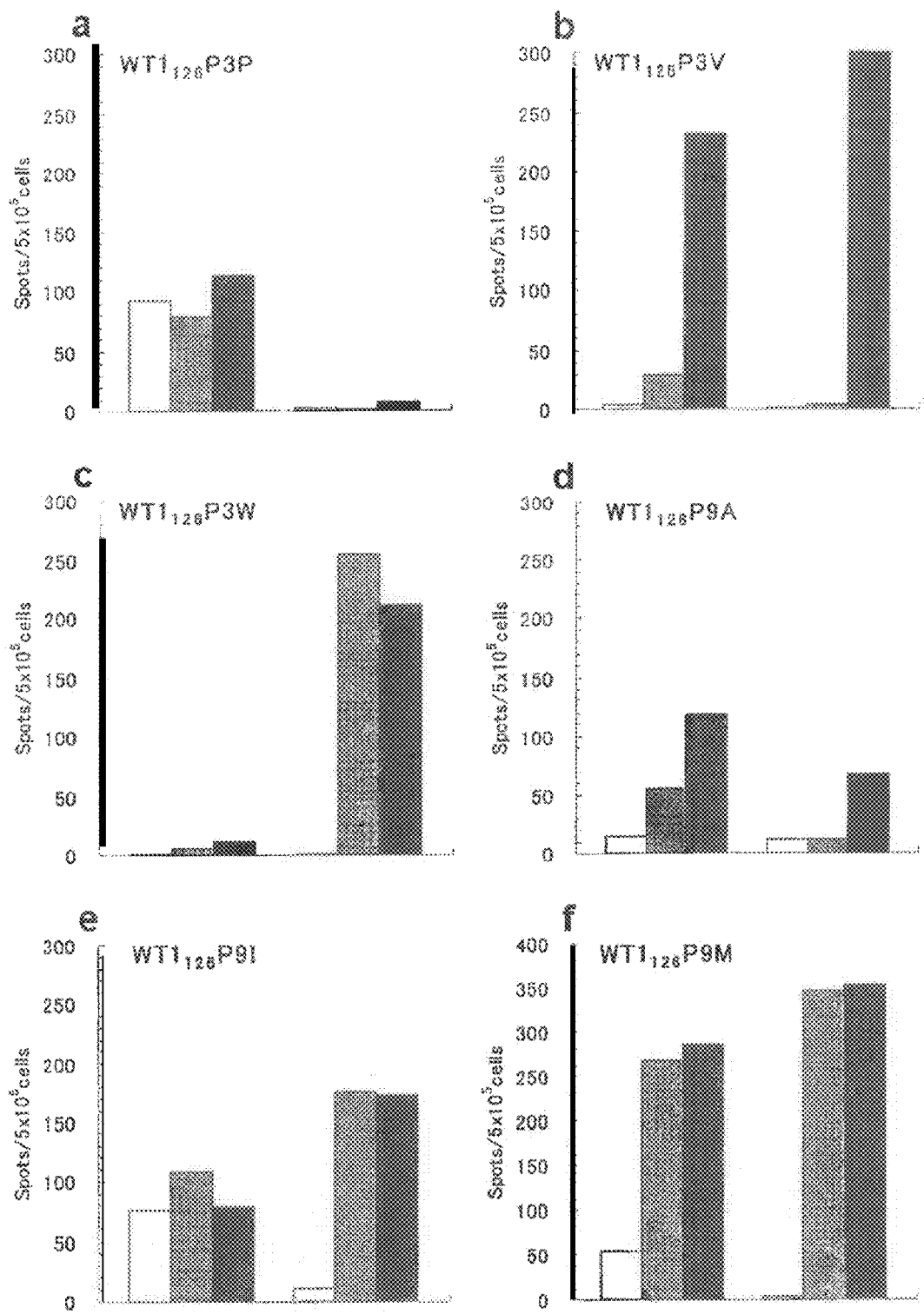
FIG. 26 shows the evaluation results of modified WT1$_{126}$ peptides on the activity of inducing specific cell-mediated immunity.

FIG. 26 a: $WT1_{126}P3P$ peptide, b: $WT1_{126}P3V$ peptide, c: $WT1_{126}P3W$ peptide, d: $WT1_{126}P9A$ peptide, e: $WT1_{126}P9I$ peptide, f: $WT1_{126}P9M$ peptide.

Figure 27:
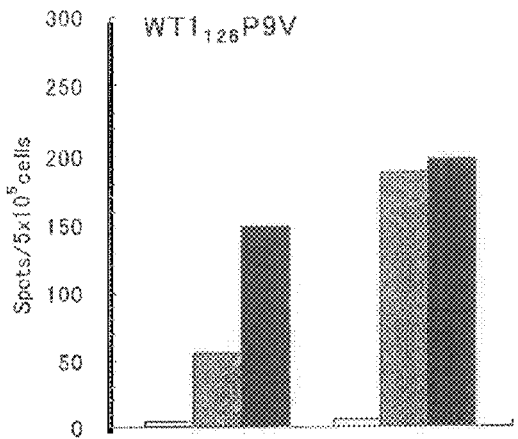
FIG. 27 shows the evaluation results of modified WT1$_{126}$ peptides on the activity of inducing specific cell-mediated immunity.

FIG. 27: $WT1_{126}P9V$ peptide.

Figure 28:
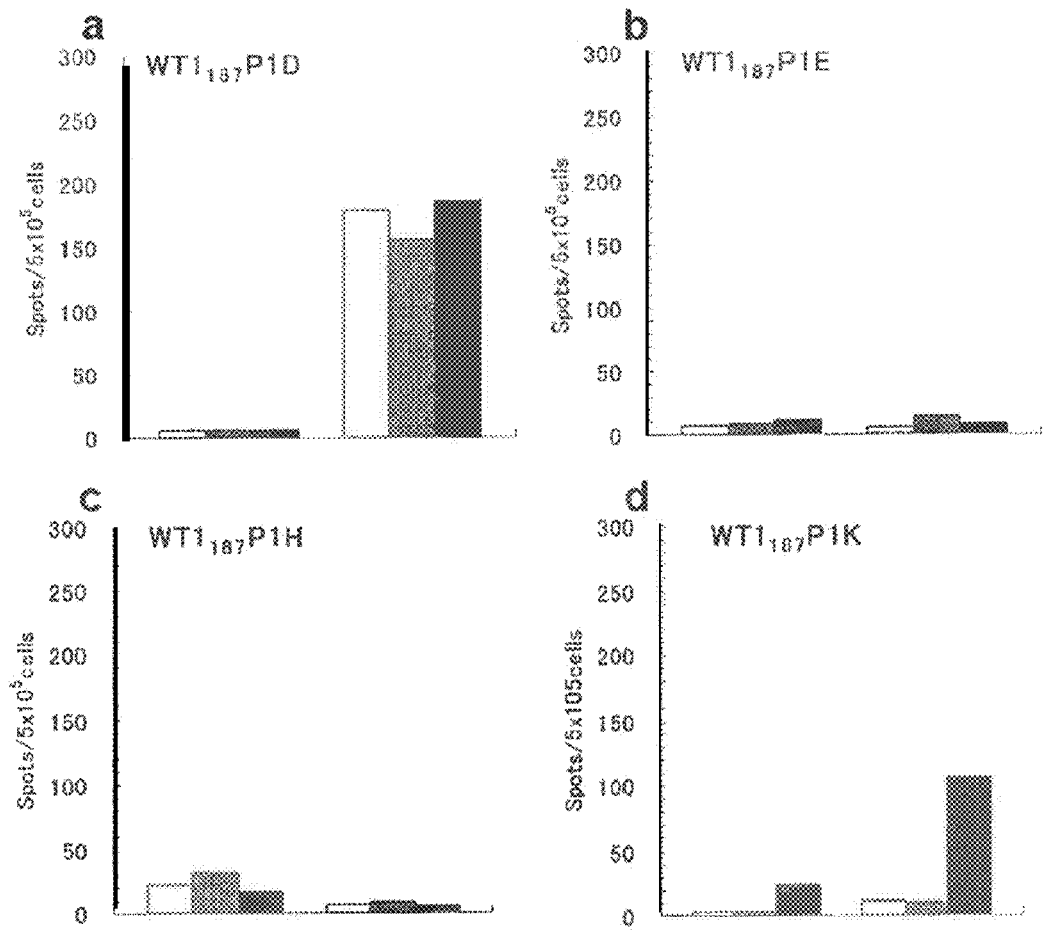
FIG. 28 shows the evaluation results of modified WT1$_{187}$ peptides on the activity of inducing specific cell-mediated immunity.

FIG. 28 a: $WT1_{187}P1D$ peptide, b: $WT1_{187}P1E$ peptide, c: $WT1_{187}P1H$ peptide, d: $WT1_{187}P1K$ peptide.

Figure 29:
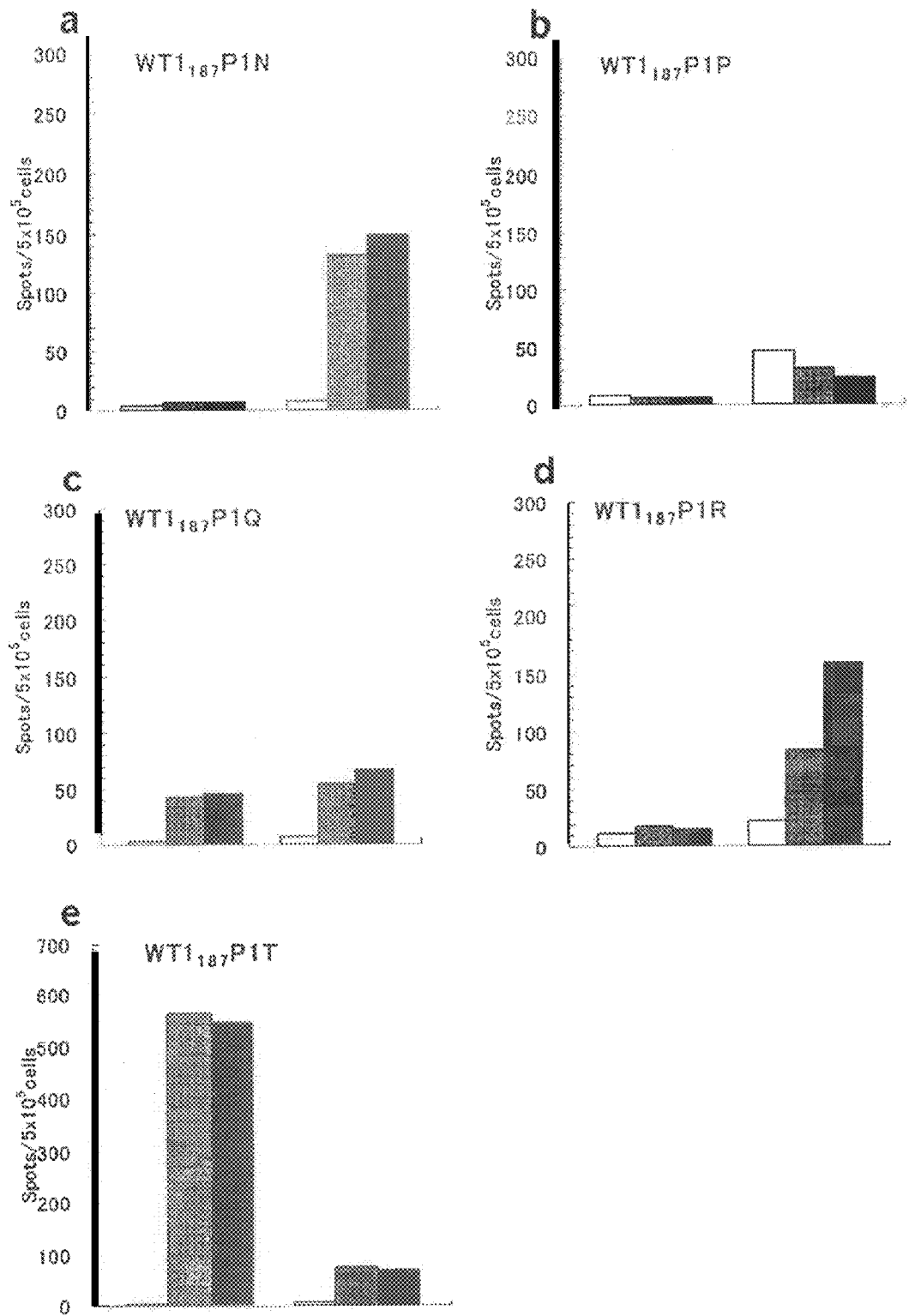
FIG. 29 shows the evaluation results of modified WT1$_{187}$ peptides on the activity of inducing specific cell-mediated immunity.

FIG. 29 a: $WT1_{187}P1N$ peptide, b: $WT1_{187}P1P$ peptide, c: $WT1_{187}P1Q$ peptide, d: $WT1_{187}P1R$ peptide, e: $WT1_{187}P1T$ peptide.

Figure 30:
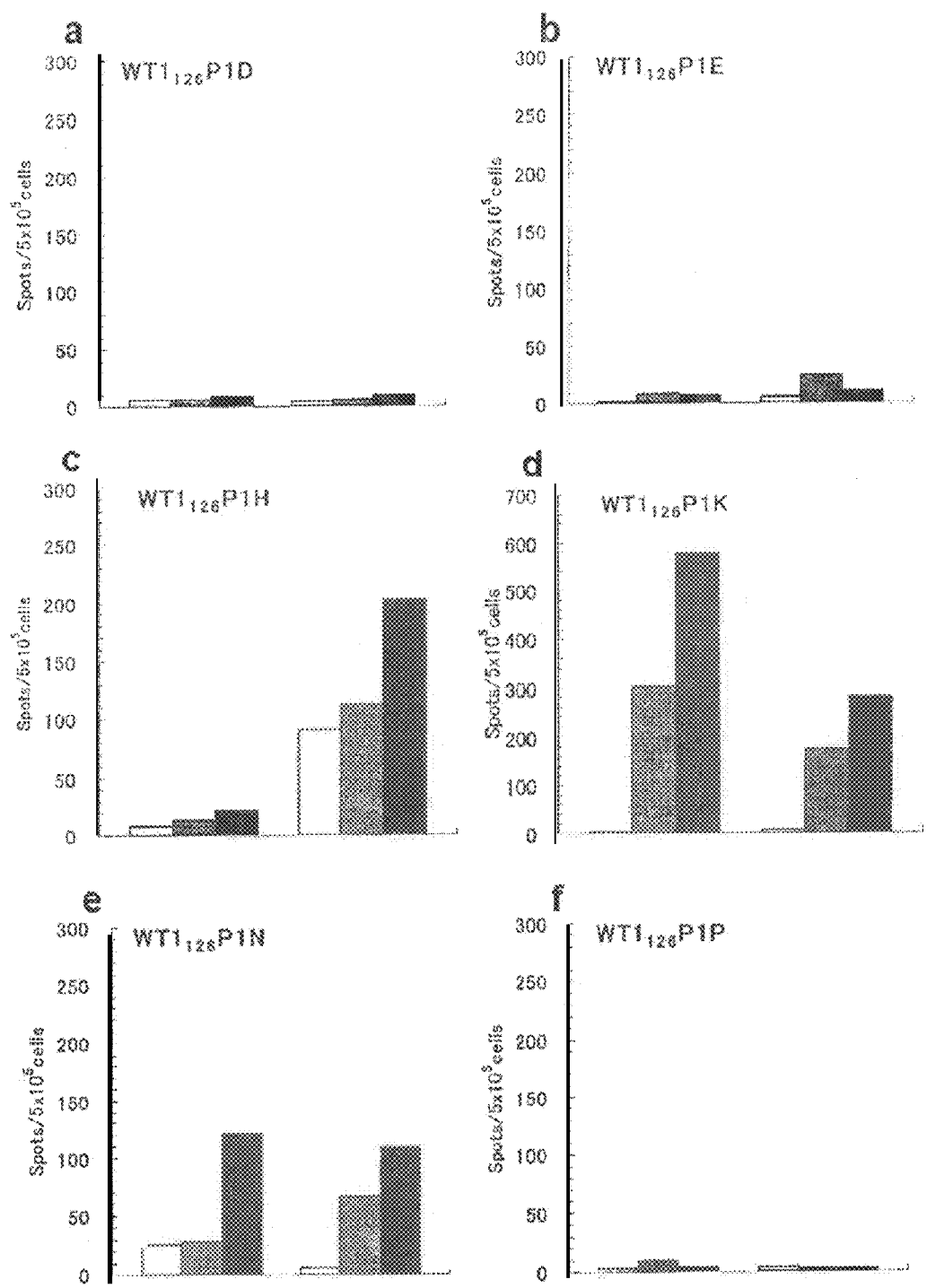
FIG. 30 shows the evaluation results of modified WT1$_{126}$ peptides on the activity of inducing specific cell-mediated immunity.

FIG. 30 a: $WT1_{126}P1D$ peptide, b: $WT1_{126}P1E$ peptide, c: $WT1_{126}P1H$ peptide, d: $WT1_{126}P1K$ peptide, e: $WT1_{126}P1N$ peptide, f: $WT1_{126}P1P$ peptide.

Figure 31:
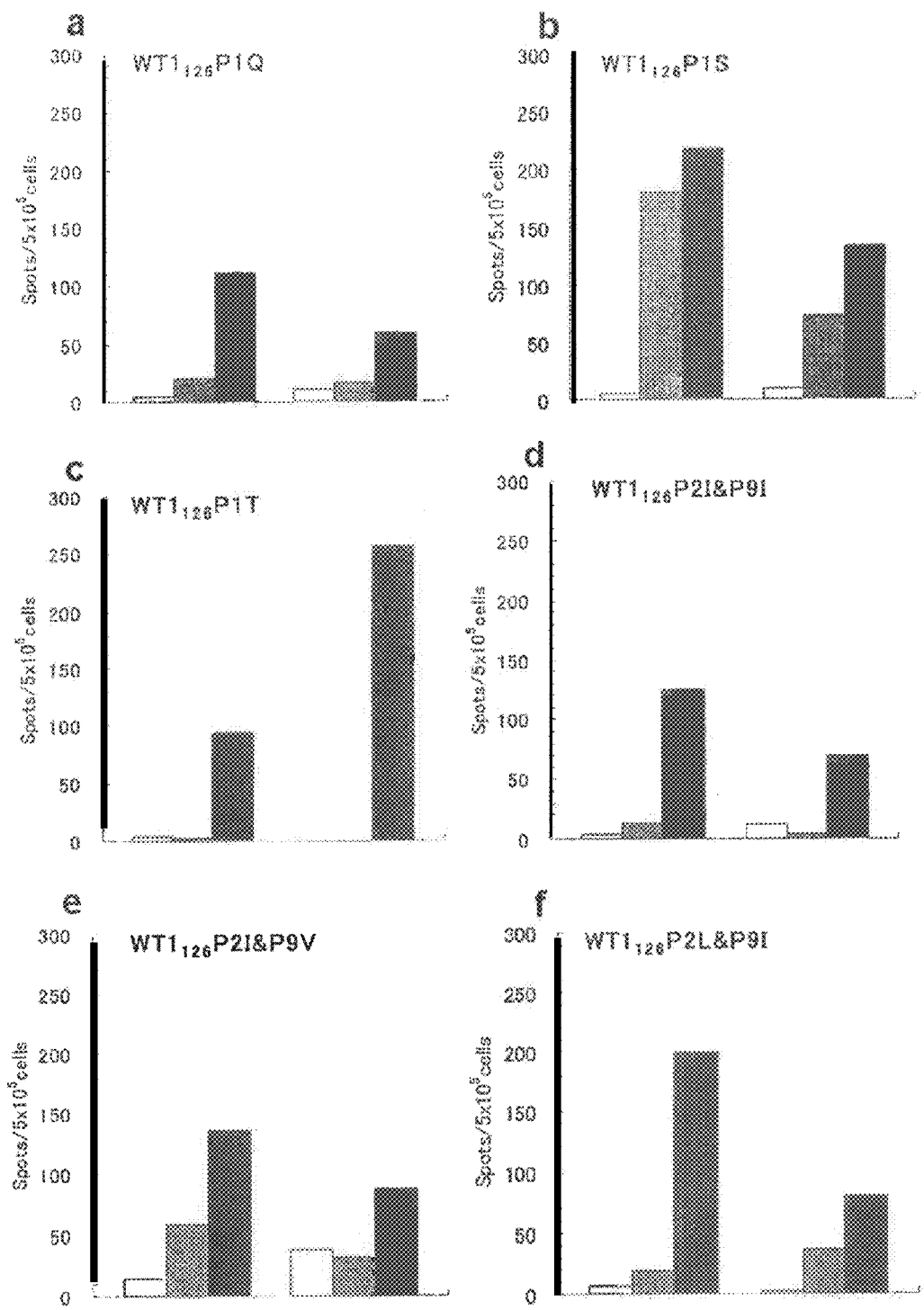
FIG. 31 shows the evaluation results of modified WT1$_{126}$ peptides on the activity of inducing specific cell-mediated immunity.

FIG. 31 a: $WT1_{126}P1Q$ peptide, b: $WT1_{126}P1S$ peptide, c: $WT1_{126}P1T$ peptide, d: $WT1_{126}P2I\&P9I$ peptide, e: $WT1_{126}P2I\&P9V$ peptide, f: $WT1_{126}P2L\&P9I$ peptide.

Figure 32:
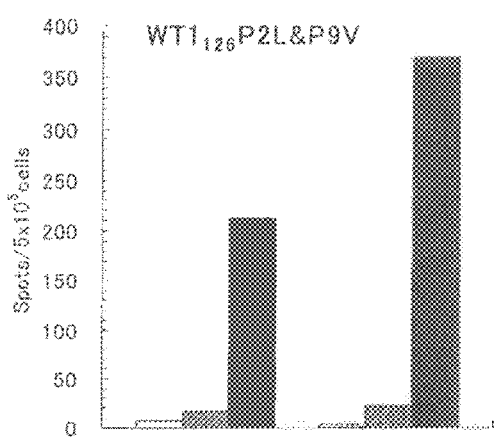
FIG. 32 shows the evaluation results of modified WT1$_{126}$ peptides on the activity of inducing specific cell-mediated immunity.

FIG. 32: $WT1_{126}P2L\&P9V$ peptide.

As shown in these results, when the modified peptides except the $WT1_{187}P1D$ peptide, the $WT1_{187}P1E$ peptide, the $WT1_{187}P1H$ peptide, the $WT1_{187}P1P$ peptide and the $WT1_{187}P2Q$ peptide; the $WT1_{126}P1D$ peptide, the $WT1_{126}P1E$ peptide, the $WT1_{126}P1P$ peptide, the $WT1_{126}P2A$ peptide and the $WT1_{126}P2Q$ peptide were administered into the mice, specific immune cells were remarkably induced in an efficient manner.

Next, the specific immune cells induced by stimulation of the modified peptide were analyzed for the cross reactivity to the wild-type peptide (Tables 24 to 25). The results show that particularly the $WT1_{187}P1A$ peptide, the $WT1_{187}P1I$ peptide, the $WT1_{187}P1L$ peptide, the $WT1_{187}P1M$ peptide, the $WT1_{187}P1N$ peptide, the $WT1_{187}P1Q$ peptide, the $WT1_{187}P1T$ peptide, the $WT1_{187}P1V$ peptide, the $WT1_{187}P2V$ peptide, the $WT1_{187}P2M$ peptide, the $WT1_{187}P2I$ peptide, the $WT1_{187}P3A$ peptide, the $WT1_{187}P3F$ peptide, the $WT1_{187}$ P3P peptide, the $WT1_{187}P3S$ peptide, the $WT1_{187}P3V$ peptide and the $WT1_{187}P9L$ peptide among the $WT1_{187}$ modified peptides; and the $WT1_{126}P1S$ peptide, the $WT1_{126}P2I$ peptide, the $WT1_{126}P2L$ peptide, the $WT1_{126}P2V$ peptide, the $WT1_{126}P3W$ peptide, the $WT1_{126}P9I$ peptide, the $WT1_{126}P9M$ peptide and the $WT1_{126}P9V$ peptide among the $WT1_{128}$ modified peptides, can induce specific immune cells that can efficiently recognize both of the modified peptide and the wild-type peptide.

TABLE 24

| Cross reactivity (%) | Modified $WT1_{187}$ peptide | | | |
|---|---|---|---|---|
| | modified at position 1 | modified at position 2 | modified at position 3 | modified at position 9 |
| 80-100 | $WT1_{187}P1A$<br>$WT1_{187}P1N$<br>$WT1_{187}P1Q$<br>$WT1_{187}P1T$<br>$WT1_{187}P1V$ | $WT1_{187}P2V$<br>$WT1_{187}P2M$<br>$WT1_{187}P2I$ | $WT1_{187}P3A$<br>$WT1_{187}P3P$<br>$WT1_{187}P3S$ | $WT1_{187}P9L$ |
| 60-80 | $WT1_{187}P1I$<br>$WT1_{187}P1L$<br>$WT1_{187}P1M$ | | $WT1_{187}P3F$<br>$WT1_{187}P3V$ | |
| 40-60 | $WT1_{187}P1R$ | | $WT1_{187}P3Y$ | |
| 20-40 | $WT1_{187}P1F$<br>$WT1_{187}P1W$ | | $WT1_{187}P3L$ | |
| 0-20 | $WT1_{187}P1G$<br>$WT1_{187}P1K$ | | $WT1_{187}P3I$<br>$WT1_{187}P3M$<br>$WT1_{187}P3W$ | |
| ND* | $WT1_{187}P1D$<br>$WT1_{187}P1E$<br>$WT1_{187}P1H$<br>$WT1_{187}P1P$ | $WT1_{187}P2Q$ | | |

TABLE 25

| Cross reactivity (%) | Modified $WT1_{126}$ peptide | | | | |
|---|---|---|---|---|---|
| | modified at position 1 | modified at position 2 | modified at position 3 | modified at position 9 | modified at positions 2 & 9 |
| 80-100 | | $WT1_{126}P2L$<br>$WT1_{126}P2V$ | $WT1_{126}P3W$ | $WT1_{126}P9M$<br>$WT1_{126}P9I$ | |
| 60-80 | $WT1_{126}P1S$ | $WT1_{126}P2I$ | | $WT1_{126}P9V$ | |
| 40-60 | $WT1_{126}P1A$<br>$WT1_{126}P1H$<br>$WT1_{126}P1K$<br>$WT1_{126}P1M$<br>$WT1_{126}P1N$ | | | | |
| 20-40 | $WT1_{126}P1G$<br>$WT1_{126}P1I$<br>$WT1_{126}P1Q$<br>$WT1_{126}P1W$ | | | $WT1_{126}P9A$ | |

TABLE 25-continued

| Cross reactivity (%) | Modified WT1_{126} peptide | | | | |
|---|---|---|---|---|---|
| | modified at position 1 | modified at position 2 | modified at position 3 | modified at position 9 | modified at positions 2 & 9 |
| 0-20 | WT1_{126}P1F<br>WT1_{126}P1L<br>WT1_{126}P1T<br>WT1_{126}P1V | | WT1_{126}P3A<br>WT1_{126}P3G<br>WT1_{126}P3I<br>WT1_{126}P3L<br>WT1_{126}P3M<br>WT1_{126}P3P<br>WT1_{126}P3V | | WT1_{126}P2I & P9I<br>WT1_{126}P2I & P9V<br>WT1_{126}P2L & P9I<br>WT1_{126}P2L & P9V |
| ND* | WT1_{126}P1D<br>WT1_{126}P1E<br>WT1_{126}P1P | WT1_{126}P2Q<br>WT1_{126}P2A | | | |

ND*: unmeasurable due to no activity shown

Industrial Applicability

The cancer vaccine composition of the present invention is useful as a medicament used for treatment and prevention of WT1-expressing cancers in HLA-A*0206-positive persons.

The cancer vaccine composition of the present invention is also useful as a medicament used for treatment and prevention of WT1-expressing cancers in HLA-A*0201-positive persons.

The invention claimed is:

1. A method of cancer treatment, comprising administering to an HLA-A*0206-positive person a composition containing a protein which is a gene product of the tumor suppressor gene WT1 or a partial peptide thereof.

2. The method of claim 1, wherein the protein is SEQ ID NO: 1.

3. The method of claim 1, wherein the protein is SEQ ID NO: 2, 3, 11, 16, 20, 34, 39, 46 or 49.

4. The method of claim 1, wherein the protein is SEQ ID NO: 3.

* * * * *

UNITED STATES PATENT AND TRADEMARK OFFICE
CERTIFICATE OF CORRECTION

| | | |
|---|---|---|
| PATENT NO. | : 8,557,779 B2 | Page 1 of 1 |
| APPLICATION NO. | : 12/746257 | |
| DATED | : October 15, 2013 | |
| INVENTOR(S) | : Sugiyama | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this
Tenth Day of March, 2015

Michelle K. Lee
*Deputy Director of the United States Patent and Trademark Office*